US011390864B2

(12) United States Patent
Mather et al.

(10) Patent No.: US 11,390,864 B2
(45) Date of Patent: Jul. 19, 2022

(54) NUCLEIC ACID EXTRACTION MATERIALS, SYSTEMS, AND METHODS

(71) Applicants: ILLUMINA, INC., San Diego, CA (US); ILLUMINA CAMBRIDGE LIMITED, Cambridge (GB)

(72) Inventors: Brian D. Mather, San Diego, CA (US); Cyril Delattre, San Diego, CA (US); Tarun Kumar Khurana, Freemont, CA (US); Yir-Shyuan Wu, Albany, CA (US); Pallavi Daggumati, San Francisco, CA (US); Behnam Javanmardi, Saratoga, CA (US); Filiz Gorpe-Yasar, Redwood City, CA (US); Sebastien Georg Gabriel Ricoult, Cambridge (GB); Xavier von Hatten, Cambridge (GB); Daniel Leonard Fuller, Sudbury (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 0 days.

(21) Appl. No.: 16/626,221

(22) PCT Filed: Jun. 28, 2018

(86) PCT No.: PCT/US2018/040113
§ 371 (c)(1),
(2) Date: Dec. 23, 2019

(87) PCT Pub. No.: WO2019/013991
PCT Pub. Date: Jan. 17, 2019

(65) Prior Publication Data
US 2020/0325467 A1    Oct. 15, 2020

Related U.S. Application Data

(60) Provisional application No. 62/531,751, filed on Jul. 12, 2017, provisional application No. 62/539,890, filed on Aug. 1, 2017, provisional application No. 62/539,876, filed on Aug. 1, 2017.

(51) Int. Cl.
*C07H 21/00* (2006.01)
*C12N 15/10* (2006.01)
*C08F 226/10* (2006.01)

(52) U.S. Cl.
CPC ........ *C12N 15/1017* (2013.01); *C08F 226/10* (2013.01); *C12N 15/1006* (2013.01); *C12N 15/1013* (2013.01)

(58) Field of Classification Search
CPC ............. C12N 15/1006; C12N 15/1013; C08F 226/10
See application file for complete search history.

(56) References Cited

U.S. PATENT DOCUMENTS

| 4,699,717 | A | 10/1987 | Riesner et al. |
| 5,057,426 | A | 10/1991 | Henco et al. |
| 5,374,522 | A | 12/1994 | Murphy et al. |
| 5,582,988 | A | 12/1996 | Backus et al. |
| 6,168,948 | B1 | 1/2001 | Anderson et al. |
| 6,528,264 | B1 | 3/2003 | Pal et al. |
| 6,914,137 | B2 | 7/2005 | Baker |
| 8,617,895 | B2 * | 12/2013 | Fox ........................ G01N 1/405 436/8 |
| 9,753,010 | B2 * | 9/2017 | Jonsson ........... G01N 27/44778 |
| 10,465,183 | B2 * | 11/2019 | Skog ................... C12N 15/1006 |
| 10,632,443 | B2 * | 4/2020 | Berthier ................... A61K 8/11 |
| 2005/0222404 | A1 | 10/2005 | Galaev et al. |
| 2009/0275486 | A1 | 11/2009 | Kurn et al. |
| 2013/0171026 | A1 | 7/2013 | Li et al. |
| 2014/0054172 | A1 | 2/2014 | Jonsson et al. |
| 2014/0093909 | A1 | 4/2014 | Fox et al. |
| 2015/0353920 | A1 * | 12/2015 | Enderle .............. C12N 15/1006 536/25.41 |
| 2017/0198280 | A1 * | 7/2017 | Skog .................. C12N 15/1006 |

FOREIGN PATENT DOCUMENTS

| WO | WO 98/10277 | 3/1998 |
| WO | WO 2016/007755 | 1/2016 |

(Continued)

OTHER PUBLICATIONS

Google search document for Luviquat FC 550 ; Jul. 29, 2021.*
Anon., "Calculatig Percent Passed Filter for Patterned and Nonpatterned Flow Cells," Technical Notes, Illumina, Inc., Pub. No. 770-2014-043-B (2017).*
Asayama, S. et al. Screening for Methylated Poly(L-histidine) With Various Dimethylimidazolium/Methylimidazole/Imidazole Contents as DNA Carrier, Pharmaceutics 2015, 7, pp. 224-232.
Kendall, E. et al., "A Chitosan Coated Monolith for Nucleic Acid Capture in a Thermoplastic Microfluidic Chip", Biomicrofluidics 8, 2014, pp. 044109-1-044109-8.

(Continued)

*Primary Examiner* — Patrick T Lewis
(74) *Attorney, Agent, or Firm* — Illumina, Inc.

(57) ABSTRACT

In the examples set forth herein, nucleic acid extraction materials are capable of selectively extracting cell free nucleic acids, including cell free DNA, directly from whole blood samples or plasma. Also included are methods of making and using the nucleic acid extraction materials. One example of a nucleic acid extraction material includes a substrate. This example of the nucleic acid extraction material also includes a polycation bonded to at least a portion of a surface of the substrate. In this example, the polycation consists of a polymer of a quaternized monomer selected from the group consisting of a quaternized 1-vinylimidazole monomer and a quaternized dimethylaminoethyl methacrylate monomer, or a copolymer of a neutral monomer and the quaternized monomer.

13 Claims, 19 Drawing Sheets

(56) References Cited

FOREIGN PATENT DOCUMENTS

| WO | WO 2016065295 | 4/2016 |
| WO | WO 2017079537 | 5/2017 |

OTHER PUBLICATIONS

Byrnes, S. et al. "Purification and Concentration of Nucleic Acids in Porous Membranes for Point-of-Care Applications", 18th International Conference on Miniaturized Systems for Chemistry and Life Sciences, Oct. 26-30, 2014, San Antonio, TX, pp. 1175-1177.

Dame, G., et al. "Development of a Fast miRNA Extraction System for Tumor Analysis Based on a Simple Lab on Chip Approach", Procedia Engineering, 2015, vol. 120, pp. 158-162.

International Search Report and Written Opinion for International Application No. PCT/US2018/040113 dated Jan. 8, 2019, 19 pages.

* cited by examiner

NUCLEIC ACID EXTRACTION MATERIALS, SYSTEMS, AND METHODS

CROSS-REFERENCE TO RELATED APPLICATIONS

This application claims priority to U.S. Provisional Patent Application No. 62/531,751, filed Jul. 12, 2017; and U.S. Provisional Patent Application No. 62/539,890, filed Aug. 1, 2017; and U.S. Provisional Patent Application No. 62/539,876, filed Aug. 1, 2017; the contents of each of which is incorporated by reference herein in its entirety.

BACKGROUND

Two classes of nucleic acids are found in living organisms (e.g., humans, animals, etc.), namely ribonucleic acid (RNA) and deoxyribonucleic acid (DNA). Both RNA and DNA can be grouped into different types, such as messenger RNA, ribosomal RNA, nuclear DNA, cytoplasmic DNA, etc. The various types of nucleic acids may be analyzed for a variety of purposes, such as research, diagnostics, forensics, genome sequencing, etc. For analysis, a useful nucleic acid product may first be obtained from a biological material using an isolation or extraction process.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

SUMMARY

Figure 1A:
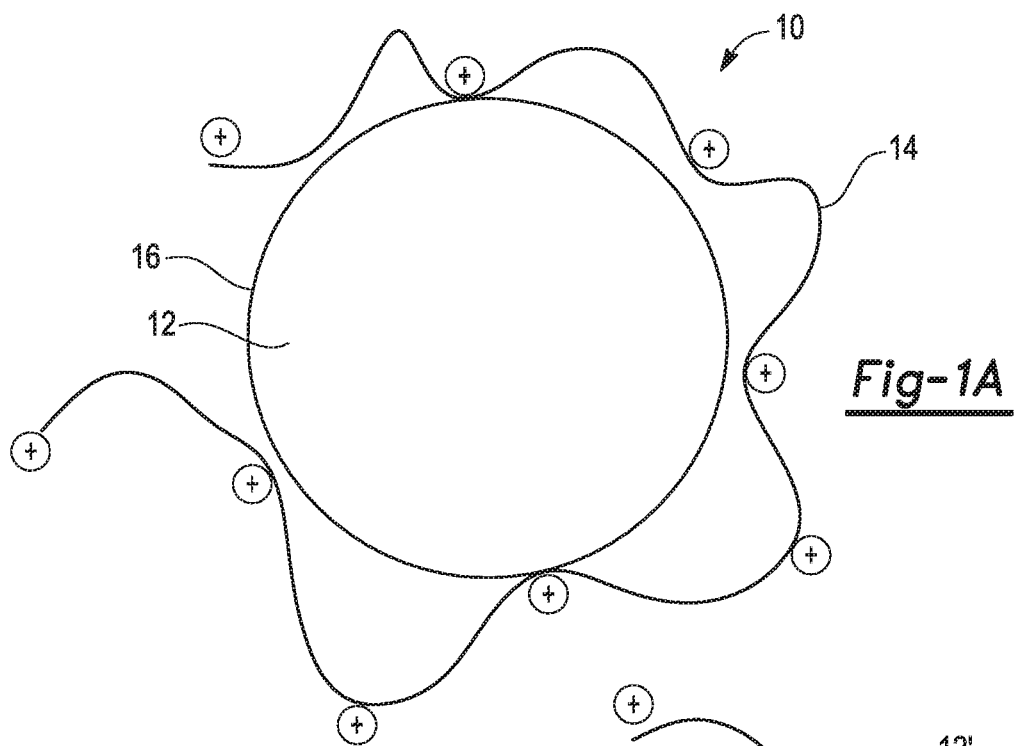
FIG. 1A is a schematic view of an example of a nucleic acid extraction material disclosed herein.

A first aspect includes a nucleic acid extraction material and methods that are defined herein in claims 1-20 and correspond with the claims of U.S. Provisional Patent Application No. 62/531,751, filed Jul. 12, 2017.

In the first aspect, a nucleic acid extraction material comprises a substrate, and a polycation bonded to at least a portion of a surface of the substrate, the polycation consisting of a polymer of a quaternized monomer selected from the group consisting of a quaternized 1-vinylimidazole monomer and a quaternized dimethylaminoethyl methacrylate monomer, or a copolymer of a neutral monomer and the quaternized monomer.

In one example of this nucleic acid extraction material, the neutral monomer is N-vinylpyrrolidone, and the polycation is a cationic copolymer including about 50% of the quaternized 1-vinylimidazole monomer and about 50% of the N-vinylpyrrolidone.

In another example of this nucleic acid extraction material, the neutral monomer is N-vinylpyrrolidone, and the polycation is a cationic copolymer including about 30% of the quaternized 1-vinylimidazole monomer and about 70% of the N-vinylpyrrolidone.

In yet another example of this nucleic acid extraction material, the neutral monomer is N-vinylpyrrolidone, and the polycation is a cationic copolymer including about 95% of the quaternized 1-vinylimidazole monomer and about 5% of the N-vinylpyrrolidone.

In still another example of this nucleic acid extraction material, the neutral monomer is N-vinylpyrrolidone, and the polycation is a cationic copolymer including about 33% of the quaternized dimethylaminoethyl methacrylate monomer and about 67% of the N-vinylpyrrolidone.

In an example of this nucleic acid extraction material, the quaternized 1-vinylimidazole monomer is selected from the group consisting of 3-methyl-1-vinylimidazolium chloride, 3-methyl-1-vinylimidazolium methyl sulfate, and 3-ethyl-1-vinylimidazolium ethyl sulfate.

In an example of this nucleic acid extraction material, the substrate includes a plurality of pores, and the surface to which the polycation is attached is an exterior substrate surface, an interior pore surface, or combinations thereof. In an example, each of the plurality of pores has a diameter that is smaller than a diameter of a cell in a whole blood sample.

In another example of this nucleic acid extraction material, the substrate is selected from the group consisting of controlled pore glass, a metal oxide, a metal with an oxide layer, and combinations thereof.

In still another example of this nucleic acid extraction material, the substrate is a magnetic bead.

In an example of this nucleic acid extraction material, the polycation is physically bonded to the substrate or is chemically bonded to the substrate.

It is to be understood that any features of this aspect of the nucleic acid extraction material may be combined together in any desirable manner and/or configuration.

A first method of the first aspect comprises forming an aqueous solution of a polycation consisting of a polymer of a quaternized monomer selected from the group consisting of a quaternized 1-vinylimidazole monomer and a quaternized dimethylaminoethyl methacrylate monomer, or a copolymer of a neutral monomer and the quaternized monomer; combining a substrate and the aqueous solution to bind at least some of the polycation to the substrate and form a nucleic acid extraction material; and separating the nucleic acid extraction material from the aqueous solution.

In an example, the first method further comprises allowing the substrate and the aqueous solution to incubate for a time period ranging from about 30 minutes to about 72 hours before separating the nucleic acid extraction material from the aqueous solution.

In an example, the neutral monomer is N-vinylpyrrolidone, and the first method further comprises selecting the polycation from the group consisting of i) a cationic copolymer including about 50% of the quaternized 1-vinylimidazole monomer and about 50% of the N-vinylpyrrolidone, ii) a cationic copolymer including about 30% of the quaternized 1-vinylimidazole monomer and about 70% of the N-vinylpyrrolidone, iii) a cationic copolymer including about 95% of the quaternized 1-vinylimidazole monomer and about 5% of the N-vinylpyrrolidone, and iv) a cationic copolymer including about 33% of the quaternized dimethylaminoethyl methacrylate monomer and about 67% of the N-vinylpyrrolidone.

In an example of the first method the aqueous solution includes from about 0.001 wt % of the polycation in water to about 10 wt % of the polycation in water.

In an example of the first method, the substrate is a porous substrate and the method further comprises polishing an exterior surface of the nucleic acid extraction material to remove at least some of the polycation from the exterior surface of the porous substrate.

It is to be understood that any features of the first method may be combined together in any desirable manner. Moreover, it is to be understood that any combination of features of the nucleic acid extraction material and/or of the first method may be used together, and/or that any features from either or both of these may be combined with any of the examples disclosed herein.

A second method of the first aspect comprises selectively extracting at least some cell free deoxyribonucleic acids from a sample of whole blood or plasma by exposing a nucleic acid extraction material to the sample, the nucleic acid extraction material including: a substrate; and a polycation bonded to at least a portion of a surface of the substrate, the polycation to selectively capture and elute the cell free deoxyribonucleic acids; separating the nucleic acid extraction material from the sample of whole blood or plasma; and eluting the extracted cell free deoxyribonucleic acids from the nucleic acid extraction material.

In an example of the second method, the polycation is a cationic copolymer including a quaternized 1-vinylimidazole monomer and a neutral N-vinylpyrrolidone monomer.

In another example of the second method, the polycation is selected from the group consisting of polyquaternium-2, polyquaternium-10, polyquaternium-11, polyquaternium-14, polyquaternium-16, polyquaternium-17, polyquaternium-18, polyquaternium-19, polyquaternium-20, polyquaternium-24, polyquaternium-28, polyquaternium-29, polyquaternium-32, polyquaternium-33, polyquaternium- 34, polyquaternium-35, polyquaternium-36, polyquaternium-37, polyquaternium-39, polyquaternium-42, polyquaternium-43, polyquaternium-44, polyquaternium-45, polyquaternium-46, polyquaternium-47, polyquaternium-53, polyquaternium-63, polyquaternium-73, polyquaternium-91, guar hydroxypropyltrimonium chloride, cationic hydroxyethyl cellulose (HEC) derivatives, hydroxypropyltrimonium hydrolyzed collagen, lauryldimonium hydroxypropyl hydrolyzed collagen, cocodimonium hydroxypropyl hydrolyzed collagen, stearyltrimonium hydroxyethyl hydrolyzed collagen, stearyldimonium hydroxypropyl hydrolyzed collagen, hydroxypropyltrimonium hydrolyzed keratin, cocodimonium hydroxypropyl hydrolyzed hair keratin Cocodimonium, hydroxypropyl hydrolyzed keratin, hydroxypropyltrimonium gelatin, hydroxypropyltrimonium hydrolyzed casein, hydroxypropyltrimonium hydrolyzed wheat protein, cocodimonium hydroxypropyl hydrolyzed wheat protein, lauryldimonium hydroxypropyl hydrolyzed wheat protein, stearyldimonium hydroxypropyl hydrolyzed wheat protein, hydroxypropyltrimonium hydrolyzed soy protein, cocodimonium hydroxypropyl hydrolyzed soy protein, lauryldimonium hydroxypropyl hydrolyzed soy protein, hydroxypropyltrimonium hydrolyzed conchiolin protein, hydroxypropyltrimonium hydrolyzed rice bran protein, hydroxypropyltrimonium hydrolyzed silk protein, hydroxypropyltrimonium hydrolyzed whey protein, hydroxypropyltrimonium jojoba protein, cassia hydroxypropyltrimonium chloride, locust bean hydroxypropyltrimonium chloride, hydroxypropyltrimonium hydrolyzed wheat starch, hydroxypropyltrimonium hydrolyzed corn (maize) starch, hydroxypropyltrimonium hydrolyzed potato starch, hydroxypropyltrimonium hydrolyzed amylopectin, cocodimonium hydroxypropyloxyethyl cellulose, lauryldimonium hydroxypropyloxyethyl cellulose, stearyldimonium hydroxyethyl cellulose, stearyldimonium hydroxypropyl oxyethyl cellulose, guar hydroxypropyltrimonium chloride, and hydroxypropyl guar hydroxypropyltrimonium chloride.

In an example of the second method, eluting involves exposing the separated the nucleic acid extraction material to an elution buffer including a salt.

It is to be understood that any features of the second method may be combined together in any desirable manner. Moreover, it is to be understood that any combination of features of the nucleic acid extraction material and/or of the first method and/or of the second method may be used together, and/or that any features from any of these may be combined with any of the examples disclosed herein.

A second aspect includes systems and methods that are defined herein in claims 21-51 and correspond with the claims of U.S. Provisional Patent Application No. 62/539,876, filed Aug. 1, 2017.

In the second aspect, a first system comprises a separation device having: an inner sample volume for receiving a sample containing nucleic acids of interest; an inner elution volume comprising an elution buffer for receiving the nucleic acids of interest; a nucleic acid filter disposed between the inner sample volume and the inner elution volume; a first electrode disposed adjacent to the inner sample volume; and a second electrode disposed adjacent to the inner elution volume and separated from the nucleic acid filter by the inner elution volume; a power supply coupled to the first and second electrodes that, in operation, supplies a potential difference to between the first and the second electrodes to drive the nucleic acids from the sample through the filter and into the elution buffer; and control circuitry coupled to the power supply and, when in operation, to regulate at least the potential difference and a time of application of the potential difference to cause separation of the nucleic acids of interest from other nucleic acids in the sample based upon molecular size of the nucleic acids of interest.

In an example of the first system, the nucleic acid filter comprises a gel. In an example, the gel comprises an agarose gel.

An example of the first system further comprises a sample inlet, a sample outlet, and a sample pressure source that, in operation, causes the sample to flow from the sample inlet through the inner sample volume, and through the sample outlet. In this example, the first system may further comprise a sample fluid loop between the sample outlet and the sample inlet, wherein the sample is circulated through the sample fluid loop and through the inner sample volume.

An example of the first system further comprises an elution buffer inlet, an elution buffer outlet, and an elution pressure source that, in operation, causes the elution buffer to flow from the elution buffer inlet through the inner elution volume, and through the elution buffer outlet. In this example, the first system may further comprise an elution fluid loop between the elution buffer outlet and the elution buffer inlet, wherein the elution buffer is circulated through the elution fluid loop and through the inner elution volume.

In an example of the first system, the sample comprises a whole blood sample, and wherein the nucleic acids of interest comprise fetal cell free DNA or circulating tumor DNA, or a combination thereof.

An example of the first system further comprises a coating disposed over at least one electrode that prevents electrolysis at the at least one electrode. In an example, the coating comprises a fluorinated polymer.

An example of the first system further comprises a gel disposed between at least one electrode and the inner elution volume that prevents electrolysis of the nucleic acids of interest at the at least one electrode.

An example of the first system further comprises a collection medium in contact with the elution buffer to collect DNA driven through the nucleic acid filter.

It is to be understood that any features of the first system may be combined together in any desirable manner. Moreover, it is to be understood that any combination of features of the material and/or methods of the first aspect and the first system may be used together, and/or that any features from any of these may be combined with any of the examples disclosed herein.

A first method of the second aspect comprises applying a potential difference for a period of time between first and second electrodes to drive nucleic acids from a sample disposed in a sample volume through a filter and into an elution buffer disposed in an elution volume; and collecting nucleic acids of interest from the nucleic acids in the elution buffer, wherein the potential difference and the period of time is determined based on the filter and the nucleic acids of interest.

An example of the first method of the second aspect further comprises causing the sample to flow through the sample volume while the potential difference is being applied between the first and the second electrodes.

An example of the first method of the second aspect further comprises causing an external sample disposed in a reservoir external to the sample volume to flow through the sample volume while the potential difference is being applied between the first and the second electrodes, wherein a volume of the reservoir is larger than a volume of the sample volume.

An example of the first method of the second aspect further comprises causing the elution buffer to flow through the elution volume while the potential difference is being applied between the first and the second electrodes.

It is to be understood that any features of the first method of the second aspect may be combined together in any desirable manner. Moreover, it is to be understood that any combination of features of the material and/or methods of the first aspect and/or the first system and/or the first method of the second aspect may be used together, and/or that any features from any of these may be combined with any of the examples disclosed herein.

A second system method of the second aspect comprises a separation device having: an inner sample volume for receiving a sample containing nucleic acids of interest and other nucleic acids; an inner elution volume comprising an elution buffer for receiving the nucleic acids of interest; a nucleic acid separation filter disposed between the inner sample volume and the inner elution volume; a first electrode disposed adjacent to the inner sample volume; and a second electrode disposed adjacent to the inner elution volume and separated from the nucleic acid separation filter by the inner elution volume, wherein the nucleic acid separation filter is selected to separate the nucleic acids of interest from the other nucleic acids based upon molecular size; and a power supply coupled to the first and second electrodes that, in operation, supplies a potential difference between the first and the second electrodes to drive the nucleic acids of interest from the sample through the filter and into the elution buffer.

In an example of the second system, the nucleic acid separation filter comprises a membrane. In an example, the membrane has a pore size ranging from about 50 nm and about 500 nm.

In an example of the second system, the nucleic acids of interest comprise cell free DNA.

An example of the second system further comprises a controller to: receive a sample characteristic; receive a molecular size of the nucleic acids of interest; receive a characteristic of the nucleic acid separation filter; and regulate at least the time of application of the potential difference to a pre-selected duration based on the molecular size of the nucleic acids of interest, the sample characteristic, and the characteristic of the nucleic acid separation filter. In an example, the controller is to provide a suggested membrane type based on the sample characteristic or the molecular size of the nucleic acid of interest.

An example of the second system further comprises an elution buffer inlet, an elution buffer outlet, and an elution pressure source that, in operation, causes the elution buffer to flow from the elution buffer inlet through the inner elution volume, and through the elution buffer outlet.

An example of the second system further comprises a collection chamber comprising beads having affinity to the nucleic acids of interest.

An example of the second system further comprises a gel disposed between the second electrode and the elution buffer, wherein the gel prevents contact between the nucleic acids of interest and the second electrode.

It is to be understood that any features of the second system of the second aspect may be combined together in any desirable manner. Moreover, it is to be understood that any combination of features of the material and/or methods of the first aspect and/or the first and/or second systems and/or the first method of the second aspect may be used together, and/or that any features from any of these may be combined with any of the examples disclosed herein.

A third system method of the second aspect comprises a separation device having: an inner sample chamber for receiving a sample containing nucleic acids of interest; an inner elution chamber comprising an elution buffer for receiving the nucleic acids of interest; and a nucleic acid filter disposed between the inner sample chamber and the inner elution chamber; a first electrode disposed adjacent to the inner sample volume; and a second electrode disposed adjacent to the inner elution volume; and a fluidic concentration system comprising a pump that circulates the sample through the inner sample chamber to concentrate the nucleic acids of interest of the sample in the inner sample chamber, wherein a volume of the sample is larger than a volume of the inner sample chamber.

In an example of the third system, the nucleic acid filter comprises a membrane.

In an example of the third system, the nucleic acid filter comprises a gel.

In an example of the third system, the fluidic concentration system comprises a sample reservoir that is coupled to the inner sample chamber by the pump, wherein a volume of the sample reservoir comprises a portion of the sample.

In an example of the third system, the sample comprises a whole blood sample.

In an example of the third system, the nucleic acids of interest comprise cell free DNA or a circulating tumor DNA.

It is to be understood that any features of the third system of the second aspect may be combined together in any desirable manner. Moreover, it is to be understood that any combination of features of the material and/or methods of the first aspect and/or the first and/or second and/or third systems and/or the first method of the second aspect may be used together, and/or that any features from any of these may be combined with any of the examples disclosed herein.

A third aspect includes systems and methods that are defined herein in claims 52-71 and correspond with the claims of U.S. Provisional Patent Application No. 62/539,890, filed Aug. 1, 2017.

A first system of the third aspect comprises a separation device having: an inner sample volume for receiving a sample containing a nucleic acid of interest; a mechanical lysis medium disposed in the inner sample volume; an inner elution volume comprising an elution buffer for receiving the nucleic acid of interest; a nucleic acid separation filter disposed between the inner sample volume and the inner elution volume; a first electrode disposed adjacent to the inner sample volume; and a second electrode disposed adjacent to the inner elution volume; an energy source that in operation applies energy to the mechanical lysis medium to lyse cells within the sample to release the nucleic acid of interest; and a power supply coupled to the first and second electrodes that, in operation, supplies a potential difference to the electrodes to drive the released nucleic acid of interest from the inner sample volume through the filter and into the inner elution volume.

In an example of the first system of the third aspect, the nucleic acid separation filter comprises a membrane having a pore size ranging from about 0.01 µm to about 0.45 µm.

In an example of the first system of the third aspect, the mechanical lysis medium comprises glass beads. In an example, the glass beads have a diameter ranging from about 100 µm to about 150 µm.

In an example of the first system of the third aspect, the elution buffer comprises chemical tags for performing a tagmentation process.

In an example of the first system of the third aspect, the separation device comprises a sample inlet channel for loading the sample, and an elution outlet channel for extracting the separated nucleic acid in the elution buffer. In an example, the separation device comprises a sample outlet channel for allowing escape of gas from the inner sample volume upon loading of the sample. In another example, the separation device comprises an elution inlet channel for aiding on moving the separated nucleic acid and elution buffer towards an extraction port.

In an example of the first system of the third aspect, the energy source comprises an ultrasound vibration source.

An example of the first system of the third aspect further comprises control circuitry coupled to the power supply to regulate at least the potential difference applied to the electrodes and the time of application of the potential difference.

It is to be understood that any features of the first system of the third aspect may be combined together in any desirable manner and/or configuration.

A second system of the third aspect an inner sample volume for receiving a sample containing DNA of interest; a mechanical lysis medium disposed in the inner sample volume; an inner elution volume comprising an elution buffer for receiving the DNA of interest; a DNA separation filter disposed between the inner sample volume and the inner elution volume; a first electrode disposed adjacent to the inner sample volume; and a second electrode disposed adjacent to the inner elution volume.

In an example of the second system of the third aspect, the DNA separation filter comprises a membrane having a pore size ranging from about 0.01 μm to about 0.45 μm.

In an example of the second system of the third aspect, the mechanical lysis medium comprises glass beads. In an example, the beads have a diameter ranging from about 100 μm and about 150 μm.

It is to be understood that any features of the second system of the third aspect may be combined together in any desirable manner. Moreover, it is to be understood that any combination of features of the first system and/or of the second system of the third aspect may be used together, and/or that any features from any of these may be combined with any of the examples disclosed herein.

A method of the third aspect comprises loading a sample comprising biological cells into a sample volume of a separation device, the sample volume comprising a mechanical lysis medium; applying energy to the lysis medium to lyse the cells of the sample; applying a potential difference to first and second electrodes of the separation device to separate DNA from the lysed sample cells across a filter into an elution buffer contained in an elution volume of the separation device; and extracting the elution buffer and separated DNA from the elution volume.

In an example of the method of the third aspect, the energy applied to the lysis medium comprises acoustic energy.

An example of the method of the third aspect further comprises regulating at least the potential difference applied to the electrodes and the time of application of the potential difference.

An example of the method of the third aspect further comprises tagging the separated DNA with adaptor oligonucleotides to obtain double stranded DNA fragments; and thermocycling the double stranded DNA fragments to produce a DNA library for sequencing.

An example of the method of the third aspect further comprises concentrating the sample in the sample volume.

In an example of the method of the third aspect, the biological cells comprise bacterial cells, and the separated DNA comprises genomic DNA.

It is to be understood that any features of the method of the third aspect may be combined together in any desirable manner. Moreover, it is to be understood that any combination of features of the first system and/or of the second system of the third aspect may be used together with the method of the third aspect, and/or that any features from any of these may be combined with any of the examples disclosed herein.

DETAILED DESCRIPTION

Certain physiological or environmental conditions may lead to the release of cell free nucleic acids (i.e., nucleic acids that are not inside cells) in solution. By way of example, fetal cell free DNA may be released in the blood stream of pregnant women by placenta tissues, or cell free DNA may be present in blood circulation of certain patients suffering from cancer or sepsis. In some situations, extraction of cell free nucleic acids may be useful for diagnosis and characterization from blood or other biological tissues. Many known extraction methods for cell free nucleic acids (e.g., cell free deoxyribonucleic acids (cfDNA) or cell free ribonucleic acids (cfRNA)) utilize plasma samples rather than whole blood samples. This is due to the fact that these methods involve upfront lysis, which would rupture white blood cells in whole blood and lead to genomic nucleic acid (e.g., genomic DNA) contamination.

Contrary to these types of extraction methods, examples of the nucleic acid extraction material disclosed herein can selectively extract cell free nucleic acids directly from whole blood samples.

Examples of the nucleic acid extraction material disclosed herein include a substrate and a polycation bonded to at least a portion of a surface of the substrate. The polycations disclosed herein can selectively extract cell free nucleic acids (cfNA) directly from a whole blood sample or a plasma sample, and the extracted cfNA can readily be eluted from the nucleic acid extraction material for further processing. By "selectively extract cell free NA," it is meant that the polycations disclosed herein primarily extract cfNA, although proteins and some genomic nucleic acids (as described below) may also be extracted. By "primarily extract," it is meant that the nucleic acid extraction material disclosed herein extracts more cfNA than many of the known extraction methods that involve upfront lysis. For example, isolated samples from the known extraction methods involving upfront lysis would contain at least 99% of genomic nucleic acids and 1% or less of cfNA, and isolated samples from the nucleic acid extraction material disclosed herein include 80% or less of genomic nucleic acids and 20% or more of cfNA.

The bonded polycations disclosed herein are unlike other polycations (e.g., bonded polyethyleneimine) because they lyse fewer white blood cells (i.e., leukocytes) or red blood cells in the sample than other polycations during cfNA extractions. The increased lysis from bonded polyethyleneimine may be due to its high charge density. It is believed that because the bonded polycations disclosed herein lyse fewer or none of the white blood cells during cfNA extraction from a mammal (e.g., human) whole blood or plasma sample, little or no genomic nucleic acids (e.g., genomic DNA (gDNA) are extracted. As such, there is little or no genomic nucleic acid contamination in the isolated sample of cfNA. By little or no genomic nucleic acid contamination, it is meant that the isolated sample contains 80% or less of genomic nucleic acids (of the total isolated sample), or in some instances, 60% or less of genomic nucleic acids, or in still other instances, the percentage of genomic nucleic acids is not detectable. These percentages assume that the whole blood or plasma sample is not lysed prior to performing the method(s) disclosed herein. The level of genomic nucleic acid contamination is highly sample dependent, as some blood samples are more prone to lysis than others.

The bonded polycations disclosed herein are also unlike other polycations (e.g., polyethyleneimine) because they efficiently release the cfNA via elution. Electrophoresis may be performed on samples post elution, and these results are indicative of the amount of cfNA that is eluted. Based on the results of Example 6 below, cfDNA amounts captured and eluted with polyethyleneimine are lower than cfDNA amounts captured and eluted with examples of the nucleic acid extraction materials disclosed herein.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, "cell free nucleic acids" and "cell free NA" (cfNA) refers to DNA or RNA that is not contained within cells. Some cfDNA or cfRNA may be associated with a protein. As an example, cfDNA may be at least partially wrapped around histone proteins in nucleosomes. These nucleosomes may or may not be inside apoptotic vesicles. The nucleic acid extraction materials disclosed herein may not capture the apoptotic vesicles. As examples, cfDNA or cfRNA may be cell free fetal DNA or RNA or cell free tumor DNA or RNA. Cell free fetal DNA or RNA is the DNA or RNA of a fetus that is circulating freely in the maternal blood stream. Cell free tumor DNA or RNA is tumor-derived fragmented DNA (i.e., circulating tumor DNA or ctDNA) or RNA. The examples disclosed herein may also be suitable for capturing and eluting viral DNA or viral RNA and/or bacterial DNA or bacterial RNA.

Also as used herein, "genomic nucleic acids" (gNA, such as gDNA or gRNA) refers to high molecular weight (>1000 bp) chromosomal DNA or RNA. In a whole blood sample of a mammal, the gDNA is contained within white blood cells. In a whole blood sample of a bird, fish, or reptile, the gDNA is contained within red blood cells.

As used herein, a "nucleic acid extraction material" refers to structure that is capable of both extracting cfNA from a whole blood sample and is also capable of having the extracted cfNA readily eluted therefrom. The nucleic acid extraction material consists of a substrate and a particular polycation bonded to at least a portion of a surface of the substrate. The nucleic acid extraction material can also extract and elute cfNA from plasma samples.

A "nucleotide," as used herein, includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, "polycation" refers to any cation that has more than one positive charge, and that is capable of selectively capturing and eluting cfNA from a whole blood sample and from a plasma sample. As discussed above, "selective capture" or "selective extraction" means that the polycation primarily extracts cfNA, although proteins and some genomic nucleic acids may also be extracted. In an example, the polycation consists of a polymer of a quaternized monomer selected from the group consisting of a quaternized 1-vinylimidazole monomer and a quaternized dimethylaminoethyl methacrylate monomer, or a copolymer of a neutral monomer and the quaternized monomer. In another example, the polycation is selected from the group is selected from the group consisting of polyquaternium-2 (i.e., poly[bis(2-chloroethyl) ether-alt-1,3-bis[3-(dimethylamino)propyl]urea]), polyquaternium-10 (i.e., quaternized hydroxyethyl cellulose), polyquaternium-11 (i.e., copolymer of vinylpyrrolidone and quaternized dimethylaminoethyl methacrylate), polyquaternium-14 (i.e., trimethylaminoethylmethacrylate homopolymer), polyquaternium-16 (i.e., copolymer of vinylpyrrolidone and quaternized vinylimidazole), polyquaternium-17 (i.e., adipic acid, dimethylaminopropylamine and dichloroethylether copolymer), polyquaternium-18 (i.e., azelanic acid, dimethylaminopropylamine and dichloroethylether copolymer), polyquaternium-19 (i.e., copolymer of polyvinyl alcohol and 2,3-epoxypropylamine), polyquaternium-20 (i.e., copolymer of polyvinyl octadecyl ether and 2,3-epoxypropylamine), polyquaternium-24 (i.e., quaternary ammonium salt of hydroxyethyl cellulose reacted with a lauryl dimethyl ammonium substituted epoxide), polyquaternium-28 (i.e., copolymer of vinylpyrrolidone and methacrylamidopropyl trimethylammonium), polyquaternium-29 (i.e., chitosan modified with propylene oxide and quaternized with epichlorohydrin), polyquaternium-32 (i.e., poly(acrylamide 2-methacryloxyethyltrimethyl ammonium chloride)), polyquaternium-33 (i.e., copolymer of trimethylaminoethylacrylate salt and acrylamide), polyquaternium-34 (i.e., copolymer of 1,3-dibromopropane and N,N-diethyl-N',N'-dimethyl-1,3-propanediamine), polyquaternium-35 (i.e., methylsulfate salt of the copolymer of methacryloyloxyethyltrimethylammonium and of methacryloyloxyethyldimethylacetylammonium), polyquaternium-36 (i.e., copolymer of N,N-dimethylaminoethylmethacrylate and butylmethacrylate, quaternized with dimethyl sulfate), polyquaternium-37 (i.e., poly(2-methacryloxyethyltrimethylammonium chloride)), polyquaternium-39 (i.e., terpolymer of acrylic acid, acrylamide and diallyldimethylammonium chloride), polyquaternium-42 (i.e., poly[oxyethylene(dimethylimino)ethylene (dimethylimino)ethylene dichloride]), polyquaternium-43 (i.e., copolymer of acrylamide, acrylamidopropyltrimonium chloride, 2-amidopropylacrylamide sulfonate and dimethylaminopropylamine), polyquaternium-44 (i.e., 3-methyl-1-vinylimidazolium methyl sulfate-N-vinylpyrrolidone copolymer), polyquaternium-45 (i.e., copolymer of (N-methyl-N-ethoxyglycine)methacrylate and N,N-dimethylaminoethylmethacrylate, quaternized with dimethyl sulphate), polyquaternium-46 (i.e., terpolymer of vinylcaprolactam, vinylpyrrolidone, and quaternized vinylimidazole), polyquaternium-47 (i.e., terpolymer of acrylic acid, methacrylamidopropyl trimethylammonium chloride, and methyl acrylate), polyquaternium-53 (i.e., copolymer of acrylic acid, acrylamide and methacrylamidopropyl trimonium chloride), polyquaternium-63 (i.e., polymeric quaternary ammonium salt formed by acrylamide, acrylic acid and ethyltrimonium chloride acrylate), polyquaternium-73 (i.e., polymeric quaternary ammonium salt consisting of propyltrimonium), polyquaternium-91 (i.e., quaternary ammonium salt of hydroxypropyl methacrylate and polyethylene glycol methacrylate quaternized with ethyltrimonium chloride methacrylate), guar hydroxypropyltrimonium chloride, cationic hydroxyethyl cellulose (HEC) derivatives, hydroxypropyltrimonium hydrolyzed collagen, lauryldimonium hydroxypropyl hydrolyzed collagen, cocodimonium hydroxypropyl hydrolyzed collagen, stearyltrimonium hydroxyethyl hydrolyzed collagen, stearyldimonium hydroxypropyl hydrolyzed collagen, hydroxypropyltrimonium hydrolyzed keratin, cocodimonium hydroxypropyl hydrolyzed hair keratin Cocodimonium, hydroxypropyl hydrolyzed keratin, hydroxypropyltrimonium gelatin, hydroxypropyltrimonium hydrolyzed casein, hydroxypropyltrimonium hydrolyzed wheat protein, cocodimonium hydroxypropyl hydrolyzed wheat protein, lauryldimonium hydroxypropyl hydrolyzed wheat protein, stearyldimonium hydroxypropyl hydrolyzed wheat protein, hydroxypropyltrimonium hydrolyzed soy protein, cocodimonium hydroxypropyl hydrolyzed soy protein, lauryldimonium hydroxypropyl hydrolyzed soy protein, hydroxypropyltrimonium hydrolyzed conchiolin protein, hydroxypropyltrimonium hydrolyzed rice bran protein, hydroxypropyltrimonium hydrolyzed silk protein, hydroxypropyltrimonium hydrolyzed whey protein, hydroxypropyltrimonium jojoba protein, cassia hydroxypropyltrimonium chloride, locust bean hydroxypropyltrimonium chloride, hydroxypropyltrimonium hydrolyzed wheat starch, hydroxypropyltrimonium hydrolyzed corn (maize) starch, hydroxypropyltrimonium hydrolyzed potato starch, hydroxypropyltrimonium hydrolyzed amylopectin, cocodimonium hydroxypropyloxyethyl cellulose, lauryldimonium hydroxypropyloxyethyl cellulose, stearyldimonium hydroxyethyl cellulose, stearyldimonium hydroxypropyl oxyethyl cellulose, guar hydroxypropyltrimonium chloride, and hydroxypropyl guar hydroxypropyltrimonium chloride.

The term "substrate," as used herein, refers to a rigid, solid support that can physically or chemically bond to the polycation. The substrate may be porous or non-porous. The substrate may be a bead, a rod, a tube, or may be a structure having another suitable geometry, such as one with a substantially flat surface(s) (e.g., a cube). In an example, the substrate is a patterned surface, such as a flow cell having a structure therein or thereon that increases the surface area for capturing nucleic acids. Examples of these structures include wells, posts, pillars, etc. having dimensions on the nanoscale or the microscale. In an example, the substrate is selected from the group consisting of controlled pore glass (CPG), a metal oxide, a metal with an oxide layer, and combinations thereof. Examples of suitable metal oxides include silicon dioxide (silica), aluminum oxide (alumina), titanium oxide (titania), zeolites, silicate, etc. Examples of suitable metals having an oxide layer thereon include aluminum, silicon, titanium, etc. In another example, carbon (e.g., activated carbon) may be used as the substrate. In still another example, the substrate is a magnetic bead. Examples of magnetic materials include iron oxide (e.g., magnetite, ferrite), cobalt, iron, nickel, silica coated magnetite, or polymer/magnetite blended materials (e.g., polystyrene/magnetite). The substrate may also have a core/shell structure with magnetic material in the core and a polymer shell. Still another example of a substrate include plastic materials.

When porous substrates are used, the diameter of the pores may range from about 5 nm to about 1 μm. In another example, the diameter of the pores may range from about 35 nm to about 150 nm.

The aspects and examples set forth herein and recited in the claims can be understood in view of the above definitions.

Examples of the nucleic acid extraction material and methods for making and using the same will now be described in reference to the figures.

Figure 1B:
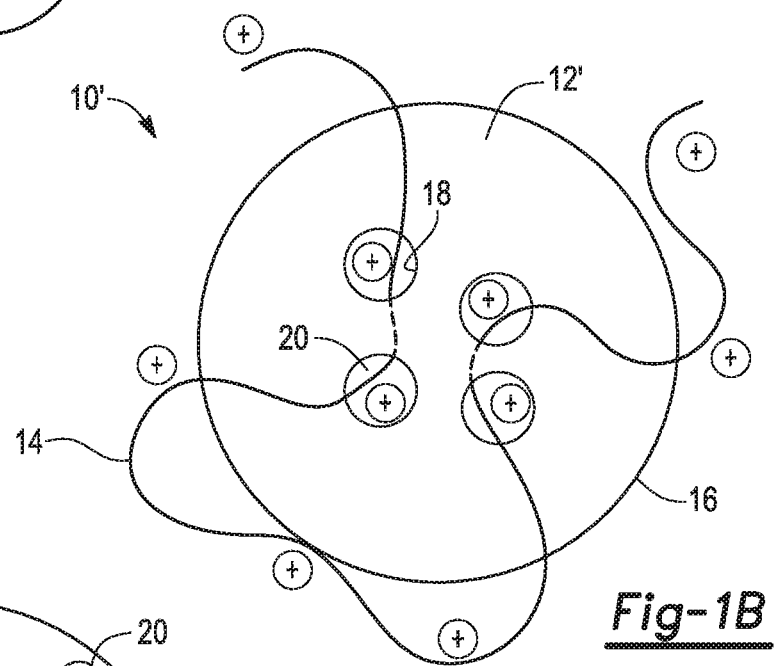
FIG. 1B is a schematic view of another example of the nucleic acid extraction material disclosed herein.
Figure 1C:
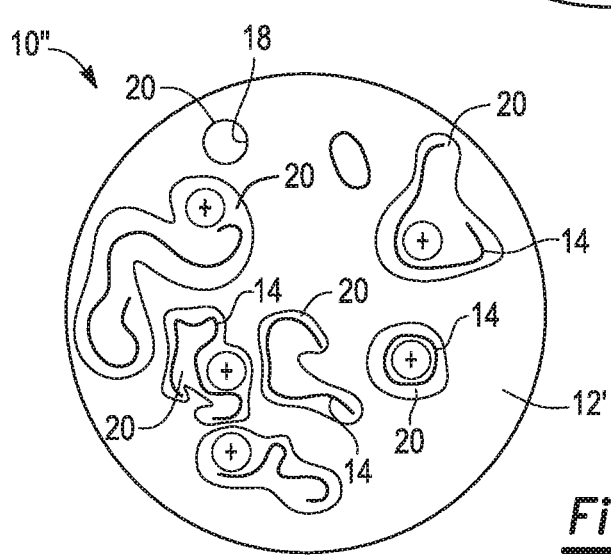
FIG. 1C is a schematic view of still another example of the nucleic acid extraction material disclosed herein.

FIGS. 1A through 1C illustrate different examples of the nucleic acid extraction material 10, 10', 10". Each of the nucleic acid extraction materials 10, 10', 10" includes a substrate 12 or 12' and a polycation 14 bonded to at least a portion of a surface of the substrate 12 or 12'.

The example shown in FIG. 1A illustrates a non-porous substrate 12 and the polycation 14 bonded to portion(s) of an exterior surface 16 of the non-porous substrate 12. The non-porous substrate 12 is a support with a solid or hollow core that does not include any pores 20 (shown in FIGS. 1B and 1C). Examples of the non-porous substrate 12 include silicon dioxide (silica), aluminum oxide (alumina), titanium oxide (titania), metals with an oxide layer, or magnetic materials (e.g., iron oxide (e.g., magnetite, ferrite), cobalt, iron, nickel, silica coated magnetite, polymer/magnetite blended materials (e.g., polystyrene/magnetite)). The non-porous substrate 12 may also have a core/shell structure, e.g., with a magnetic core and a polymer shell.

In FIG. 1A, the polycation 14 may form a continuous or non-continuous coating on the exterior surface 16 of the non-porous substrate 12. In this example, a continuous coating is formed when the polycation 14 covers the entire exterior surface 16 of the non-porous substrate 12. In this example, a non-continuous coating is formed when the polycation 14 covers some, but not all, of the exterior surface 16 of the non-porous substrate 12. As such, with this non-continuous coating, portion(s) of the exterior surface 16 are exposed.

The examples shown in FIGS. 1B and 1C illustrate a porous substrate 12', where the substrate 12' includes a plurality of pores 20. In these examples, the surface to which the polycation 14 is bonded is the exterior surface 16, an interior pore surface 18, or combinations thereof. In the example shown in FIG. 1B, the polycation 14 is bonded to portion(s) of the exterior surface 16 and portion(s) of the interior pore surfaces 18 of the porous substrate 12'. In the example shown in FIG. 1C, the polycation 14 is bonded to portion(s) of the interior pore surfaces 18, but not to the exterior surface 16 of the porous substrate 12'.

The porous substrate 12' is a support that includes pores 20 located throughout its core and/or at its exterior surface 16. The pores 20 may be interconnected, and thus one pore 20 may have an opening that leads to another pore 20. Each pore 20 has an interior pore surface 18. Examples of the porous substrate 12' include controlled pore glass (CPG), porous silica (e.g., fumed silica), porous metal oxides (e.g., anodized aluminum oxide, porous titanium oxide, etc.), as well as porous plastic materials (e.g., porous plastic membranes). When the porous substrate 12' is used, it may be desirable for each of the pores 20 to have a diameter that is smaller than a diameter of a cell (e.g., white blood cells containing gDNA) in a whole blood sample. When the polycation 14 is confined to the interior pore surfaces 18, as shown in FIG. 1C, this pore size prevents the white blood cells in the whole blood sample from contacting the polycation 14 when the nucleic acid extraction material 10" is exposed to the whole blood sample.

In FIG. 1B, the polycation 14 may form a continuous or non-continuous coating on the exterior surface 16 and on the interior pore surfaces 18 of the porous substrate 12'. In this example, a continuous coating is formed when the polycation 14 covers the entire exterior surface 16 and each of the interior pore surfaces 18. In this example, a non-continuous coating is formed when the polycation 14 covers some, but not all, of the exterior surface 16. As such, with this non-continuous coating, portion(s) of the exterior surface 16 are exposed.

In FIG. 1C, the polycation 14 may form a continuous or non-continuous coating on the interior pore surfaces 18 of the porous substrate 12'. In this example, a continuous coating is formed when the polycation 14 covers each of the interior pore surfaces 18. In this example, a non-continuous coating is formed when the polycation 14 covers some, but not all, of the interior pore surfaces 18. As such, with this non-continuous coating, portion(s) of the interior pore surfaces 18 are exposed.

In the examples shown in FIGS. 1A through 1C, the polycation 14 may be a polymer or a copolymer. The polymer may be a polymerized, quaternized monomer selected from the group consisting of a quaternized 1-vinylimidazole monomer and a quaternized dimethylaminoethyl methacrylate monomer. The copolymer may be a copolymer of a neutral monomer and a quaternized monomer selected from the group consisting of a quaternized 1-vinylimidazole monomer and a quaternized dimethylaminoethyl methacrylate monomer.

In an example, the neutral monomer is an N-vinylpyrrolidone monomer, such as 1-vinyl-2-pyrrolidone (i.e., 1-ethenyl-2-pyrrolidinone). 1-vinyl-2-pyrrolidone has the following structure:

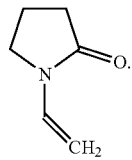

Other suitable neutral monomers include acrylamide or hydroxypropylmethacrylamide.

In an example, the quaternized 1-vinylimidazole monomer is 3-alkyl-1-vinylimidazolium counterion ($X^-$), where the alkyl (R) is any alkyl group having from 1 carbon atom to 10 carbon atoms, and where the counterion ($X^-$) is chloride, methyl sulfate, ethyl sulfate, iodide, sulfate, acetate, bromide, etc. A general structure of the quaternized 1-vinylimidazole monomer is:

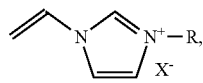

(where R is any alkyl group having from 1 carbon atom to 10 carbon atoms and $X^-$ is any of the previously listed counterions). A specific example of this monomer includes 3-methyl-1-vinylimidazolium chloride (which may also be referred to as 1-ethenyl-3-methyl chloride).

The quaternized dimethylaminoethyl methacrylate (DMAEMA) monomer has the following structure:

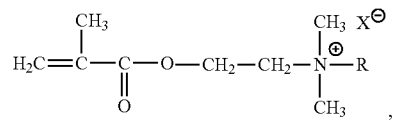

where R is any alkyl group having from 1 carbon atom to 10 carbon atoms and $X^-$ is any of the previously listed counterions.

In an example, the polycation 14 is a cationic copolymer including about 50% of the quaternized 1-vinylimidazole monomer and about 50% of the neutral N-vinylpyrrolidone monomer. In an example, the quaternized 1-vinylimidazole monomer is 3-methyl-1-vinylimidazolium chloride and the neutral N-vinylpyrrolidone monomer is 1-vinyl-2-pyrrolidone. This cationic copolymer is commercially available from BASF Corp. under the tradename LUVIQUAT® FC 550 (polyquaternium-16, also known as 1-ethenyl-3-methyl-1H-imidazolium chloride polymer with 1-ethenyl-2-pyrrolidinone, or 3-methyl-1-vinylimidazolium chloride-1-vinyl-2-pyrrolidinone copolymer). The charge density LUVIQUAT® FC 550 is about 3.3 meq/g and the molecular weight is about 80,000 g/mol. In other examples with these percentages of the monomers, the quaternized 1-vinylimidazole monomer is 3-methyl-1-vinylimidazolium methyl sulfate and the neutral N-vinylpyrrolidone monomer is 1-vinyl-2-pyrrolidone. In still other examples with these percentages of the monomers, the quaternized 1-vinylimidazole monomer is 3-ethyl-1-vinylimidazolium ethyl sulfate and the neutral N-vinylpyrrolidone monomer is 1-vinyl-2-pyrrolidone.

In another example, the polycation 14 is a cationic copolymer including about 30% of the quaternized 1-vinylimidazole monomer and about 70% of the neutral N-vinylpyrrolidone monomer. In an example, the quaternized 1-vinylimidazole monomer is 3-methyl-1-vinylimidazolium chloride and the neutral N-vinylpyrrolidone monomer is 1-vinyl-2-pyrrolidone. This cationic copolymer is commercially available from BASF Corp. under the tradename LUVIQUAT® FC 370 (polyquaternium-16). The charge density LUVIQUAT® FC 370 is about 2.0 meq/g and the molecular weight is about 100,000 g/mol. In other examples with these percentages of the monomers, the quaternized 1-vinylimidazole monomer is 3-methyl-1-vinylimidazolium methyl sulfate and the neutral N-vinylpyrrolidone monomer is 1-vinyl-2-pyrrolidone. In still other examples with these percentages of the monomers, the quaternized 1-vinylimidazole monomer is 3-ethyl-1-vinylimidazolium ethyl sulfate and the neutral N-vinylpyrrolidone monomer is 1-vinyl-2-pyrrolidone.

In still another example, the polycation 14 is a cationic copolymer including about 95% of the quaternized 1-vinylimidazole monomer and about 5% of the neutral N-vinylpyrrolidone monomer. In an example, the quaternized 1-vinylimidazole monomer is 3-methyl-1-vinylimidazolium chloride and the neutral N-vinylpyrrolidone monomer is 1-vinyl-2-pyrrolidone. This cationic copolymer is commercially available from BASF Corp. under the tradename LUVIQUAT® Excellence (polyquaternium-16). The charge density LUVIQUAT® Excellence is about 6.1 meq/g and the molecular weight is about 40,000 g/mol. In other examples with these percentages of the monomers, the quaternized 1-vinylimidazole monomer is 3-methyl-1-vinylimidazolium methyl sulfate and the neutral N-vinylpyrrolidone monomer is 1-vinyl-2-pyrrolidone. In still other examples with these percentages of the monomers, the quaternized 1-vinylimidazole monomer is 3-ethyl-1-vinylimidazolium ethyl sulfate and the neutral N-vinylpyrrolidone monomer is 1-vinyl-2-pyrrolidone.

In yet another example, the polycation 14 is a cationic copolymer including about 33% of the quaternized dimethylaminoethyl methacrylate monomer (with any of the listed counterions and R groups) and about 67% of the neutral N-vinylpyrrolidone monomer. In an example, the counter ion is chloride and the neutral N-vinylpyrrolidone monomer is 1-vinyl-2-pyrrolidone. In an example, the counter ion is ethylsulfate, the R group is ethyl and the neutral N-vinylpyrrolidone monomer is 1-vinyl-2-pyrrolidone. This cationic copolymer is commercially available from BASF Corp. under the tradename LUVIQUAT® PQ11 AT (polyquaternium-11), and has the following structure (where x represents about 67% of the copolymer and y represents about 33% of the copolymer):

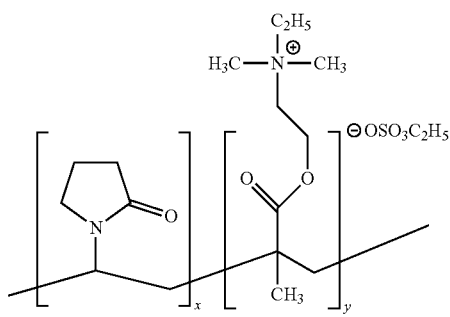

The charge density LUVIQUAT® PQ11 AT is about 0.8 meq/g and the molecular weight is about 1,000,000 g/mol. In other examples with these percentages of the monomers, the counterion may be methyl sulfate or ethyl sulfate.

When whole blood is the sample from which the cfNA is being extracted, any of the previously mentioned polycations 14 may be used. It is believed that when extracting cfNA from whole blood, other polycations 14 may also be capable of selectively capturing the cfNA and subsequently releasing the cfNA. Examples of these other suitable polycations 14 may include polyquaternium-10, polyquaternium-14, polyquaternium-17, polyquaternium-18, polyquaternium-19, polyquaternium-20, polyquaternium-24, polyquaternium-28, polyquaternium-29, polyquaternium-32, polyquaternium-33, polyquaternium-34, polyquaternium-35, polyquaternium-36, polyquaternium-37, polyquaternium-39, polyquaternium-42, polyquaternium-43, polyquaternium-44, polyquaternium-45, polyquaternium-46, polyquaternium-47, polyquaternium-53, polyquaternium-63, polyquaternium-73, polyquaternium-91, guar hydroxypropyltrimonium chloride, cationic hydroxyethyl cellulose (HEC) derivatives, hydroxypropyltrimonium hydrolyzed collagen, lauryldimonium hydroxypropyl hydrolyzed collagen, cocodimonium hydroxypropyl hydrolyzed collagen, stearyldimonium hydroxyethyl hydrolyzed collagen, stearyldimonium hydroxypropyl hydrolyzed collagen, hydroxypropyltrimonium hydrolyzed keratin, cocodimonium hydroxypropyl hydrolyzed hair keratin Cocodimonium, hydroxypropyl hydrolyzed keratin, hydroxypropyltrimonium gelatin, hydroxypropyltrimonium hydrolyzed casein, hydroxypropyltrimonium hydrolyzed wheat protein, cocodimonium hydroxypropyl hydrolyzed wheat protein, lauryldimonium hydroxypropyl hydrolyzed wheat protein, stearyldimonium hydroxypropyl hydrolyzed wheat protein, hydroxypropyltrimonium hydrolyzed soy protein, cocodimonium hydroxypropyl hydrolyzed soy protein, lauryldimonium hydroxypropyl hydrolyzed soy protein, hydroxypropyltrimonium hydrolyzed conchiolin protein, hydroxypropyltrimonium hydrolyzed rice bran protein, hydroxypropyltrimonium hydrolyzed silk protein, hydroxypropyltrimonium hydrolyzed whey protein, hydroxypropyltrimonium jojoba protein, cassia hydroxypropyltrimonium chloride, locust bean hydroxypropyltrimonium chloride, hydroxypropyltrimonium hydrolyzed wheat starch, hydroxypropyltrimonium hydrolyzed corn (maize) starch, hydroxypropyltrimonium hydrolyzed potato starch, hydroxypropyltrimonium hydrolyzed amylopectin, cocodimonium hydroxypropyloxyethyl cellulose, lauryldimonium hydroxypropyloxyethyl cellulose, stearyldimonium hydroxyethyl cellulose, stearyldimonium hydroxypropyl oxyethyl cellulose, guar hydroxypropyltrimonium chloride, and hydroxypropyl guar hydroxypropyltrimonium chloride.

The polycation 14 is bonded to the substrate 12 or 12'. In some examples, the polycation 14 may be physically bonded or chemically bonded to the substrate 12 or 12'. The type of bond that forms depends upon the interaction between the substrate 12, 12' and the polycation 14, and thus depends upon the material selected for each of these components 12, 12' and 14. As an example, some of the polycations 14 (e.g., the various examples of polyquaternium-16) are electrostatically attracted to some of the substrates 12, 12' (e.g., controlled pore glass), and thus spontaneously absorb to the substrate 12, 12' and form a physical bond between the polycation 14 and the substrate 12, 12'. This example of physical bonding may be referred to a physisorption. Other non-covalent interactions may bond the polycation 14 and the substrate 12, 12'. For example, the substrate 12, 12' may contain or be modified to contain streptavidin, which is capable of non-covalently bonding with biotin attached to the polycation 14. Alternatively, the substrate 12, 12' may contain or be modified to contain surface groups that are capable of chemically bonding, e.g., via covalent bonding, with pendant group(s) and/or end group(s) of the polycation 14. Examples of suitable surface groups include silane coupling agents or other organic linking molecules.

As an example, a polymerizable group (e.g., methacrylamidopropyltrimethoxysilane) may be linked to the substrate surface 16 and/or 18, and the monomer (e.g., vinylimidazoleum chloride) may be polymerized (in the presence of the modified substrate) to form the polycation 14. As another example, a chain transfer agent (e.g., thiol) may be linked to the substrate surface 16 and/or 18 (e.g., mercaptopropyltrimethoxysilane) and then the cationic monomer may be polymerized in the presence of the modified substrate to form the polycation 14. As yet another example, the substrate 12, 12' may be coated with benzophenone. UV light may be used to generate radicals, which results in coupling of polycation 14 to the surface. In still other examples, the polycation 14 may contain or be modified to contain surface groups that are capable of covalently bonding with surface groups of the substrate 12, 12'. For example, the polycation 14 may be modified to include amine functional groups, which can react with epoxysilane surface groups on the substrate 12, 12'. In still further examples, an initiator may be linked to the substrate surface 16 and/or 18, and then the cationic monomer may be polymerized from the surface 16 and/or 18. In yet further examples, the polycation 14 may be prepared by polymerizing the neutral monomer (e.g., 1-vinyl imidazole) and then bonding the neutral polymer to the substrate 12, 12', which is followed by quaternization of the quaternizable monomer residues within the neutral polymer.

Figure 2:
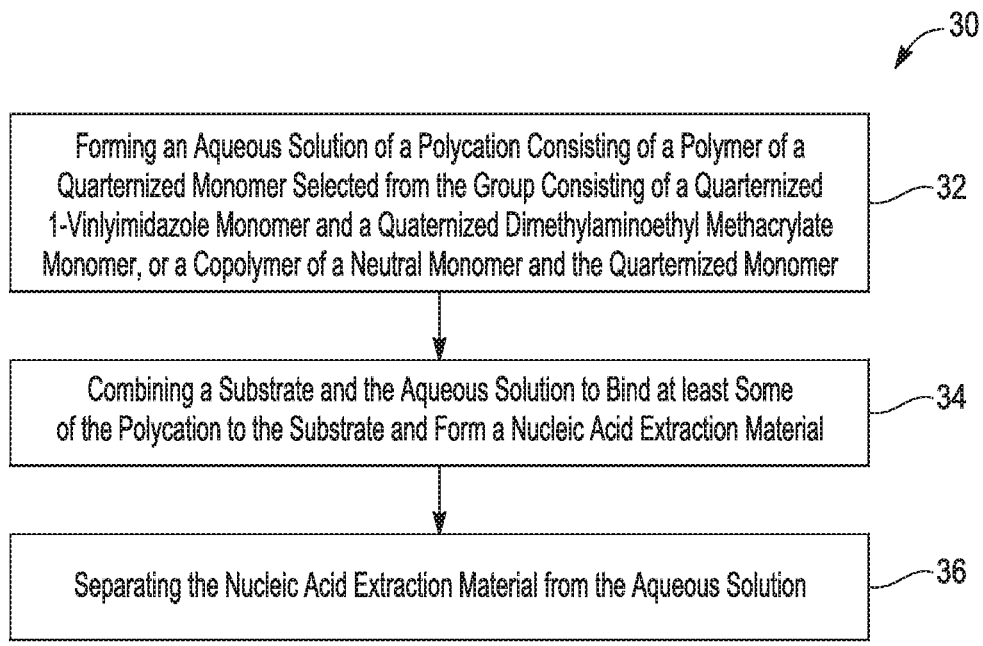
FIG. 2 is a flow diagram illustrating an example of a method disclosed herein.

Referring now to FIG. 2, an example of a method 30 for forming examples of the nucleic acid extraction material 10 and 10' is depicted. As illustrated, the method 30 includes forming an aqueous solution of a polycation 14 consisting of a polymer of a quaternized monomer selected from the group consisting of a quaternized 1-vinylimidazole monomer and a quaternized dimethylaminoethyl methacrylate monomer, or a copolymer of a neutral monomer and the quaternized monomer (as shown at reference numeral 32); combining a substrate 12 or 12' and the aqueous solution to bind at least some of the polycation 14 to the substrate 12 or 12' and form a nucleic acid extraction material 10 or 10' (as shown at reference numeral 34); and separating the nucleic acid extraction material 10 or 10' from the aqueous solution (as shown at reference numeral 36).

Any of the polycations 14 described herein, which include the polymer of the quaternized 1-vinylimidazole monomer or the quaternized dimethylaminoethyl methacrylate monomer or the copolymer of the neutral monomer and the quaternized vinylimidazole monomer or the quaternized dimethylaminoethyl methacrylate monomer, may be selected. As an example involving the copolymer, the neutral monomer may be N-vinylpyrrolidone the method 30 may include selecting the polycation 14 from the group consisting of i) the cationic copolymer including about 50% of the quaternized 1-vinylimidazole monomer and about 50% of the N-vinylpyrrolidone, ii) the cationic copolymer including about 30% of the quaternized 1-vinylimidazole monomer and about 70% of the N-vinylpyrrolidone, iii) the cationic copolymer including about 95% of the quaternized 1-vinylimidazole monomer and about 5% of the N-vinylpyrrolidone, and iv) the cationic copolymer including about 33% of the quaternized dimethylaminoethyl methacrylate monomer and about 67% of the N-vinylpyrrolidone.

This polycation 14 may be combined with water to generate the aqueous solution including from about 0.001 wt % to about 10 wt % of the polycation 14 (based on the total wt % of the aqueous solution). The aqueous solution of the polycation 14 may also be commercially available (e.g., the LUVIQUAT® series previously mentioned herein). In an example, the aqueous solution is a 1% solution of the polycation 14 in water.

The substrate 12 or 12' is then combined with the aqueous solution. From about 2 g to about 3 g of the substrate 12 or 12' may be combined with from about 150 mL to about 250 mL of the 1% solution of the polycation 14 in water. As an example, about 2.8 g of the substrate 12 or 12' may be combined with about 200 mL of the 1 solution of the polycation 14 in water. It is to be understood that the amount of the substrate 12 or 12' may depend, in part, on the type of polycation 14 and/or substrate 12 or 12' used, the concentration of the polycation 14, and/or the volume of the aqueous solution. The amount of polycation 14 used may depend, in part, on the surface area of the substrate 12 or 12' and the time used for incubation. The combination may then be shaken, stirred, or otherwise mixed, either manually or via an automated process. The combination of the substrate 12 or 12' and the aqueous solution may then be allowed to incubate for a suitable time period to form the nucleic acid extraction material 10 or 10', before separating the nucleic acid extraction material 10 or 10' from the remaining aqueous solution. In an example, the time period ranges from about 30 minutes to about 72 hours (3 days). In another example, the time period ranges from about 4 hours to about 72 hours. In still another example, the time period ranges from about 30 minutes to about 60 minutes. During this period, at least some of the polycation 14 binds to at least some of the surface(s) 16 and/or 18 of the substrate 12 or 12'. The time period may be longer or shorter depending upon the bonding that is taking place between the substrate 12 or 12' and the polycation 14.

The nucleic acid extraction material 10 or 10' may then be separated from the remaining aqueous solution. Separation may involve pouring off the aqueous solution (e.g., when the 10, 10' have settled in the solution), filtering, using a magnet (e.g., when magnetic beads are used as the substrate 12, 12'), or the like.

In some examples, the separated nucleic acid extraction material 10 or 10' may then be dried. Drying may take place via evaporation, under vacuum, via supercritical drying, lyophilization, or via heating through conduction, convection, or radiation. As examples, drying may take place in a conduction oven or convection oven, or under a radiation lamp. The drying temperature may range from room temperature (from about 18° C. to about 22° C.) to about 120° C. In an example, the nucleic acid extraction material 10 or 10' may be dried at a temperature of about 60° C. for a time period ranging from about 2 hours to about 20 hours. In other examples of the method, drying is not performed.

The nucleic acid extraction material 10' (with the porous substrate 12') may be used to form the nucleic acid extraction material 10". To form the nucleic acid extraction material 10", the method 30 may also involve polishing the exterior surface 16 of the nucleic acid extraction material 10' to remove at least some of the polycation 14 from the exterior surface 16 of the porous substrate 12'. The polishing may be gentle enough to leave at least some of the polycation 14 bonded to the interior pore surfaces 18. The polycation 14 may be polished off by using a stirring process (e.g., stirring on a stir plate with a magnetic stir bar). Removal of the polycation 14 from the exterior surface 16 may also involve grinding, e.g., using a media mill.

Removing the polycation 14 from the exterior surface 16 may be desirable so that the polycation 14 is located in recessed areas (i.e., interior pore surfaces 18) of the nucleic acid extraction material 10". When the diameter of the pores 20 is smaller than the diameter the cells in the whole blood sample to which the nucleic acid extraction material 10" is exposed, the cells are unable to contact the polycation 14 contained on the interior pore surfaces 18. This may be desirable to ensure that the cells do not lyse.

While not shown in FIG. 2, the nucleic acid extraction material 10, 10', 10" may also be washed/rinsed prior to being used for cfNA capture from a whole blood sample. This may be performed to remove any unbound polycation 14. One rinse or several rinses may be performed. Suitable rinsing liquids include water or a combination of water and phosphate buffered saline (PBS) (e.g., at a concentration of 0.137 M NaCl, and 10 mM phosphate, and 2.7 mM KCl).

Also while not shown in FIG. 2, it is to be understood that the method 30 may also be performed with the other examples of the polycation 14 disclosed herein.

It is to be further understood that other methods may be used to make the nucleic acid extraction materials 10, 10', 10". As an example, the polycation 14 may be formed in situ in the presence of the substrate 12 or 12'. Monomers capable of reacting to form the polycation 14 may be mixed with the substrate 12 or 12', and polymerization may be initiated in a manner suitable for the monomers. As previously mentioned herein, initiators, linking groups, chain transfer agents, etc. may be used to aid in the in situ polymerization of the polycation 14. In this example, the polycation 14 will form and will bond with at least some of the exposed surface(s) 16 and/or 18 of the substrate 12 or 12' to respectively form the nucleic acid extraction material 10 or 10'. The nucleic acid extraction material 10' formed by this method may then be exposed to polishing or grinding to remove the polycation 14 from the exterior surface 16 and to form the nucleic acid extraction material 10".

Figure 3:
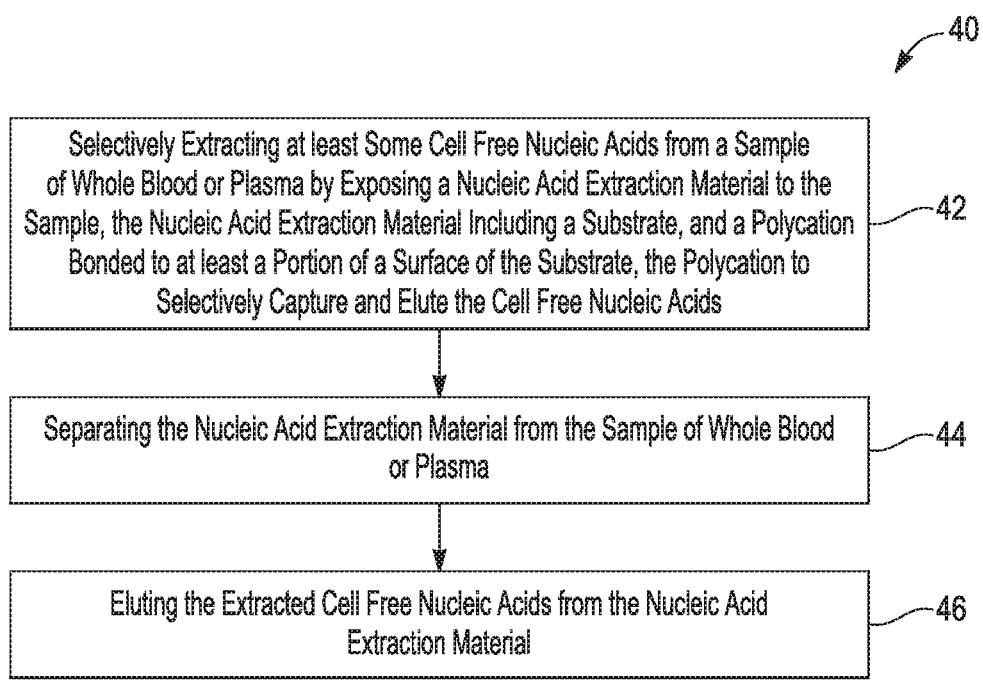
FIG. 3 is a flow diagram illustrating another example of a method disclosed herein.

Referring now to FIG. 3, an example of a method 40 for using examples of the nucleic acid extraction material 10, 10', 10" is depicted. As illustrated, the method 40 includes selectively extracting at least some cell free nucleic acids from a sample of whole blood or plasma by exposing a nucleic acid extraction material 10, 10', 10" to the sample, the nucleic acid extraction material including a substrate 12 or 12' and a polycation 14 bonded to at least a portion of a surface 16 and/or 18 of the substrate 12 or 12', the polycation 14 to selectively capture and elute the cell free nucleic acids (as shown at reference numeral 42); separating the nucleic acid extraction material 10, 10', 10" from the sample of whole blood or plasma (as shown at reference numeral 44); and eluting the extracted cell free nucleic acids from the nucleic acid extraction material 10, 10', 10" (as shown at reference numeral 46).

In the example method 40, human whole blood samples may be used, and any example of the polycation 14 disclosed herein may be used. In an example, the polycation is the one of the cationic copolymers including the quaternized 1-vinylimidazole monomer and the neutral N-vinylpyrrolidone monomer.

Exposure of the nucleic acid extraction material 10, 10', 10" to the whole blood or plasma sample may take place in any suitable container (e.g., a non-stick container). The nucleic acid extraction material 10, 10', 10" and the whole blood or plasma sample may be introduced to the container sequentially or simultaneously. The container may be sealed and inverted for a predetermined time period, allowing the nucleic acid extraction material 10, 10', 10" to settle within the container. In an example, the predetermined time prior ranges from about 15 minutes to about 30 minutes, but may be longer or shorter. During exposure, the polycation 14 of the nucleic acid extraction material 10, 10', 10" extracts at least some cell free nucleic acids from the sample of whole blood.

The blood or plasma sample may then be removed from the container using any suitable technique, such as pipetting, pouring, filtration, etc. When using pipetting or pouring, it is to be understood that it may be desirable to allow the nucleic acid extraction material 10, 10', 10" to settle in the container prior to removing the blood sample. The nucleic acid extraction material 10, 10', 10" having the cfNA thereon may be rinsed using a suitable buffer until the rinsate is colorless and/or transparent. The rinsate is then removed from the nucleic acid extraction material 10, 10', 10" having the cfNA thereon using any of the removal techniques described herein.

The cfNA may then be eluted from the nucleic acid extraction material 10, 10', 10". Elution of the cfNA may involve exposing the nucleic acid extraction material 10, 10', 10" to a material that separates the cfNA from the surface 16 and/or 18. One example of this material is in an elution buffer. Suitable elution buffers include salt solutions, such as phosphate buffered saline (PBS), or solutions of chaotropic salts, e.g., sodium trichloroacetate ($Cl_3CCOONa$), guanidinium hydrochloride, guanidinium thiocyanate, sodium bromide (NaBr), sodium acetate, and sodium chloride (NaCl). Other suitable salts may also include lithium or potassium salts. In general, the concentration of these salt solutions should be sufficiently high to break electrostatic interactions between the captured nucleic acids and the substrate 12 or 12'. For example, typical concentrations range from about 0.4 M to about 5 M, or in some examples, from about 0.5 M to about 2.5 M. In an example, eluting involves exposing the separated nucleic acid extraction material 10, 10', 10" (having the cfNA thereon) to the elution buffer including the salt. The salt solution (or other elution buffer) may disrupt the bonds that hold the cfNA to the polycation 14. In some instances, it may be desirable to heat up the elution buffer and to let the nucleic acid extraction material 10, 10', 10" incubate for some predetermined time in order to release more cfNA molecules. For example, phosphate buffered saline (PBS) may be added to the nucleic acid extraction material 10, 10', 10" having the cfNA thereon, and this combination may be mixed and incubated at a predetermined temperature for a predetermined time.

It may also be beneficial to add a surfactant to the elution buffer to aid in elution or in subsequent steps, such as protein removal. Examples of suitable surfactants include anionic surfactants, such as sodium dodecyl sulfate (SDS), or non-ionic surfactants, such as TWEEN® or TRITON™ X-100 (having a hydrophilic polyethylene oxide chain and an aromatic hydrocarbon lipophilic or hydrophobic group). A suitable amount of surfactant may range from about 0.001 wt % to about 2 wt % of a total wt % of the elution buffer.

The eluted cfNA (e.g., cfDNA and/or cfRNA) may be removed from the nucleic acid extraction material 10, 10', 10". The eluted cfNA may be exposed to one or more additional processes, such as protein removal, purification, etc.

Using the method 40, the isolated cfNA sample has little or no genomic nucleic acids (e.g., gDNA and/or gRNA). The cfNA may then be used in genotyping, polymerase chain reaction (PCR), sample preparation for DNA sequencing, library preparation for DNA sequencing, or other assays. As other examples, the cfNA may be used in medical diagnostic applications, such as non-invasive prenatal testing and the detection of cancer.

Moreover, the nucleic acid extraction material 10, 10', 10" disclosed herein may increase isolated cfDNA yield from whole blood samples anywhere from 2× (2 times) more to about 4.5× more (when compared to some commercial kits used to isolate cfDNA from plasma), and from plasma samples anywhere from 1.5× more to about 5× more (when compared to some commercial kits used to isolate cfDNA from plasma). In an example, the nucleic acid extraction material 10, 10', 10" disclosed herein may increase isolated cfDNA yield from whole blood samples anywhere from about 1.5× more to about 2× more when compared to Bioo Scientific Next Prep used to isolate cfDNA from whole blood samples.

This disclosure also provides methods and systems that extract nucleic acids, such as deoxyribonucleic acids (DNA) and ribonucleic acids (RNA) from samples. While the disclosure may describe implementations that perform DNA manipulation, it should be understood that these implementations may be used with other nucleic acids, such as RNA, and thus, are not limited to DNA. Moreover, while implementations may describe extraction of DNA from bacterial cells or blood samples, it should be understood that these implementations may be used to extract nucleic acids from other biological samples, such as human tissues or cells, animal tissues or cells, eukaryotic cells, agricultural samples, environmental samples, and other samples containing nucleic acids, with the appropriate modifications to the methods and/or systems.

As mentioned herein, certain samples collected from human tissue, animal tissue, environmental, or other samples may contain cell free nucleic acids. These cell free nucleic acids may be employed to identify specific diseases and/or biological conditions that may be associated in the collected sample. For example, cell free DNA obtained in environmental samples may be used to identify the presence of organisms in the sample. In a different example, cell free DNA obtained from animal or human tissue may be used to identify potential for genetic anomalies that may be associated with disease or some other physiological state, or characterize the stage for certain diseases. In example situations, cell free DNA obtained from pregnant animals or humans may be used to identify presence of genetic characteristics in the fetus. In another example, in some cancer patients, the presence of cell free DNA may be associated with specific cancer stages.

In the process of obtaining cell free DNA from tissue, it may be desired to avoid or reduce contamination from other DNA sources. For example, a human blood sample may have genomic or plasmid DNA from blood borne human cells (e.g., white blood cells), pathogens, and viruses in addition to the cell-free DNA of interest (e.g., fetal cell-free DNA). Some examples of the systems and methods described herein allow for extraction of cell free DNA with reduced contamination from other sources. In some implementations, reduction of contamination may be accomplished by reducing damage to cells in the samples during the extraction process. In some implementations, discrimination of DNA based on size (e.g., DNA molecular size) may be employed to separated cell free DNA from genomic or plasmid DNA.

Other samples collected from human tissue, animal tissue, or other environmental samples may have microbial communities. In order to understand ecological processes or to study diseases related to these samples, it may be useful to study certain nucleic acids of interest (e.g., DNA and/or RNA) of the microbial cells present in the communities. For example, DNA collected from these samples may be used to identify the organisms present in the sample, and calculate their concentrations in the community. In other situations, it may be possible to analyze specific biochemical capabilities of a bacterial community by identifying particular sequences associated with an enzyme and/or phenotype. For example, it may be possible to identify presence of antibacterial resistance and/or virulence factors in bacterial in a sample.

A process to obtain purified DNA may improve efficiency and reliability of analysis performed with these samples. Purification of DNA may employ at least two operations: a first operation in which nuclear membranes, cell membranes and/or cell walls may be disrupted to release intracellular material containing DNA, and a second operation in which DNA is separated and purified from the intracellular material sample. Some implementations described herein include methods and systems for processing that perform both the release of intracellular material from cells (i.e., extraction) and the separation and purification of the DNA (i.e., separation). These methods and systems enable pure DNA to be obtained from environmental samples with little or minor direct intervention from an operator. In certain implementations, the extraction process and the separation process may be performed at least partially simultaneously.

With the foregoing in mind, FIG. 1 illustrates a view of a process 100 that may be used to collect nucleic acids from samples 102. A sample 102 may be collected from any desired donor or source, such as from human tissue 104. For example, samples may be collected from a blood sample, fecal matter, or a urine sample. Samples collected from human tissue 104 may also be from tissue that is obtained from swabbing of the mouth, throat, genital areas or other exposed or available areas. Furthermore, human tissue 104 may also be collected from biopsy procedures of the respiratory system, digestive system, urinary tract, and other body parts or systems that may be of clinical or research interest.

In some situations, sample 102 may be obtained from an animal sample 106. For veterinary applications, animal sample 106 may be obtained from collection of blood, urine or fecal matter, for example. An animal sample 106 may also be obtained from swabbing accessible regions of the animal or through biopsy of tissues that may not be directly accessed. Am animal sample 106 may be collected from the respiratory system, the digestive system, urinary tract, reproductive system, or any other system, organ, or tissue that may have interest for treatment, research, or more efficient use of animal work or animal products.

Sample 102 may also be an environmental sample 108. An environmental sample 108 may include samples collected from an ecological system such as a river, a pond, a sea, a lake, or any other body of water. An environmental sample 108 may also be collected from soil, a swamp, the air, or any other environment having microorganisms of interest.

Other sources 110 may also provide useful samples 102. For example, the samples 102 may originate from equipment, facilities and/or environments built by humans, such as waste water treatment facilities, landfills, mining areas, HVAC equipment, and other areas where cell free DNA may be present in samples 102 or where study of microorganisms may be useful. Suitable samples 102 containing cell free DNA may have a wide concentration ranging from about 0.01 ng/ml to over about 5000 ng/ml, for example. Suitable samples containing microbial communities may have a wide concentration ranging from about 10 cells/ml to about 1010 cells/ml, for example.

Sample 102 collected as described above may undergo a preprocessing 120 that may remove debris and other impurities that may interfere with process 100. Preprocessing 120 may produce a prepared sample 122. Preprocessing 120 may be performed via filtering, sedimentation, or any other process that separates, in some examples, supernatant containing nucleic acids from other debris in sample 102, or, in other examples, microbial or cellular populations of interest from non-cellular matter. In some situations, preprocessing 120 may include simple filtration or centrifugation. For certain types of samples 102, preprocessing 120 may include operations to add reagents to improve stability of the sample 102, of DNA in the sample 102, or to otherwise improve the efficiency the process 100.

An extraction process 124 may be performed on the prepared sample 122 to produce nucleic acids 126.

In some examples, the extraction process 124 may separate the nucleic acids 126 from other matter, such as free proteins, cells, free lipids, suspended particles, and other non-DNA material. Moreover, in some examples, the nucleic acids 126 obtained via extraction process 124 may be substantially composed by cell free nuclei acid. To this end, extraction process 124 may rely on a size discrimination technique (e.g., filtering, gel separation, electrophoresis) to separate the DNA based on the source (e.g., cell free DNA, viral DNA, genomic DNA). Implementations described herein may lead to cell free DNA having concentrations ranging from about 2 ng/ml to over about 5000 ng/ml.

In other examples, the extraction process 124 may release intracellular material into the solvent by lysing (e.g., breaking, dissolving, disrupting) cell walls, cell membranes and/or nuclear membranes in eukaryotic cells. This extraction process 124 may also separate DNA from the debris released from the cell that may include lipids, proteins, lipoproteins, other nucleic acids, and other non-DNA material.

In any example of the extraction process 124, other nucleic acids (e.g., RNA) may also be extracted by the process 100, in some instances with the appropriate adjustments to the process 100. The process 100 may be implemented in a streamlined manner for quickly and automatically obtaining the desired material, without human handling of the sample and/or minor user intervention with the system performing the process 100.

Figure 5A:
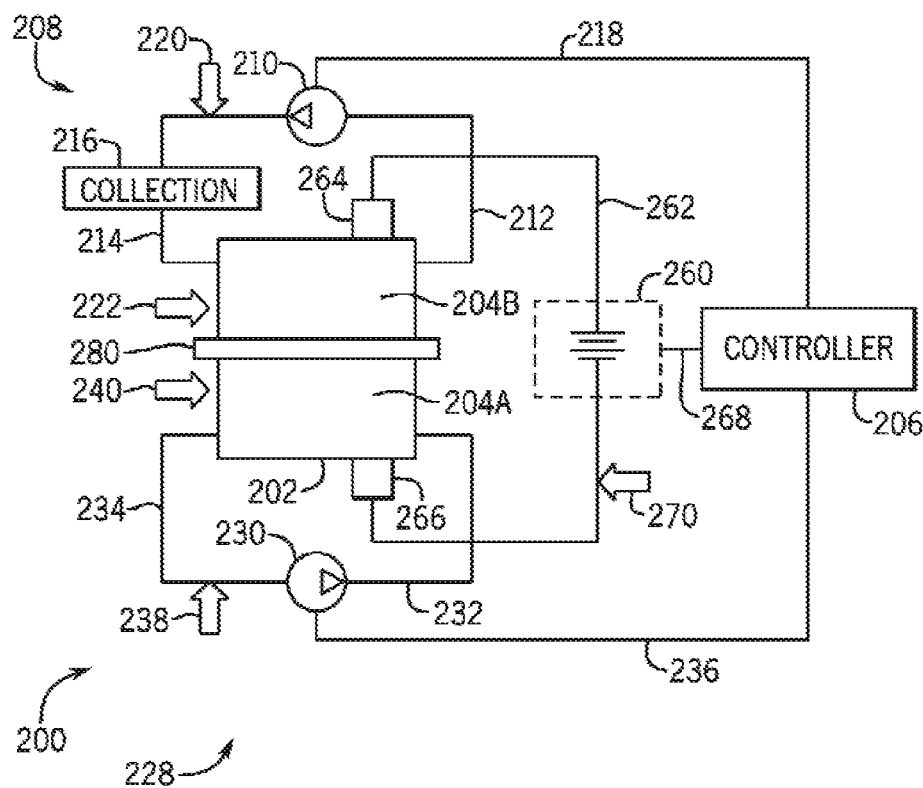
FIG. 5A illustrates an example of a system that allows extraction of cell free nucleic acids from samples that may be used in the application illustrated in FIG. 4.
Figure 5B:
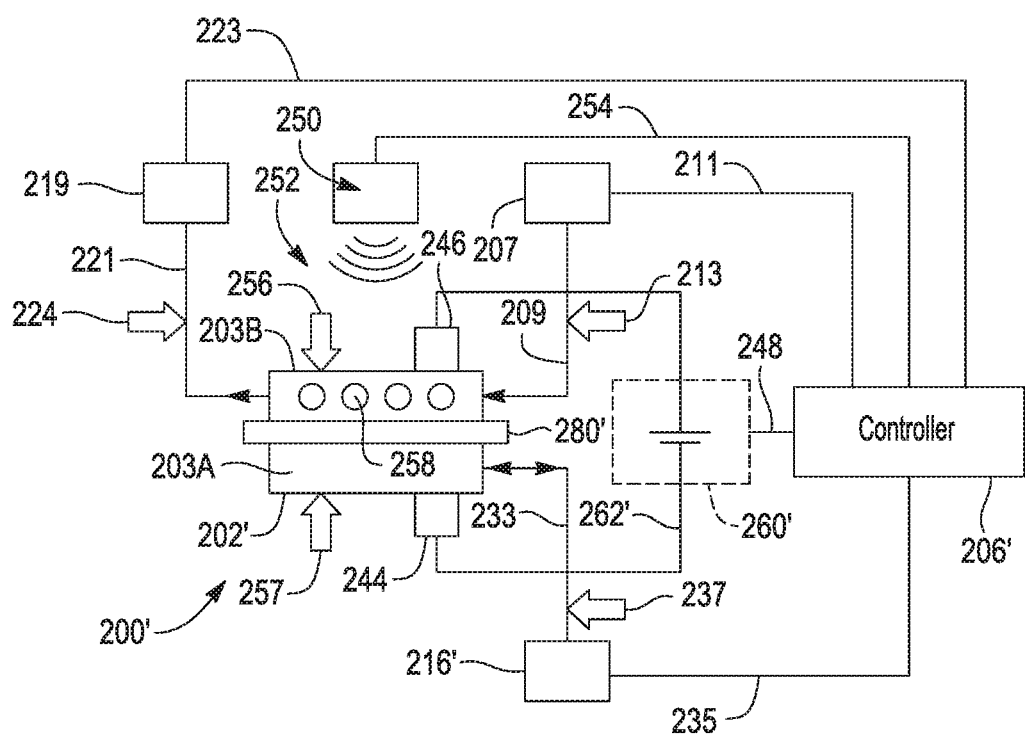
FIG. 5B illustrates an example of a system that allows streamlined separation and extraction of nucleic acids from samples that may be used in the application illustrated in FIG. 4.

Two example systems 200, 200' for implementing the method 100 are shown in FIGS. 5A and 5B, respectively.

The system 200, illustrated in FIG. 5A, may have an electrophoretic fluidic device 202. Fluidic device 202 may have a sample chamber 204A, in which samples containing cell free DNA may be deposited. System 200 may also have an elution chamber 204B, in which cell free DNA may be released for collection. Elution chamber 204B may be filled with an elution buffer (e.g., Tris Acetate Ethylenediaminetetraacetic or TAE, Tris Borate Ethylenediaminetetraacetic, 2-Amino-2-(hydroxymethyl)-1,3-propanediol, THAM, Tris base, Tris(hydroxymethyl)aminomethane, Trometamol or Trizma, etc.). Fluidic device 202 may be operated by a controller 206, which may regulate fluidic circuits, electrical circuits, and the DNA separation process, among other processes performed in system 200. Fluidic device 202 may be a microfluidic chip fabricated using polydimethylsiloxane (PDMS), glass and/or some other resin, and may be fabricated employing three-dimensional printing, molding, machining, or any other suitable fabrication method. Internal surfaces of the fluidic device 202 that may contact any of the fluids may be fabricated with non-DNA binding plastics, resins, or glass, to prevent loss of DNA. Fluidic device 202 and that may be handled by system 200 employing automatic mechanisms.

Elution chamber 204B may be coupled to a fluidic circuit 208 that may be used to collect eluted DNA that accumulates in elution chamber 204B. A pump 210 may produce fluid circulation between elution chamber 204B, outlet channel 212, and inlet channel 214. Fluid circulation by pump 210 may prevent deposit of DNA in regions of the elution chamber 204B. Moreover, a collection chamber 216 may be placed in the inlet channel 214 to collect eluted DNA. In some implementations, collection chamber 216 may have beads, gel, or some other surface that may be used to keep DNA in the collection chamber 216 through biochemical affinity. Collection chamber 216 may be placed in outlet channel 212 or near the electrode 264. Pump 210 may be controlled by controller 206 via an actuator 218. Moreover, data acquired via a flow sensor 220 may be used to adjust flow rate in pump 210 via actuator 218. A chamber sensor 222 that senses pressure in the elution chamber 204B may also be used to adjust flow rate and/or pressure in pump 210. In some implementations, free diffusion may be used for accumulation of DNA in collection chamber 216, without the use of pump 210.

Sample chamber 204A may also be coupled to a fluidic circuit 228 that may be used to circulate sample containing cell free DNA. Circulation in fluidic circuit 228 may assist dissolution of cell free DNA, which facilitates the electrophoretic separation in system 200. Circulation may also prevent coagulation of samples in fluidic circuit 228. Fluid circulation in fluidic circuit 228 may be induced by pump 230. Pump 230 may induce circulation through an inlet channel 232, sample chamber 204A, and outlet channel 234. Pump 230 may be controlled by controller 206 via an actuator 236. Actuator 236 may be used to adjust the flow rate in fluidic circuit 228, and/or pressure in the sample chamber 204A. Controller 206 may also employ data obtained by a flow sensor 238 to adjust pump 230 via actuator 236. A chamber sensor 240 may also be used to obtain pressure information for use by controller 206.

To mobilize cell free DNA from the sample chamber 204A into elution chamber 204B, a power supply 260 (e.g., a power source) may be used to generate an ion-current in fluidic device 202 that drives DNA by applying a potential difference between electrodes 264 and 266. An electrical circuit may be formed by power supply 260, circuit 262, electrode 264, elution chamber 204B, sample chamber 204A, and electrode 266 to drive DNA. For example, power supply 260 may provide a positive potential to electrode 264 and a negative potential to electrode 266, generating migration of DNA from sample chamber 204A into elution chamber 204B. This effect may be enhanced by the adjustment of the pH of sample chamber 204A and elution chamber 204B. When the DNA is dissolved in an acid solution, the molecule may acquire a negative charge due to ionization. In some implementations, the different chambers may have each a distinct pH, based on a specific cell-free extraction protocol employed and the source sample. Operation of the power supply 260 may lead to an increase in the temperature of the sample chamber 204A and/or elution chamber 204B. Such changes in temperature may be monitored by the controller 206 using chamber sensors 222 and 240. Controller 206 may regulate power supply 260 using an actuator 268 to prevent excessive temperatures in fluidic device 202.

Separation between sample chamber 204A and elution chamber 204B may be provided by a filter 280, which may be a gel. A gel in the gel-based filter 280 may be, or comprise, an agarose gel, an agar gel, a polyacrylamide gel, a polysaccharide based gel, a polyethylene oxide base gel, synthetic hydrogels; or other gels may be used. Filter 280 may also be a membrane. Membrane-based filter 280 may comprise a polymeric film, such as a nitrocellulose film. Other materials, such as polycarbonate and poly(ethersulfone), may be used. In some implementations, a polyamide gel may also be used. Alternative types of filters may include track etched membranes and asymmetric membranes. More generally, filter 280 may prevent non-nucleic acid particles such as cells, cellular debris, proteins, and other matter from crossing from sample chamber 204A to elution chamber 204B. Filter 280 may also be used to separate nucleic acids (e.g., DNA) based on size. For example, a gel-based filter 280, along with a suitable protocol by controller 206, may be used to select nucleic acids based on a molecular mass threshold or length (e.g., number of base pairs in the nucleic acid sequence), as detailed below. Membrane-based filter 280 may be selected based on a pore size, relative to the size of the nucleic acids of interest (e.g., DNA) and/or of the size of debris found in biological samples. Membranes may have a pore size ranging from about 50 nm to about 500 nm.

The system 200', illustrated in FIG. 5B, may also include an electrophoretic fluidic device 202'. Fluidic device 202' may have an elution chamber 203A (e.g., an elution volume, an inner elution volume), in which extracted and separated DNA may be released for collection. Fluidic device 202' may also have a sample chamber 203B (e.g., a sample volume, an inner sample volume), in which samples may be deposited and DNA may be extracted, as further detailed below. Fluidic device 202' may be operated by a controller 206', which may regulate fluidic circuits, electrical circuits, and the DNA extraction process, among other processes in system 200'. The fluidic device 202' may configured as any suitable physical component or collection of components, such as a microfluidic chip fabricated using PDMS, glass and/or some other resin, and that may be handled by system 200' employing automatic or semiautomatic control. Fluidic device 202' may also be a standalone apparatus formed with acrylic, plastic or any other suitable material and that may have electrical and fluidic connection for coupling with other discrete devices to form system 200'.

In the illustrated implementation, to load a sample in fluidic device 202', sample chamber 203B may receive the sample from a sample reservoir 207 through a fluidic channel 209. Fluidic channel 209 may include, for example, tubing and/or channels in the fluidic device 202'. Controller 206' may command the sample to be moved from sample reservoir 207 to sample chamber 203B by an actuator 211. Actuator 211 may be, for example, a pressure pump, a peristaltic pump, or any other suitable fluidic device that may generate the desired flow. Note that based on the type of sample in sample reservoir 207, actuator 211 may be designed to move the sample without damage to the materials of interest. Furthermore, fluidic channel 209 may be provided with a sensor 213 that may measure flow and/or transferred volume and provide feedback information for controller 206', such as for closed-loop control, monitoring, and so forth.

Waste at the end of the process may accumulate in sample chamber 203B of fluidic device 202'. Fluids from sample chamber 203B may be delivered to a waste reservoir 219 through a fluidic channel 220. Similarly to fluidic channel 209, fluidic channel 221 may include, for example, tubing and/or channels in fluidic device 202'. Controller 206' may regulate the flow into waste reservoir 219 through an actuator 223, which may be a pressure pump, a peristaltic pump, or any other device to generate the desired flow. Actuator 223 may become active once the DNA extraction process is finished, as detailed below. To regulate that flow, the controller 206' may employ data received by a sensor 224 that may measure flow through fluidic channel 221 and may, for example, identify a clog in fluidic channel 221 or a fill condition in waste reservoir 219.

Purified DNA may accumulate in the elution chamber 203A of the fluidic device 202' at the end of the process performed by system 200'. The DNA may be extracted into a collection chamber 216' via a fluidic channel 233. Fluidic channel 233 may have, for example, tubing and/or channels in fluidic device 202'. Controller 206' may regulate the extraction of DNA through the fluidic channel 233 via an actuator 235. In some implementations, collection chamber 216' may have beads, gel or some other surface that attaches to DNA, such as through biochemical affinity. In such implementations, natural diffusion between elution chamber 203A and collection chamber 216' may lead to accumulation of DNA in the collection chamber 226'. In some implementations, fluidic channel 233 may be a closed fluid circuit between elution chamber 203A and collection chamber 216', and accumulation of DNA in the collection chamber 216' may be regulated via a pressure pump, a peristaltic pump or any other device to produce flow in fluidic channel 233. Controller 206' may regulate the flow through fluidic channel 233 through an actuator 235. Controller 206' may also employ a sensor 237 to obtain closed loop strategies for controller 206' to regulate flow in fluidic channel 233.

Fluidic device 202' may be attached to a power source 260' (e.g., power supply) via an electrical circuit 262'. Elution chamber 203A may be coupled to the electrical circuit 262' via an adjacent electrode 244. Sample chamber 203B may be coupled to the electrical circuit 262' via a second adjacent electrode 246. Power source 260' may induce motion of free DNA from the sample chamber 203B through an electrophoretic process. For example, power source 260' may generate a potential difference between electrodes 244 and 246 such that electrode 244 becomes a cathode and electrode 246 becomes an anode. Due to the electric field generated in the fluidic device 202', DNA and/or other nucleic acids that may be released from cells in sample chamber 203B may migrate to elution chamber 203A. Power source 260' may include, for example, a voltage generator or a current generator capable of providing electrical energy at desired current and/or voltage levels for the migration process. Furthermore, power source 260' may operate using protocols that may include a current specification, voltage specification and/or a time specification for the electrophoresis process. Controller 206' may be configured with protocols, which may be transmitted via a power circuit 248, which may include an amplifier, or any other suitable arrangement for providing the desired electrical power to the electrodes 244, 246.

System 200' may also have an energy source 250 for causing lysis in the cells. For example, energy source 250 (e.g., an acoustic horn, ultrasonic horn, sonicator) may generate pressure waves 252 (e.g., an ultrasound vibration, an acoustic wave, acoustic energy, etc.). Pressure waves 252 may be transmitted to sample chamber 203B and induce lysis of cell walls, cell membranes and/or nuclear membranes (e.g., sonication). Controller 206' may regulate the energy source 250 through an actuator 254.

The volume of the sample in sample chamber 203B may be in a mechanical lysis medium. In some situations, the mechanical lysis medium may be adjusted to facilitate lysis through adjustments in components and conditions, such as in temperatures, addition of detergents or enzymes, adjustment of salt concentration to generate osmotic pressure, or any other methods that may make cell membranes and/or walls fragile. Moreover, beads 258 may be added to the mechanical lysis medium in sample chamber 203B to transmit pressure waves 252 to cells in the sample chamber 203B. In some situations, beads 258 may oscillate at a frequency that is related to the frequency of pressure waves 252 (e.g., same frequency or some harmonic) generated in energy source 250. Beads 258 may have dimensions in a range of from about 100 μm to about 150 μm.

System 200' may also have sensors 256 and 257 that may measure certain properties of fluidic chambers 203B and 203A, respectively. Sensors 256 and 257 may, for example, measure temperature and/or volume of the liquid in the respective chambers 203B and 203A. Volume measurements from sensors 256 and 257 may, for example, be used by controller 206' to regulate flow actuators 211 and 221. Temperature measurements from sensor(s) 256 may, for example, be used by the controller 206' to adjust the pressure waves 252, as delivery of energy by energy source 250 may increase temperature in sample chamber 203B. Similarly, volume measurements from sensor(s) 257 may, for example, be used by controller 206' to regulate flow actuator 235. Furthermore, temperature measurements from both sensors 256 and 257 may be used by controller 206' to regulate the power source 260', as electric fields may generate heat in fluidic chamber 202'. Furthermore, a nucleic acid separation filter 280' separates sample chamber 203B and elution chamber 203A. Filter 280' may restrict beads 258 in the sample chamber 203B. Filter 280' may also prevent undesired cell debris and other intracellular material released from crossing into elution chamber 203A.

As discussed above, controller 206 may process data received by sensors 220, 222, 238, 240, and 270, or any other sensors in system 200, and may provide commands to the system 200 via actuators 218, 236, and 268 or any other actuator, circuit, or device in system 200. Similarly, controller 206' may process data received by sensors 213, 224, 237, 256, and 257, or any other sensors in system 200', and may provide commands to the system 200' via actuators 211, 223, 235, 248, and 254, or any other actuator, circuit, or device in system 200'. FIG. 3 is a diagram of an example of a controller 206, 206' that may be used, respectively, with the system 200, 200'. Controller 206, 206' may have a processor 302 attached to, and in data communication with, a memory 304. Memory 304 may store protocols 306 for the process of DNA separation and/or configurable settings 308 for system 200, 200' that may be adjusted by controller 206, 206' (or where desired, manually or by a remote system). In order to interact with system 200, 200', processor 302 may be coupled to an interface circuit or circuits 310 that is also connected to actuators 312 and sensors 314. Certain control strategies that may employ closed-loop control may determine controls for actuators 312 based on data acquired from sensors 314, as well as by protocol 306 and/or settings 308 loaded in and implemented by the processor 302. Processor 302 may also be able to provide information (related to system 200, 200') to and/or receive information from a user via user interface 316. Information may include, for example, the status of system 200, 200' and/or its various sensors 314, which protocols 306 and/or settings 308 are currently loaded in processor 302, which protocols 306 and/or settings 308 may be chosen by the user, etc. User interface 316 may also provide direct control of actuators 312 (e.g., for manual operation or override).

The system 200 shown in FIG. 5A for obtaining cell free DNA will now be described in more detail in reference to FIGS. 7 through 15.

Figure 7:
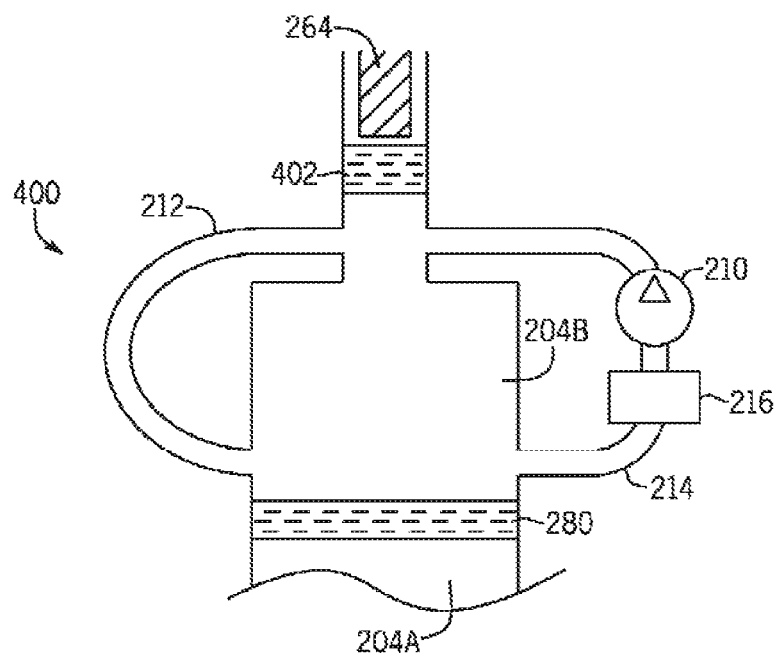
FIG. 7 illustrates an example of a fluidic circuit and electrode coupling for an elution chamber that may be used in the system of FIG. 5A for extraction of cell free nucleic acids, in accordance with an implementation.

As illustrated in FIG. 5A, the elution chamber 204B may be coupled to a fluidic circuit 208. Diagram 400 in FIG. 7 illustrates such a fluidic circuit 208. In this diagram 400, elution chamber 204B is coupled to an outlet channel 212 and an inlet channel 214. A collection chamber 216 may be coupled to the inlet channel 214. Collection chamber 216 may have gel or beads with affinity for nucleic acids to capture any nucleic acids eluted during the operation. In some implementations in which specific nucleic acids sequences are targeted, collection chamber 216 may include beads or gels having corresponding affinity markers that target the specific nucleic acids containing that sequence. This affinity may take place using electrostatic charges or hybridization.

The fluidic device 208 as represented by diagram 400 in FIG. 7 may also have a pump 210 that induces flow in the fluidic circuit 208. Pump 210 may be a peristaltic pump, a pressure pump, or any other suitable pump system. Diagram 400 in FIG. 7 also illustrates a filter 402 that may be used to prevent contact between nucleic acids (e.g., DNA) and electrode 264. As discussed above, electrode 264 may be positively charged during operation of system 200. As a result, DNA eluted in elution chamber 204B may migrate towards electrode 264 during operation. The contact between nucleic acids and electrode 264 may lead to nucleic acids damage through electrolysis. A filter 402, which may be an agarose gel (e.g., a 4% agarose gel), a polyethersulfone membrane or other gels or membranes, such as the ones above discussed, may be employed to create a physical barrier between the eluted nucleic acids in elution chamber 204B and electrode 264. In some implementations, electrode 264 may be coated employing a fluoropolymer or other fluorinated coating (e.g., an amorphous fluoropolymer such as CYTOP), which may provide that barrier. The use of the fluorinated coating and/or agarose gel may prevent electrolysis of nucleic acids molecules (e.g., 20% reduction, 50% reduction, 80% reduction, 90% reduction, 99% reduction, complete elimination) in electrode 264.

Figure 8:
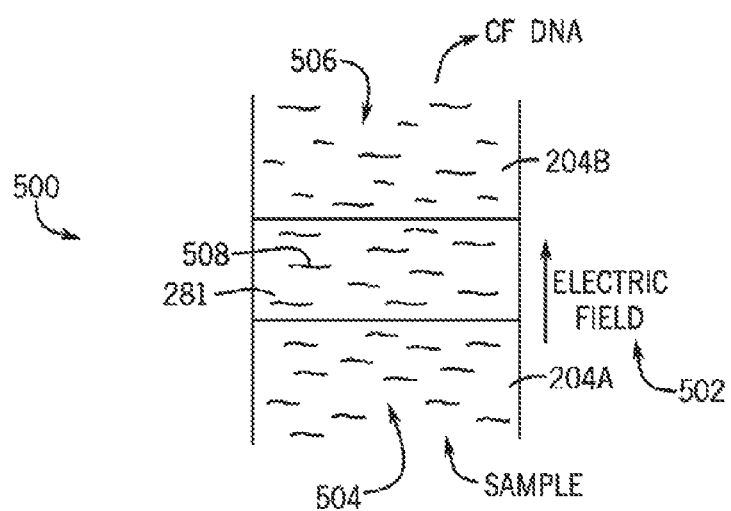
FIG. 8 is a schematic diagram of an example gel separation system that may be used with the system of FIG. 5A for extraction of cell free nucleic acids, in accordance with an implementation.

Diagram 500 in FIG. 8 illustrates the movement of DNA across the filter 280, which in this example, is a gel 28. Gel 281 may be used as a filtering barrier between sample chamber 204A and elution chamber 204B. Sample DNA 504 may be composed of DNA from multiple sources such as genomic DNA, plasmid DNA, viral DNA, and cell free DNA. The cell free DNA may be different from other DNA sources based on the size of the fragment. For example, in some situations, cell free DNA may be in a range between about 100 bp (base pairs) and about 320 bp, while genomic DNA may be larger than 500 bp. In order to adjust the threshold of the filtration using gel 281, length and gel density may be adjusted. For example, the length of the gel 281 may be in a range from about 0.5 mm to about 10 mm and an agarose gel may be prepared from an agarose solution with a concentration ranging from about 0.5% to about 10%. As an electric field 502 is applied across the gel 281, sample DNA 504 may enter into the gel 281 and become embedded (embedded DNA 508). Electric field 502 may further force the migration of embedded DNA 508 across the gel 281 towards the elution chamber 204B. The smaller the length of the embedded DNA 508, the quicker it travels through the gel 281. As embedded DNA 508 reaches the interface between the gel 281 and the elution chamber 204B, it may be released into solution to become eluted DNA 506. Based on the duration and intensity of the applied electric field 502, eluted DNA 506 may be substantially composed of cell free DNA. In some implementations, the intensity of the electric field applied across gel 281 may range from about 1 V/cm to about 100 V/cm and may be adjusted by controlling the power supply 260 (FIG. 5A).

Figure 9:
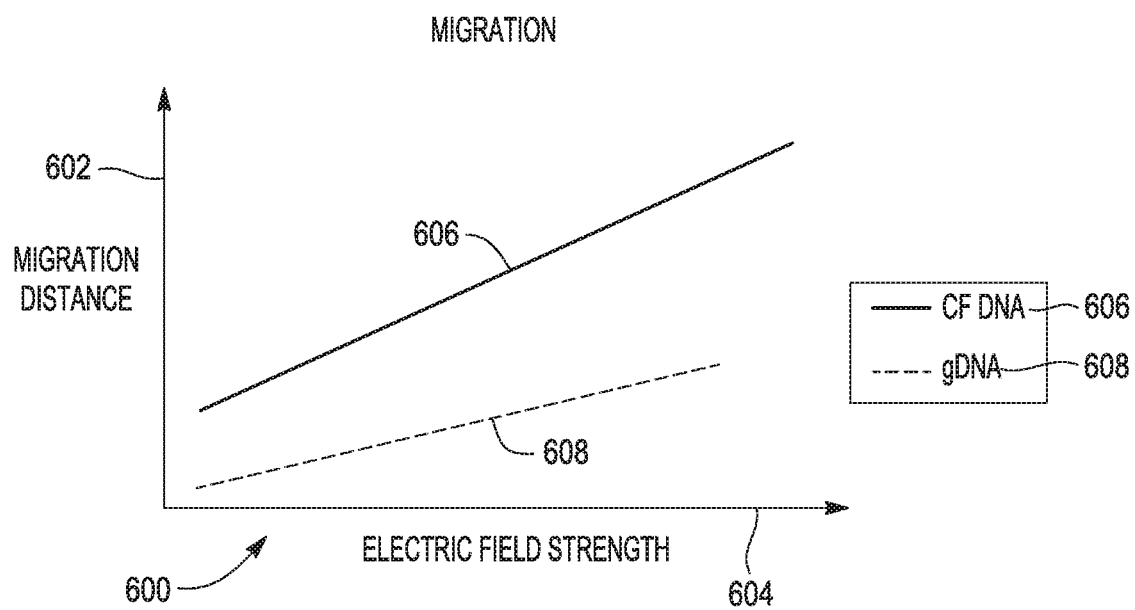
FIG. 9 is a chart that illustrates an example of a relation between nucleic acid migration and electric field strength and may be used by a protocol employed in the controller of FIG. 6.

As discussed above, the migration of embedded DNA 508 may depend on the intensity and duration of the applied electric field 502. Chart 600 in FIG. 9 illustrates this effect by providing a migration distance 602 for embedded DNA 508 as a function of electric field strength 604 for a fixed period of time. Migration distance 602 is given both for cell free DNA 606 (CF DNA) and genomic DNA 608 (gDNA). Note that as the electric field strength 604 increases, the migration distance for a given DNA molecule increases, both for cell free DNA 606 and genomic DNA 608. For a particular electric field strength 604, there is a migration distance 602 that may be used as a threshold to discriminate cell free DNA 606 and genomic DNA 608. Protocols and settings employed by controller 206 in the system 200 of FIG. 5A may take this information into account to choose an appropriate level for power supply 260 based on dimensions of the gel 281 and the length of the cell free DNA 606 of interest.

Figure 10:
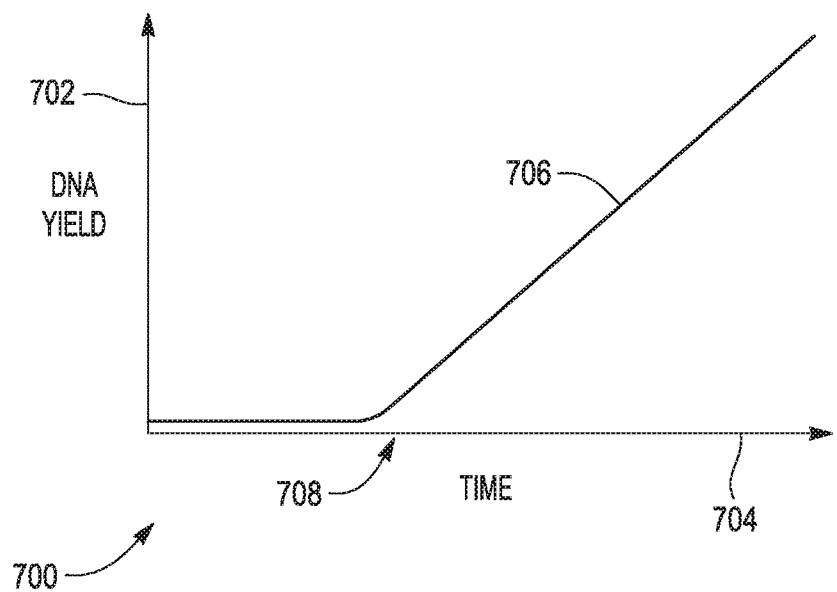
FIG. 10 is an chart that illustrates an example of a relation between nucleic acid yields and a protocol run time, and may be used by a protocol employed in the controller of FIG. 6.

Protocols employed by controller 206 in system 200 may also determine a duration for the electric field applied by power supply 260. Chart 700 in FIG. 10 illustrates DNA yield 702 as a function of the duration (time) 704 of the electric field across a gel 281. The illustrated curve shows the relationship for cell free DNA 706. Note that for low duration 704, the DNA yield 702 remains low for cell free DNA 706. This corresponds to a situation in which the migration distance is not long enough, and all the DNA remains embedded in the gel 281. As the duration 704 becomes larger than a threshold duration 708, the DNA yield 702 for cell free DNA 706 starts increasing monotonically with the duration 704. As the duration 704 becomes even larger than threshold 708, DNA yield 702 for genomic DNA may increase as the migration distance of genomic DNA 608 increases, which may lead to a contamination in the eluted DNA. As a result, for longer durations 704, the DNA obtained may include genomic DNA or other DNAs of large lengths or molecular weights. Protocols performed by controller 206 may use information, such as that provided in chart 700, to determine the duration 704 of the electric field based on a threshold molecular weight that discriminates between cell free DNA and genomic DNA, and a desired DNA yield.

Figure 11:
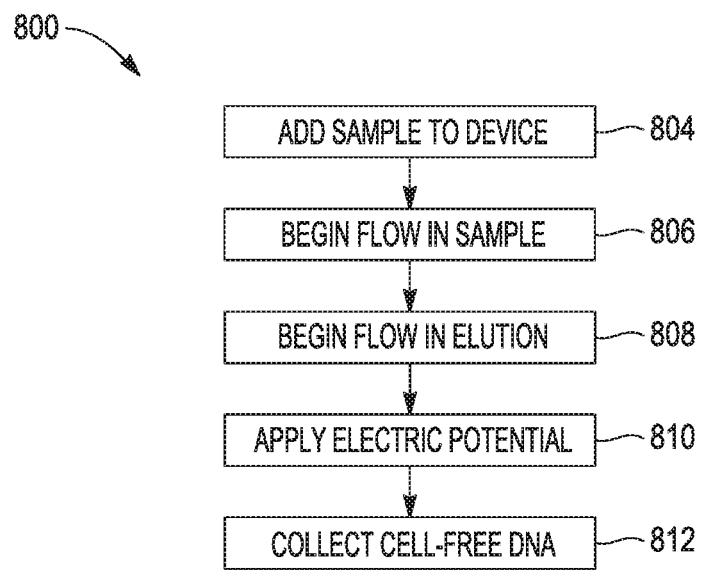
FIG. 11 is a flow chart illustrating an example method to use a system, such as the one of FIG. 5A, for extraction of cell free nucleic acids, in accordance with an implementation.

An example of a method to use system 200 to acquire cell free DNA directly from, for example, a whole blood sample, is illustrated in flowchart 800 in FIG. 11. In a process 804, the sample may be added to the device. Note that the acquired blood sample may be treated with anticoagulant, proteinases, DNA stabilizers (e.g., EDTA), and other agents to stabilize the sample for extraction of the cell free DNA from blood using system 200. For example, collection tubes containing the pre-treatment reagents may be used to receive a sample immediately following collection. A blood sample may also include processes for adjusting the pH of the blood sample by addition of salts, dissolution of the sample in a buffer, or some other method. In some implementations, a device may have a sample chamber pre-loaded with a solution containing EDTA and a pH buffer, and pre-treatment is performed along with introduction of the sample in the pre-loaded chamber (process 804).

In some implementations of the method shown in FIG. 11, the sample loaded in process 804 may have small volumes (e.g., smaller than about 1 ml), using microfluidic devices. In other implementations, the loaded sample may be larger (e.g., in a range from about 1 ml to about 10 ml). In some implementations, the volume may be loaded in an external chamber and circulated into the sample chamber 204A through the fluidic system 208. Certain implementations may also allow parallel usage of multiple devices. To this end, multiple devices may be individually loaded and processed by system 200, or an automated system may load multiple devices from a sample reservoir. Such a system may allow for the analysis of substantially larger samples (e.g., from about 5 ml to about 500 ml).

As the sample is pre-loaded, flow may be introduced in the sample chamber (process 806). Flow in the sample chamber 204A may be used to facilitate loading of the sample, homogenize the sample during the DNA extraction, as well as to prevent coagulation or formation of suspensions in the sample chamber 204A. Similarly, flow in the elution chamber 204B may also be introduced (process 808). The introduction of flow in the chambers 204A and 204B may take place by operation of pumps 210 and 230, illustrated in FIG. 5A. As discussed above, controller 206 may be used to adjust the flow based on system 200 settings, chosen operation protocol, and/or data acquired by any of the sensors 220, 222, 238, and 240.

Controller 206 may also induce power supply 260 to apply electric potential between the electrodes 264 and 266 coupled to the fluidic device 202 (process 810 in FIG. 11). The electric potential applied between electrodes 264, 266 may generate an electric field across filter 280 that leads to elution of cell free DNA into elution chamber 204B. As discussed above, the duration and intensity of the electric potential applied by power supply 260 may be adjusted based on a configuration for length or molecular weight for cell free DNA and genomic DNA. With the choice of an appropriate protocol, the elution chamber 204B may have eluted DNA composed of a high concentration of cell free DNA and low concentration of genomic DNA. In implementations having a collection chamber 216, the eluted DNA may be circulated into the elution chamber 204B that holds the eluted DNA for later collection (process 812 in FIG. 11). In other implementations, the buffer in the elution chamber 204B may be collected as a whole and DNA may be separated or purified by another system or method. The collected DNA may be used for sequencing, quantification, detection, amplification, cloning, or any other application.

Figure 6:
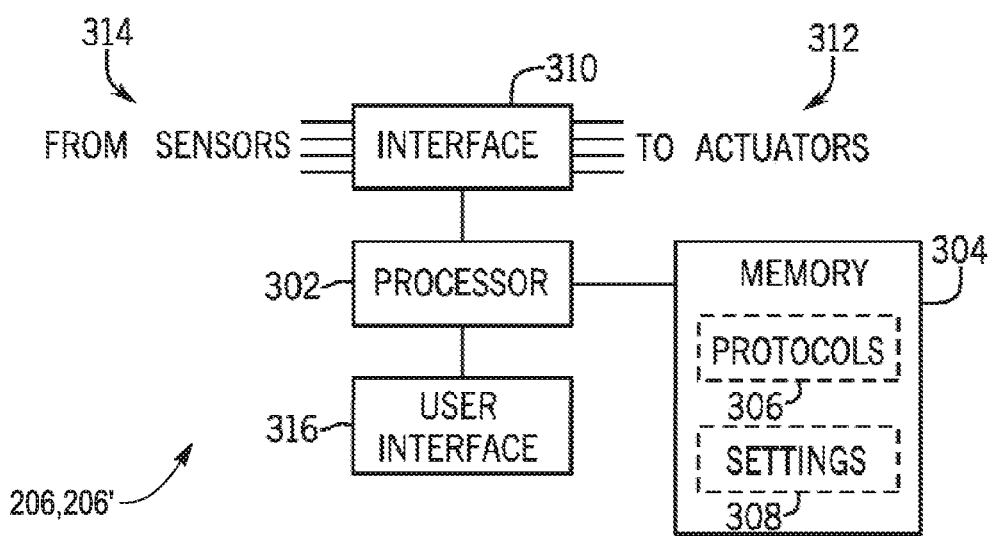
FIG. 6 illustrates an example of a controller that may be used by the system of FIG. 5A or the system of FIG. 5B.
Figure 12:
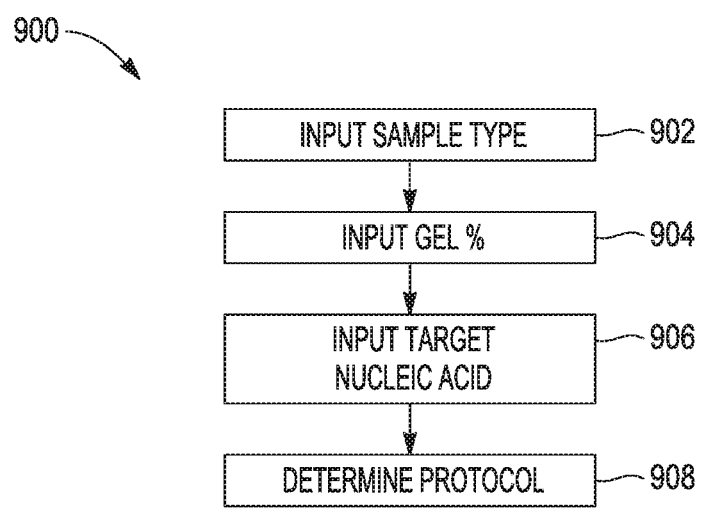
FIG. 12 is a flow chart illustrating an example method to obtain a protocol for extraction of cell free nucleic acids for a gel separation system, in accordance with an implementation.

As discussed above, the extraction process of cell free DNA may be more effective if an appropriate protocol is employed. As discussed in reference to FIG. 6, controller 206 may have a memory 304 that store protocols 306 and settings 308. The user interface 316 may be used by controller 206 to assist a user in the choice of a protocol 306. Flowchart 900 of FIG. 12 illustrates an example of a method performed by a user that may use a user interface 316 to choose a protocol 306. In a process 902, the user may input, to the user interface 316, the sample type. For example, the sample type may be blood, urine, skin swab, biopsy, or any other sample. Process 902 may also inquire further about the origins of the sample. For example, if a user selects blood as a sample type, user interface 316 may inquire further the collection method and any pre-treatment of the sample.

In a process 904, the user may also input, to the user interface 316, characteristics of the fluidic device 202 employed. Configurations such as dimensions, composition, and concentration of the gel 281 may be provided by the user to controller 206 via user interface 316. In some implementations, each type of fluidic device 202 may be a consumable having a code. The user may provide this code via the user interface 316 in process 904, and processor 302 may identify a protocol 306 that is appropriate for the fluidic device 202 based on the code. In some implementations, the user interface 316 may be associated with a bar code reader, a QR reader, an RFID sensor, or some other reader that may identify the code of the device based on a machine-readable tag in fluidic device 202.

The user may also provide, to user interface 316, information related to the desired nucleic acid (process 906 in FIG. 12). The information about the desired nucleic acid may be a DNA length or molecular weight of the desired nucleic acids, or a range of desired lengths or molecular weights. In some implementations, a threshold value may be chosen (e.g., the desired nucleic acids are below a particular threshold). As examples, the user may specify that nucleic acids range from about 150 bp to about 600 bp, or may specify a threshold of about 500 bp for the nucleic acids. In some implementations, user interface 316 may provide access to information stored in memory 304 related to types of cell free nucleic acids desired. For example, the user interface 316 may receive information related to a type of cell free DNA (e.g., fetal cell free DNA, cancer-associated cell free DNA, infection associated DNA, etc.), and the system 200 may have a protocol 306 associated to the target type stored in memory 304. Finally, based on the information received relative to the sample type, the fluidic device 202 employed, the system 100 employed, and a target DNA, the processor 302 may retrieve a protocol 306 from memory 304 based on that information (process 908 in FIG. 12). In some applications, protocol 306 may be associated with system settings 308.

Figure 13:
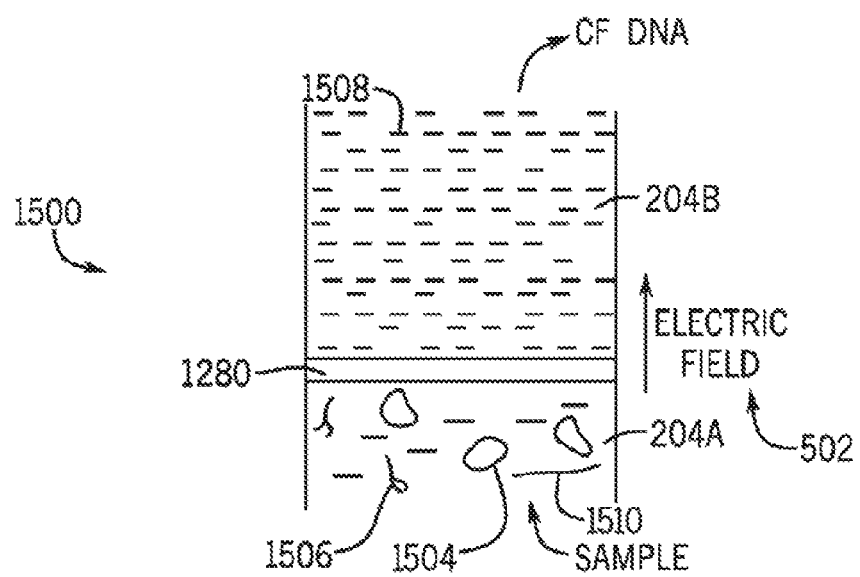
FIG. 13 is a schematic diagram of an example membrane separation system that may be used with the system of FIG. 5A for extraction of cell free nucleic acids, in accordance with an implementation.

As discussed above, system 200 may employ a membrane-based filter for separating cell free DNA. Diagram 1500 in FIG. 13 illustrates the movement of DNA across a membrane 1280 (an example of the filter 280). Membrane 1280 may be used as a filtering barrier between sample chamber 204A and elution chamber 204B. Sample chamber 204A may have a mixture of cells 1504, proteins and other debris 1506, cell free DNA 1508, and genomic DNA 1510. The cell free DNA 1508 may be different from genomic DNA 1510 based on the size of the molecule. For example, in some situations, cell free DNA 1508 may be in a range of from about 100 bp to about 320 bp, while genomic DNA 1510 may be larger than about 5000 bp. A membrane 1280 may be chosen to discriminate between the cell free DNA 1508 and the genomic DNA 1510. For example, the pore size of the membrane 1280, the thickness of the membrane 1280, or a stack of membranes 1280 may be used to selectively separate cell free DNA 1508 from genomic DNA 1510, debris 1506, and cells 1504. As an electric field 502 is applied across membrane 1280, cell-free DNA 1508 may be pushed through the membrane 1280 and into elution chamber 204B. Note that the duration and intensity of electric field 502 applied may act as a force, and therefore, an appropriate electric field 502 may be chosen to reduce the chance of genomic DNA 1510 or other negatively charged proteins (e.g., debris 1506) from crossing the membrane 1280. In some implementations, the intensity of the electric field applied across membrane 1280 may range between about 1V/cm and about 100V/cm and may be adjusted by controlling the power supply 260.

Figure 14:
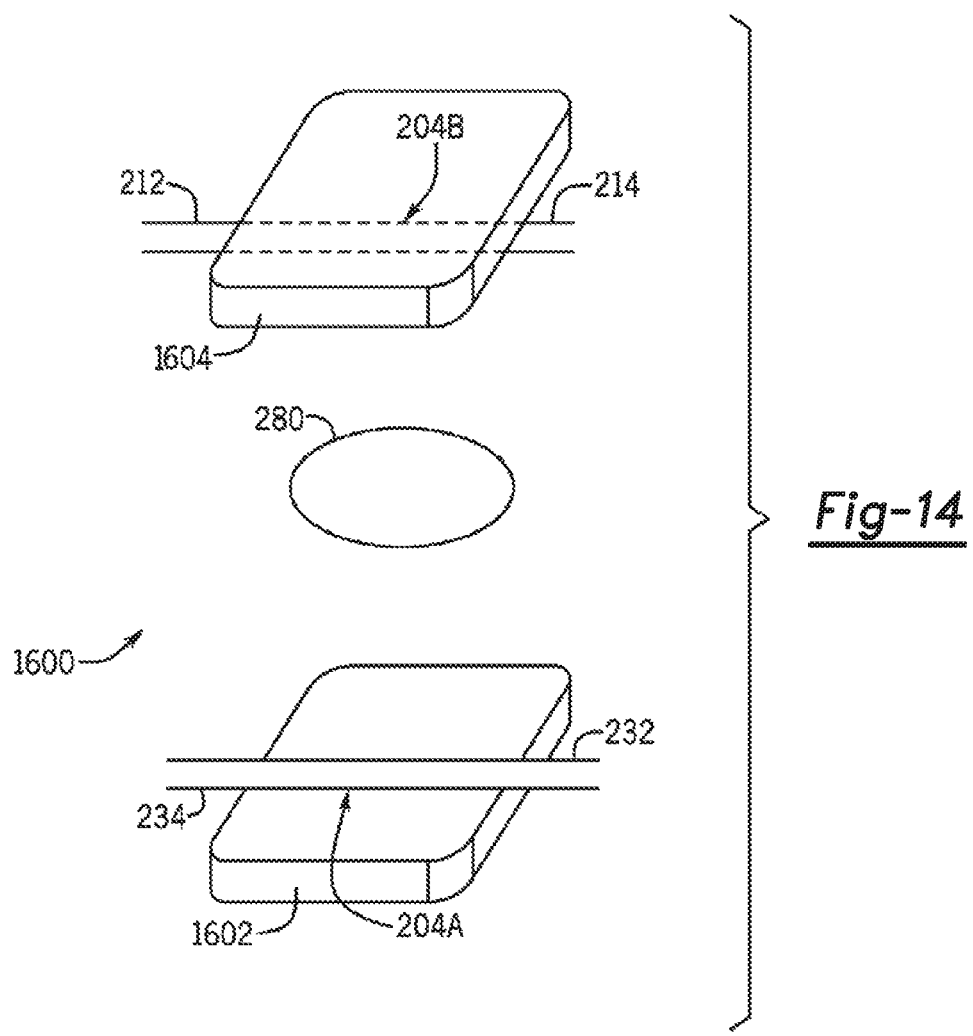
FIG. 14 is a diagram illustrating an example of a method to assemble a membrane separation device that may be used in the system of FIG. 5A.

The exploded view 1600 in FIG. 14 illustrates one possible architecture for a membrane-based fluidic device 202. Fluidic device 202 may be assembled using a lower chip 1602 having a sample chamber 204A that is linked to an inlet channel 232 and an outlet channel 234. Note that sample chamber 204A is exposed in a top surface of lower chip 1602. The lower chip 1602 may be pressed against an upper chip 1604 having the elution chamber 204B that is connected to a corresponding inlet channel 214 and outlet channel 212. The elution chamber 204B may be exposed in the bottom surface of upper chip 1604. The lower chip 1602 and the upper chip 1604 may be pressed with a membrane (one example of filter 280) placed between them to form the device 202. Electrodes 266, 264 may be respectively attached to be adjacent to the sample chamber 204A and the elution chamber 204B.

Figure 15:
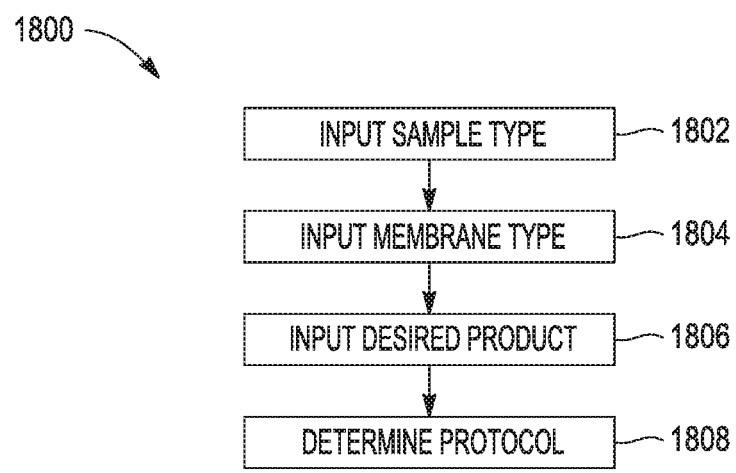
FIG. 15 is a flow chart illustrating an example of a method to obtain a protocol for extraction of cell free nucleic acids for a membrane and/or filter separation system, in accordance with an implementation.

The extraction process may be more effective if an appropriate protocol is employed based on the membrane. As discussed in reference to FIG. 6, controller 206 may have a memory 304 that store protocols 306 and settings 308. User interface 316 may be used to assist a user in the choice of a protocol 306. Flowchart 1800 in FIG. 15 illustrates an example of a method performed by a user, who may use the user interface 316 to choose a protocol 306. In a process 1802, the user may input, to the user interface 316, the sample type. For example, the sample type may be blood, urine, skin swab, biopsy, or any other sample. Process 1802 may also inquire further about the origins of the sample. For example, if a user selects blood as a sample type, user interface 316 may inquire further the collection method and any pre-treatment of the sample.

In a process 1804, the user may also input, to user interface 316, characteristics of the fluidic device 202 employed. Configurations such as dimensions, composition, and concentration of membrane 280 may be provided by the user to controller 206 via user interface 316. In some implementations, each type of fluidic device 202 may be a consumable having a code. The user may provide this code via user interface 316 in process 1804, and processor 302 may identify a protocol 306 that is appropriate to the fluidic device 202 based on the code. In some implementations, the user interface 316 may be associated with a bar code reader, a QR reader, an RFID sensor, or some other reader that may identify the code of the device based on a machine-readable tag in fluidic device 202.

The user may also provide, to user interface 316, information related to the desired nucleic acid (process 1806 in FIG. 15). The information about the desired nucleic acid may be a DNA length or molecular weight of the desired nucleic acids, or a range of desired lengths or molecular weights. In some implementations, a threshold value may be chosen (e.g., the desired nucleic acids are below a particular threshold). As examples, the user may specify that nucleic acid range of from 150 bp to 600 bp, or specify a threshold of 500 bp for the nucleic acids. In some implementations, user interface 316 may provide access to stored information in memory 304 that is related to types of cell free nucleic acids desired. For example, the user interface 316 may receive information related to a type of cell free DNA (e.g., fetal cell free DNA, cancer-associated cell free DNA, infection associated DNA, etc.), and the system 200 may have a protocol 306 associated to the target type.

In some implementations, memory 304 may provide recommendations for the user related to which fluidic device 202 may be employed based on the type of sample entered. For example, if a user inputs, in process 804 and/or process 806, that the sample contains fetal cell free DNA, the user interface 316 may provide to the user recommendation of fluidic devices 202 that include an appropriate filter 208 (e.g., membrane or gel) to extract the cell free DNA and prevent other biological debris from being eluted. As discussed above, the interface 316 may also suggest an adequate fluidic device 202. In such situations, the user may accept the suggestion while performing process 1804. Finally, based on the information received relative to the sample type, the fluidic device 202 employed, the system 200 employed, and a target DNA, the processor 302 may retrieve a protocol 306 from memory 304 based on that information (process 1808 of FIG. 15). In some applications, protocol 306 may be associated with system settings 308.

The system 200' shown in FIG. 5B will now be described in more detail in reference to FIGS. 16 through 21. This system 200' may enable a streamlined process for obtaining DNA samples through mechanical lysis of cell walls and/or membranes and electrophoretic separation of DNA from other biomolecules. In an example, the biological cells include bacterial cells, and the separated DNA comprises genomic DNA.

Figure 16:
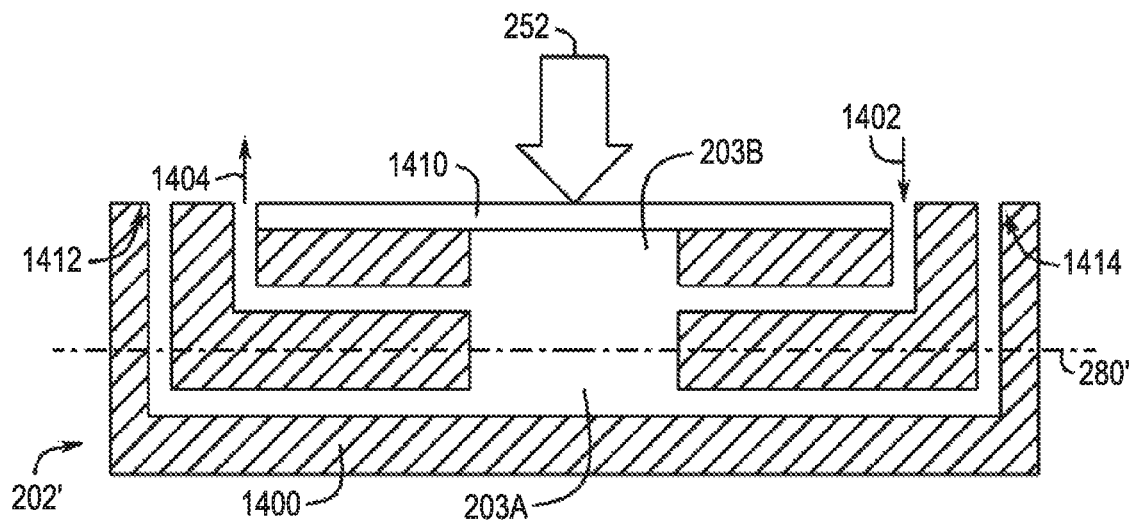
FIG. 16 is a schematic view of a microfluidic chip that may be used in the system of FIG. 5B for streamlined separation and extraction of nucleic acids, in accordance with an implementation.

FIG. 16 provides a schematic diagram for a fluidic device 202'. Fluidic device 202' may be formed, for example, in a fluidic chip 1400 that may be made of a resin, PDMS, or any other material. Fluidic device 202' may have an elution chamber 203A and a sample chamber 203B that may be separated by a filter 280'. Filter 280' may comprise a membrane having a thickness ranging from about 6 μm to about 10 µm, and may have pore sizes ranging from about 0.01 µm to about 0.45 µm. For example, pore sizes may be from about 0.01 µm to about 0.1 µm, from about 0.1 µm to about 0.2 µm, from about 0.2 µm to about 0.45 µm, or from about 0.1 to about 0.45 µm. Filter 280' may be hydrophilic, either due to intrinsic properties or due to some chemical treatment and/or coating (e.g., nylon treatment). Moreover, filter 280' may have particular affinity to proteins that retains protein in filter 280' and reduces the amount of small biomolecular contaminants (e.g., proteins, lipids, lipoproteins, polymeric sugars, etc.) in the elution chamber 203A. Moreover, the pores in filter 280' may have surface chemistry that facilitates transit of DNA from sample chamber 203B to elution chamber 203A and reduces transit of other small biomolecular contaminants through the pores. In some implementations, the filter 280' may be a nitro-cellulose membrane. In some implementations, filter 280' may be a combination of a membrane and a gel, such as an agarose gel (e.g., agarose gel, agar gel) or an acrylamide gel (e.g., polyacrylamide gel) to improve the selection capacity of filter 280'. In some implementations, filter 280' may be initially formed in fluidic chip 1400, or may be added during the production of fluidic chip 1400, or may be added as an insert after the formation of fluidic chip 1400.

Chambers 203A and 203B, and channels, such as inlet sample channel 1402, outlet sample channel 1404, inlet elution channel 1412, and outlet elution channel 1414 may be formed in or made by removing material from the fluidic chip 1400. As discussed above, system 200' may cause a sample to be loaded into chamber 203B via inlet sample channel 1402 and waste to flow out of chamber 203B via outlet sample channel 1404. Similarly, system 200' may cause elution buffer having purified DNA in elution chamber 203A to exit through outlet elution channel 1414. Inlet elution channel 1412 may be used to facilitate the flow of fluid. Inlet elution channel 1412 may be employed to load an appropriate elution solution into elution chamber 203A. For example, an elution solution may have a controlled alkaline level, with a pH substantially between 7 and 10, to facilitate the electrophoresis process. Furthermore, elution solution may be a buffered solution to reduce changes in the pH of the solution due to electrolysis in electrodes or release of intracellular salts during cell lysis. Buffers may employ tris(hydroxymethyl)aminomethane (Tris) combined with an acid (e.g., acetic acid, boric acid). Elution solution may also include stabilizing agents to prevent DNA degradation, such as ethylenediaminetetraacetic acid (EDTA).

To perform electrophoresis, cathodes (e.g., negative terminal electrodes) may be disposed in sample chamber 203B, in inlet sample channel 1402 and/or in outlet sample channel 1404, and anodes (e.g., positive terminal electrodes) may be disposed in elution chamber 203A, inlet elution channel 1412, and/or outlet elution channel 1414. As a voltage is applied between anodes and cathodes, an electric field may form in sample chamber 203B and elution chamber 203A across filter 280'. As DNA may have a negative charge, the electric field across filter 280' may drive DNA molecules from sample chamber 203B to elution chamber 203A. Filter 280' may prevent other contaminants from flowing from the sample chamber 203B to the elution chamber 203A, increasing purity of the extracted DNA.

As noted above, in some implementations, elution chamber 203A may have beads 258 or other supports with affinity for DNA to facilitate a purification process, DNA transposition, or tagmentation process. After the electrophoresis process, a large proportion of the extracted and separated DNA in elution chamber 203A may be attached to beads 258 or supports. System 200' may cause flow of these DNA-attached beads 258 or supports out of elution chamber 203A via outlet elution channel 1414. Separation of beads 258 or supports via size separation (e.g., filtering) or magnetic separation (e.g., using magnetic beads) followed by a release of the DNA from the beads 258 or supports in a fresh buffer may facilitate the production of pure, high concentration DNA. Moreover, in some situations, such as sequencing or DNA amplification, DNA-attached beads or supports may be directly employed in a downstream process. For example, elution chamber 203A may be configured to perform tagmentation reactions. Transposons with appropriate nucleotides and/or nucleic acids may be placed in elution buffer to fragment and tag the obtained DNA to create sequencing libraries compatible with high-throughput sequencing devices.

Fluidic chip 1400 may also have a membrane 1410 that receives pressure waves 252 received by fluidic device 202'. Membrane 1410 may be a pliable material that is capable of transmitting the pressure waves 252 into a mechanical vibration in the liquid contained in sample chamber 203B. In some situations, membrane 1410 may be a rigid material that may resonate and vibrate with the pressure waves 252, and the vibration may be transmitted to the sample chamber 203B. Membrane 1410 may be fabricated from a resin, a rubber material, a plastic material, a polymeric film, glass, or some other material. Furthermore, sample chamber 203B may have a mechanical lysis facilitating mechanism, such as glass beads to facilitate lysis of sample cells, as discussed below. Note that in some implementations, energy for lysis of cells may be provided through pneumatic agitation of the flow cell. Alternatively or in addition to pressure waves transmitted through membrane 1410, pumps in system 200' may generate flows in the volume of sample chamber 203B that may induce vibration, movement, or collision of beads. In some implementations, non-mechanical lysis, such as enzymatic or chemical lysis may be used, by injecting the appropriate buffers and enzymes in the sample chamber 203B. Note that the system 200' may be able to provide heat to the sample chamber 203B that may support enzymatic reactions, when that is appropriate.

Figure 17:
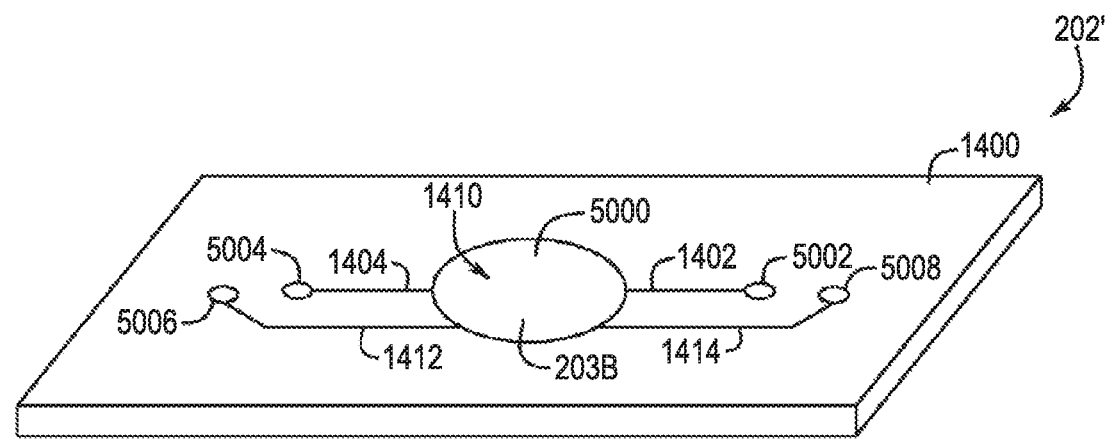
FIG. 17 is a perspective view of a microfluidic chip that may be used in the system of FIG. 5B for streamlined separation and extraction of nucleic acids, in accordance with an implementation.
Figure 18:
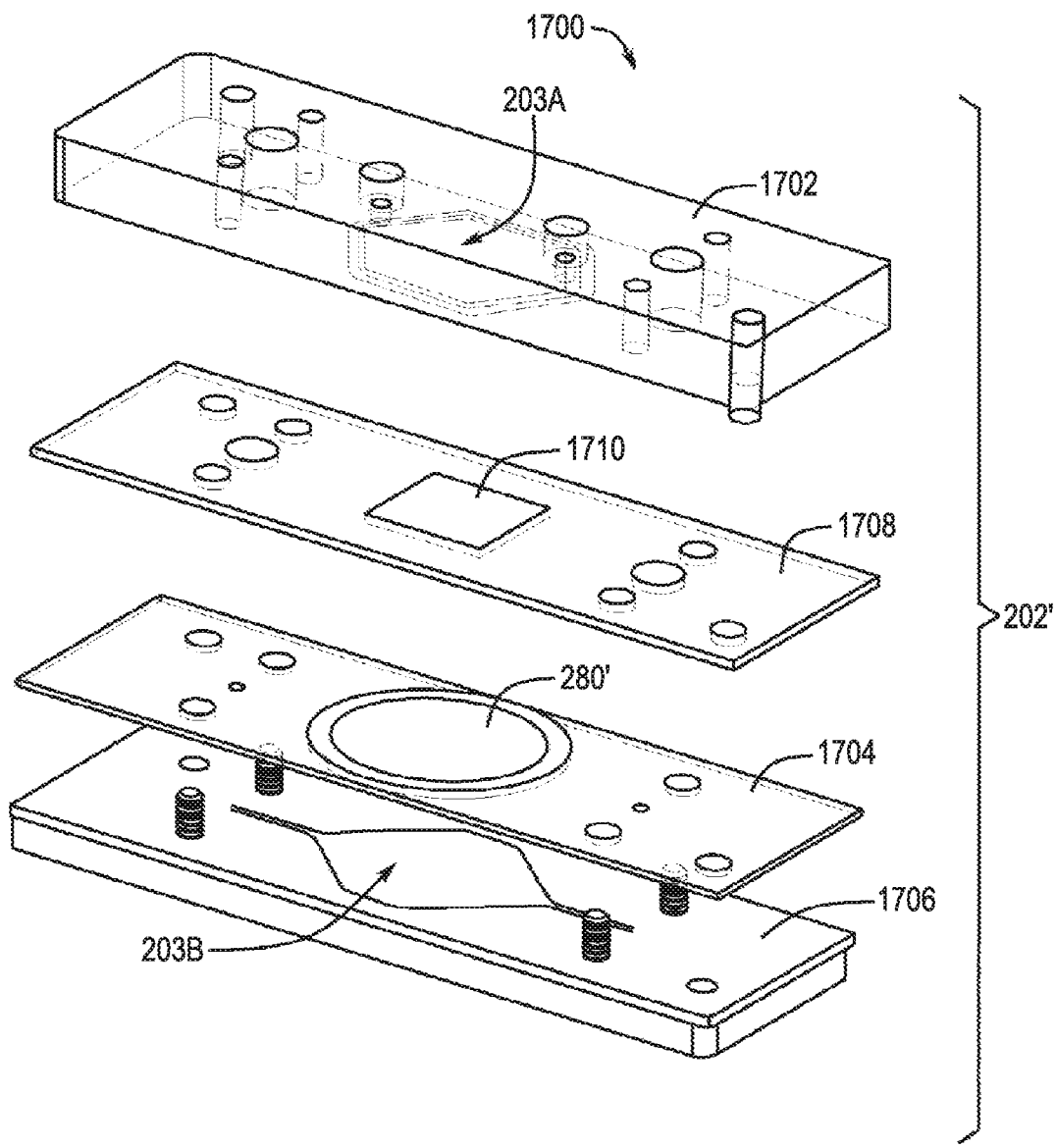
FIG. 18 is an exploded perspective view of a microfluidic chip that may be used in the system of FIG. 5B for streamlined separation and extraction of nucleic acids from fixed tissue, in accordance with an implementation.

FIG. 17 provides a perspective view of an implementation of a fluidic chip 1400. Fluidic chip 1400 may be formed from a polycarbonate plastic, poly(methyl methacrylate) (PMMA), polydimethylsiloxane (PDMS), or other suitable material. Channels and chambers may be formed through injection molding, soft lithography molding, laser cutting, or other methods suitable to the material. During fabrication, a region 5000 of fluidic chip 1400 having the sample chamber 203B above an elution chamber 203A (not illustrated in FIG. 17) may be formed. Chambers 203A and 203B may be fabricated to support high pressure flow as well as mechanical stress from agitation of beads or vibration from the energy source. In some implementations, chambers 203A and 203B may have heights in ranging from about 50 µm to about 300 µm. A membrane 1410 that receives pressure waves may cover sample chamber 203B in region 5000 providing a region for coupling of an energy source 250, such as an acoustic horn. Membrane 1410 may be an elastomeric membrane that is mounted to fluidic chip 1400 via an adhesive.

Region 5000 may receive channels such as inlet sample channel 1402, outlet sample channel 1404, inlet elution channel 1412, and outlet elution channel 1414. Channels may be coupled to their respective chambers in region 5000, as described above. Channels may also be coupled to system 200' via fluidic ports. Inlet sample channel 1402 may be coupled to port 5002, outlet sample channel 1404 may be coupled to port 5004, inlet elution channel 1412 may be coupled to inlet elution port 5006, and outlet elution channel 1414 may be coupled to outlet elution port 5008. Electrodes may also be coupled to the fluidic device at the port(s). Cathodes may be placed adjacent to ports 5002 and/or 5004, and anodes may be placed adjacent to ports 5006 and/or 5008. Note that anodes may be positioned to avoid direct contact with DNA in the elution buffer. In some implementations, a gel or a membrane may be placed between the anode and the buffer and/or the port to prevent direct contact. The location of ports 5002, 5004, 5006, and 5008 may follow a standard to facilitate automated coupling of fluidic chip 1400 to fluidic systems and electrical systems of system 200'. Moreover, dimensions of the fluidic chip 1400, such as length, width, and thickness, may also follow a standard to facilitate automated manipulation of fluidic chip 1400 in system 200'.

In some implementations, the sample may be recovered from some preservation embedding treatment, such as in frozen form or in formalin fixed paraffin embedded (FFPE) form. In these situations, the sample does not readily go into solution. Fluidic chip 1700, illustrated in FIG. 18, allows for integrated extraction directly from frozen tissues, FFPE tissues, or other fixed medium for samples. In fluidic chip 1700, a top layer 1702 and a bottom layer 1706 may sandwich a membrane layer 1704 as well as a slide layer 1708. Top layer 1702 may include the sample chamber 203A and bottom layer 1706 may include elution chamber 203B. The membrane layer 1704 may have filter 280' that prevents transit of cells and cellular debris and allow electrophoresis of nucleic acids from the sample chamber 203A into elution chamber 203B, as discussed above. Slide layer 1708 may be a layer for depositing of the fixed medium samples. For example, FFPE tissues or frozen tissues in gel or solid form may be placed in the center of slide layer 1708 prior to assembly of fluidic chip 1700 such that they go within sample chamber 203A. The fluidic chip 1700 may be then placed in system 200' for further processing, which may include chemical treatment for lysis and breakdown of the paraffin or frozen tissue embedding material. The sample may also undergo bead beating or some other mechanical lysis process, as discussed above.

Figure 19:
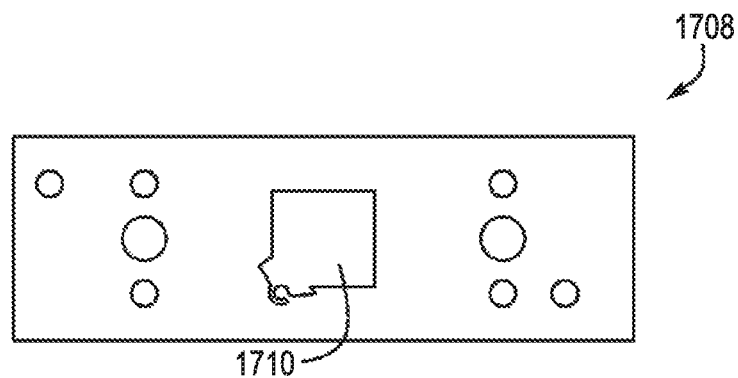
FIG. 19 is a top view of a slide inset with a microperforated region for the microfluidic chip of FIG. 18.
Figure 20:
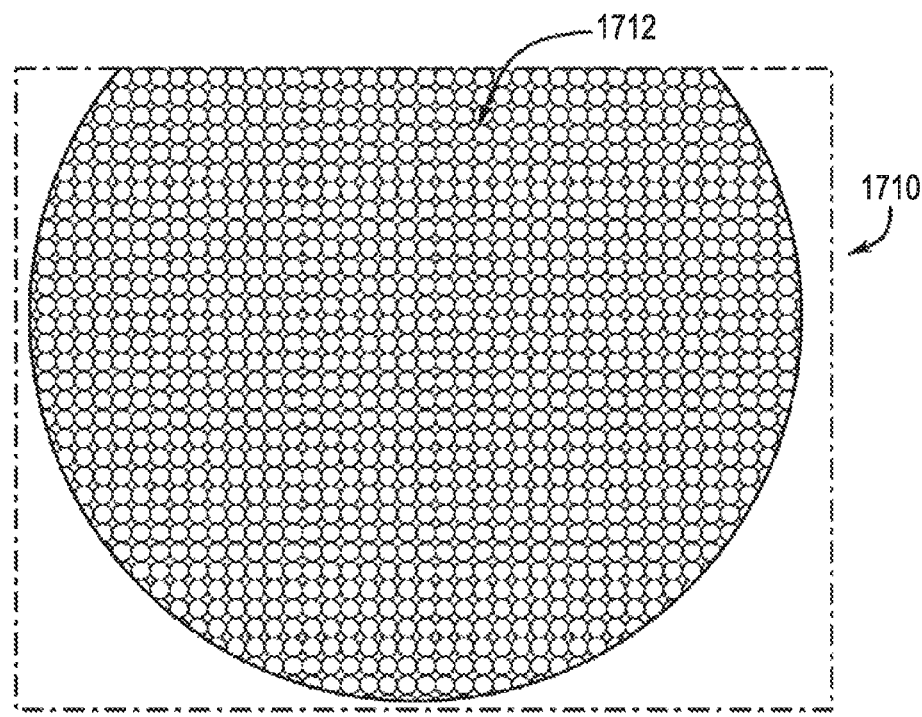
FIG. 20 is an illustration of a glass microperforation that may be used in the slide inset of FIG. 19.

The center of the slide layer 1708 may have a microperforated region 1710 to provide large particle filtering in fluidic device 202'. FIG. 19 further illustrates slide layer 1708 and the disposition of the microperforated region 1710 and FIG. 20 provides an illustration of pores 1712 of the microperforated region 1710. In some implementations, the pores 1712 may have a diameter of about 200 µm and be separated by a pitch of about 250 µm. The microperforated region 1710 may prevent the flow of large debris that may come from breaking the FFPE or frozen tissues, such as paraffin, particles. This may protect the membrane (one example of filter 280') from potentially damaging debris. The microperforated region 1710 may also provide physical support for placement of the samples during preparation of the fluidic chip 1700 and during pretreatment of samples.

Figure 21:
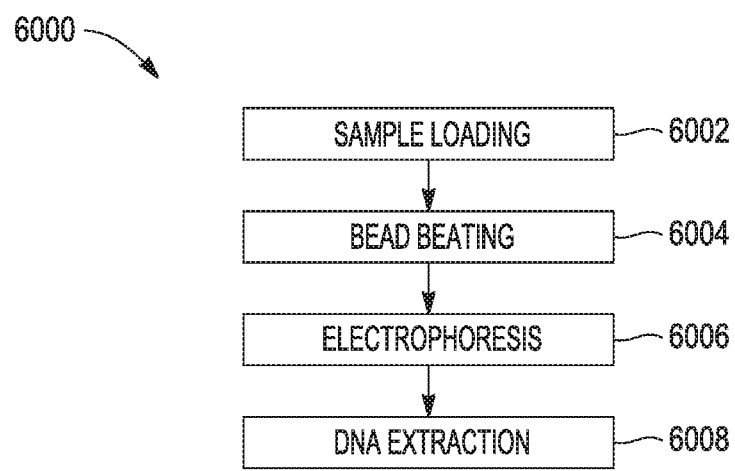
FIG. 21 illustrates a method that may be used with the system of FIG. 5B for streamlined separation and extraction of nucleic acids, in accordance with an implementation.

With the foregoing in mind, FIG. 21 provides a method 6000 to extract DNA from a sample. Method 6000 may be performed by system 200'. In certain systems 200', the method may be performed automatically, or without or little user intervention. Method 6000 may also be performed employing a fluidic device 202' coupled to appropriate fluidic, electrical and acoustic actuators, as discussed above with reference to FIG. 5B. In a sample loading process 6002, system 200' or a user may load sample to a sample chamber 203B in the fluidic device 202'. The chamber 203B may be preloaded with beads 258 or any other suitable mechanism to promote lysis. Alternatively, the sample may be mixed with beads 258 prior to loading. At the end of a sample loading process 6002, the flow induced by system 200' may be stopped. In some implementations, the remaining processes may take place at least partially simultaneously with loading.

Sample loaded in sample loading process 6002 may contain biological material having DNA for extraction. A bead beating process 6004 may be lead to rupturing cell walls, cellular membranes and/or nuclear membranes that may be enveloping DNA. Bead beating process may generate lysis due to mechanical forces in sample chamber volume. For example, pressure waves received in the sample chamber 203B may generate shear forces in the fluid that may rupture cell walls. Moreover, beads 258 in the sample chamber volume that are vibrating due to an interaction with the pressure waves may lead to collisions that can break cell walls. Note further that the solvent of sample may be adjusted to facilitate the lysis process by adjustments in temperature, osmolarity, and/or acidity. Enzymes or other catalysts may also be added to assist in the digestion of cell membranes, based on the sample used. Note further that appropriate chemical treatments may be used when the sample includes a frozen tissue or an FFPE tissue.

In order to obtain good elution performance, the sample and the elution buffers may be adjusted such that electrophoretic mobility of the ions in the lysis buffer are lower than that of nucleic acid and, further, that the electrophoretic mobility of the ions in the elution buffer are higher than that of nucleic acid. For example, when extracting DNA, that may have electrophoretic mobility ranging from about $3 \times 10^{-4}$ cm$^2$ V$^{-1}$ s$^{-1}$ to about $3.6 \times 10^{-4}$ cm$^2$ V$^{-1}$ s$^{-1}$, the lysis buffer may be chosen such that the constituent ions have an electrophoretic mobility of less than about $2 \times 10^{-4}$ cm$^2$ V$^{-1}$ s$^{-1}$ compared to the molecules of interest and the elution buffer may be chosen such that the buffer ions have an electrophoretic above about $4 \times 10^{-4}$ cm$^2$ V$^{-1}$ s$^{-1}$. The choice of additives, such as detergents, salts, co-factors, enzymes, nucleic acid stabilizers, and pH stabilizers may take ionic mobility in account. Additives that may be added to the lysis buffer may include calcium chloride, EDTA, Urea, Sodium Dodecyl Sulfate (SDS), Triton X-100, CHAPS detergent, among others.

The sample loading process may also be used for concentration of the sample. In some applications, the biological material in the sample may be dilute and the fluidic device 202' may be used to concentrate the material into sample chamber 203B. As an illustration of a concentration protocol during sample loading process, a fluidic device 202' may be initially configured to have the outlet sample channel 1404 and the inlet elution channel 1412 closed. The dilute sample may then be loaded at the inlet sample channel 1402 and the excess solute may be removed via the outlet elution channel 1414. By applying a concentration protocol, large volumes of diluted biological samples may be treated in a single process.

During bead beating process 6004, or following its end, an electrophoresis process 6006 may begin. During the electrophoresis process 6006, a voltage may be applied between anodes and cathodes (e.g., electrodes 244, 246) of fluidic device 202' to generate an electric field that drives DNA from the sample chamber 203B to an elution chamber 203A. The voltage applied and the duration of the voltage applied may be based on a protocol stored in system 200', based on the type of sample used and/or the size of DNA fragments desired. In some applications, the power supply 260' may induce a specific current between the cathode and the anode instead of a specific voltage. Power supply voltages, currents, and or durations may be monitored and adjusted by a controller 206' as detailed above.

At the end of the electrophoresis process 6006, a proportion of the DNA may be in the elution chamber 203A. The portion may be significant—e.g., greater than 50% by volume. A DNA extraction process 6008 may be used to retrieve the purified DNA from the elution chamber 203A. In some situations, system 200' may cause a flow in the elution chamber 203A for collection and posterior processing. In other implementations, elution chamber 203A may have beads with affinity to DNA. As DNA moves into elution chamber 203A during the electrophoresis process 6006, it may attach to the beads. Beads may be separated from the elution volume during DNA extraction process 6008, leading to improve the concentration and purity of DNA extracted. For example, the beads may be magnetic, and beads may be separated from the elution volume employing a magnetic separation process. In other processes, the bead may be large enough to be separated through filtering and/or sieving of the elution volume. DNA may then be released from the beads in a fresh buffer. Some applications, such as sequencing and amplification, may employ DNA-attached bead directly.

Advantages of the system 200' and processes described herein are related to the high quality of DNA produced by an integrated and streamlined process for extraction of DNA from biological samples. Implementations may allow extraction of useful amounts of DNA with purity suitable for sequencing, amplification, and other useful biochemical processes. Examples of the methods may allow for acquisition of DNA from heterogeneous samples having different types of organisms. Moreover, when dealing with heterogeneous samples, the dimensions of the cell or the types of cell wall do not generate any bias in the amount of DNA in the product. As a result, the DNA produced may be employed for quantitative analysis, such as in metagenomic studies, quantitative microbiome studies and/or population metabolism studies. Note further that the above process may be employed to acquire other nucleic acids, such as RNA, with minor adjustments to the buffer and/or the process.

To further illustrate the present disclosure, examples are given herein. It is to be understood that these examples are provided for illustrative purposes and are not to be construed as limiting the scope of the present disclosure.

EXAMPLES

Example 1

In this example, controlled pore glass (100 nm pore diameter) beads (CPG beads) were used as the substrate, and LUVIQUAT® FC 550 (40 wt % in water, from BASF Corp.) was used to coat the substrate.

A 1 wt % solution of the LUVIQUAT® FC 550 was created by dilution of the 40% solution with deionized water. CPG beads were then added to the solution and manually shaken and allowed to incubate for about 45 minutes. Excess liquid was removed from the settled coated CPG beads, and the coated CPG beads were heated and dried in a convection oven at 60° C. overnight.

Water was added to the dried, coated CPG beads and they were sonicated for about 15 minutes. The coated CPG beads were then washed twice with water and then sonicated in 1× phosphate buffered saline (1×PBS) for about 15 minutes followed by 5 washes with 1×PBS.

Human whole blood samples (from two different lots, referred to herein as lot 183 and lot 458) were obtained from Bioreclamation IVD. Approximately 2 mm of the coated CPG beads were placed in 1.5 mL polypropylene, non-stick centrifuge tubes. The coated beads were rinsed one final time with 1 mL 1×PBS buffer. The buffer was removed via pipette. 1 mL of whole blood from each lot was then pipetted onto the coated CPG beads in respective tubes, and the tubes were sealed and constantly manually inverted for about 20 minutes. The tubes were then allowed to incubate vertically for about 10 minutes to allow the coated CPG beads to settle. The blood was then removed using a pipette, and 1×PBS was added to rinse the coated CPG beads. The rinsate was pipetted off, and the rinsing was repeated several times, until the rinsate became colorless and transparent. Then, all excess liquid was removed from the coated CPG beads via pipette.

For the examples and comparative examples in Table 1 below, the following general procedure was utilized (although incremental changes may have been made for any given example or comparative example). For the general procedure, about 75 µl of 20×PBS was added to elute the cfDNA from the coated CPG beads. This was vortexed and allowed to incubate for about 30 minutes. Then 60 µL of the eluted cfDNA was removed from the coated CPG beads and 5 µL of proteinase K (New England Biolabs) was added. This was briefly vortexed and then incubated at about 56° C. for about 1 hour. Finally, 60 µL of the final mixture was removed and the extracted cfDNA was purified using a 2×SPRI cleanup.

Plasma was also isolated from the same whole blood samples. The LUVIQUAT® FC 550 coated CPG beads were tested on the plasma samples using a similar procedure to that described for the whole blood sample.

As a comparison, a commercial cfDNA isolation kit (Bioo Scientific Next Prep) was used to extract cfDNA from the plasma sample.

The quantity of isolated (i.e., extracted and eluted) cfDNA using the coated CPG beads and using the commercial cfDNA isolation kit was determined using TapeStation analysis (Agilent) and QUBIT™ fluorometric quantitation (ThermoFisher). Both of these instruments utilize intercalating dyes which fluoresce upon complexation with DNA. The results in terms of ng of cfDNA isolated per mL of blood (volume of original whole blood samples) are shown in Table 1.

TABLE 1

| ID | Isolation Technique Sample | TapeStation (ng/mL) | Qubit (ng/mL) |
|---|---|---|---|
| 1 | LUVIQUAT ® FC 550 coated CPG beads Whole blood, lot 183 | 3.30 | 3.57 |
| 2 | LUVIQUAT ® FC 550 coated CPG beads Plasma, lot 183 | 3.84 | 2.37 |
| C3 | Commercial cfDNA isolation kit Plasma, lot 183 | 0.78 | 1.43 |
| 4 | LUVIQUAT ® FC 550 coated CPG beads Whole blood, lot 458 | 11.78 | 8.8 |
| 5 | LUVIQUAT ® FC 550 coated CPG beads Plasma, lot 458 | 14.48 | 7.0 |
| C6 | commercial cfDNA isolation kit Plasma, lot 458 | 4.48 | 4.32 |

The results in Table 1 illustrate that the LUVIQUAT® FC 550 coated CPG beads extract and elute from about 2× (2 times) to about 4.2× more cfDNA from whole blood samples than the commercial kit isolates from plasma samples. The results in Table 1 illustrate that the LUVIQUAT® FC 550 coated CPG beads extract and elute from about 1.6× to about 4.9× more cfDNA from plasma samples than the commercial kit isolates from plasma samples.

Figure 4:
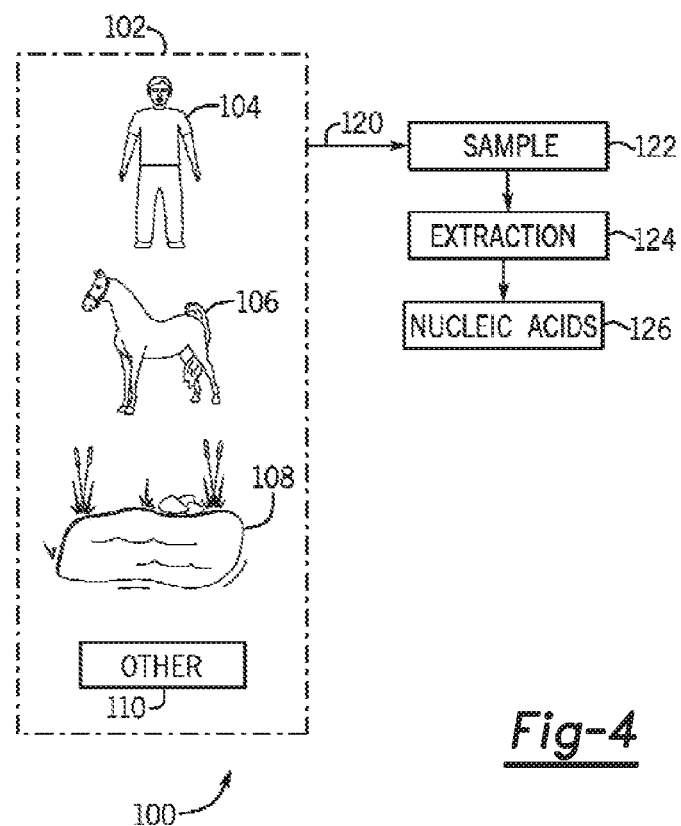
FIG. 4 depicts a schematic view of an example of a use case for obtaining purified nucleic acids from samples, in accordance with an implementation.

Additional TapeStation results, in terms of sample intensity (FU, fluorescence units) versus size of the fragmented DNA (bp or base pairs), for the each of these isolation technique/sample combinations are also shown in FIGS. 4A and 4B. FIG. 4A depicts the results for the lot 183 samples (1 and 2) and control (C3). FIG. 4B depicts the results for the lot 458 samples (4 and 5) and control (C6). In both FIGS. 4A and 4B, cfDNA is represented by the peaks at about 150 bp and about 400 bp, and the peaks at 15 bp and 10,000 bp are marker peaks. Marker peaks are used to calibrate the instrument so that the positions of the sample peaks can be estimated in terms of bp. The markers are also used for quantifying the amount of DNA present.

Figure 22A:
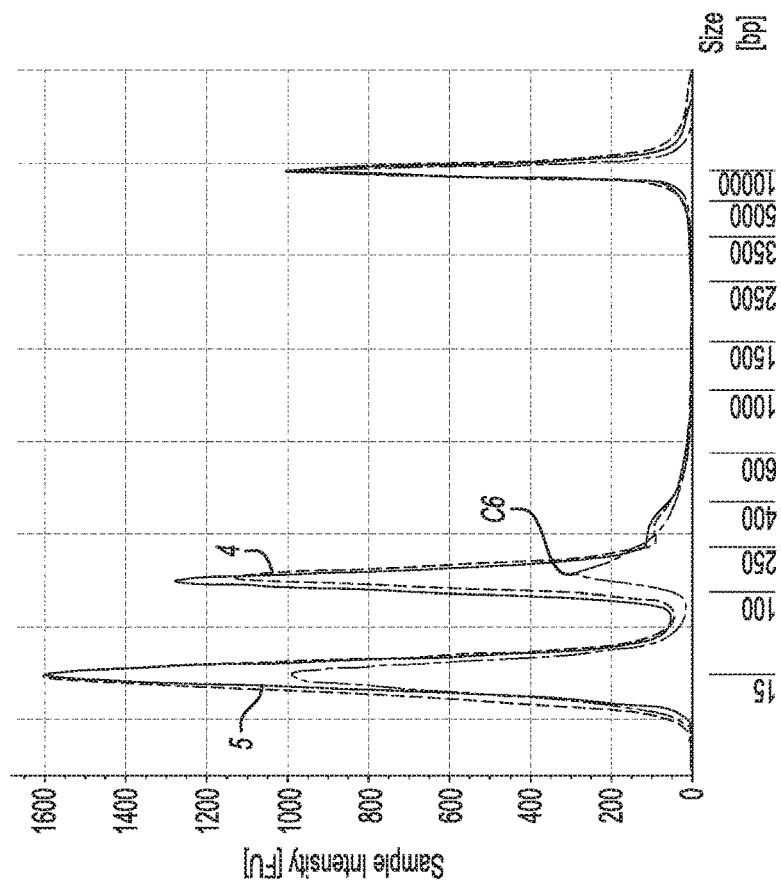
FIGS. 22A and 22B are graphs depicting, in one example, sample intensity (fluorescence units (FU), Y-axis) versus the size of the fragmented DNA (bp or base pairs, X-axis), for different isolation technique/sample combinations.
Figure 22B:
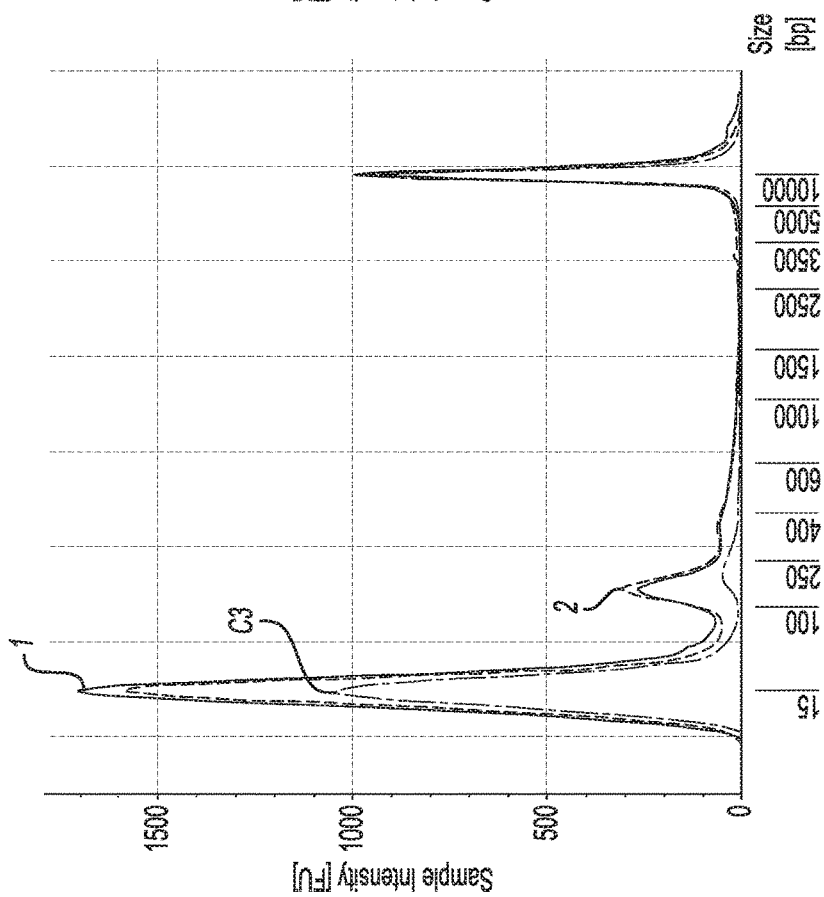

The results in FIGS. 22A and 22B illustrate that the cfDNA isolated directly from whole blood or from plasma using the LUVIQUAT® FC 550 coated CPG beads has a higher yield compared to the commercial kit from plasma. These results indicate that the high yields of cfDNA using the LUVIQUAT® FC 550 coated CPG beads were not due to anomalous generation of DNA fragments due to the presence of the white blood cells in whole blood. These results also indicate that no gDNA contamination was observed.

Example 2 cfDNA was extracted from human whole blood samples (from two different lots, referred to herein as lot 817 and lot 818). The cfDNA was extracted in a similar manner as described in Example 1, using LUVIQUAT® FC 550 coated CPG beads. Plasma was also isolated from the whole blood samples, and a commercial cfDNA isolation kit (Bioo Scientific Next Prep) was used to extract cfDNA from the plasma sample.

Some of the isolated cfDNA from each of the whole blood samples and from the plasma sample was carried through library preparation using a process of SPRI cleanup followed by end repair, A-tailing, ligation, SPRI, and 11 cycles of PCR, followed by a final SPRI cleanup.

Figure 23:
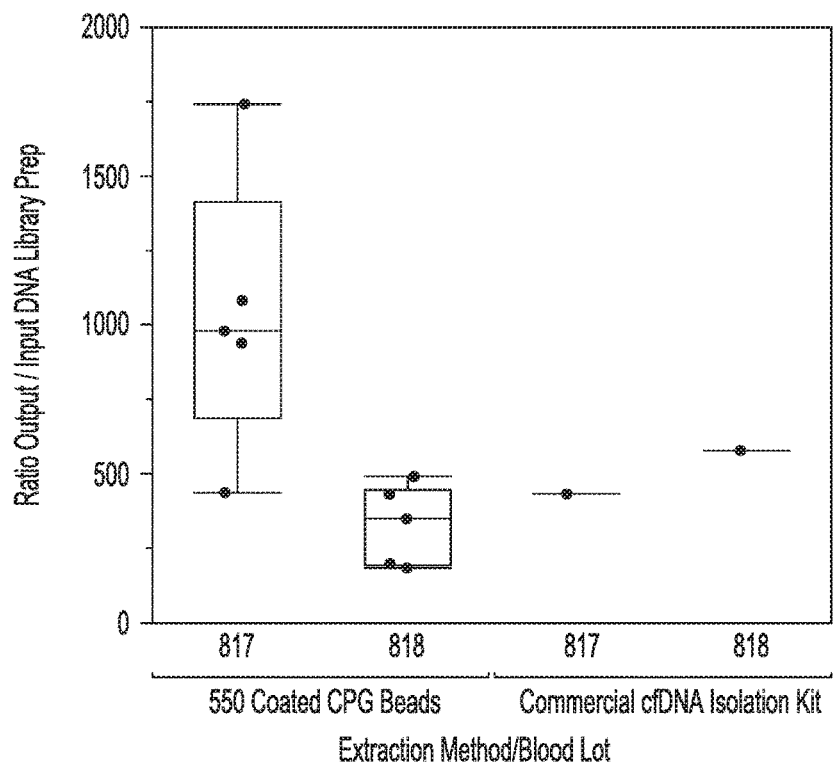
FIG. 23 is a graph depicting, in one example, the ratio of output/input DNA library prep (Y-axis) versus the extraction method for different whole blood lots.

FIG. 23 shows the ratio of output/input DNA library prep (Y-axis) versus the extraction method (i.e., 550 coated CPG beads or commercial cfDNA isolation kit) (X-axis) for blood lots 817 and 818 (also on the X-axis). The results indicate that the library yield for the 550 coated CPG bead extracted cfDNA was similar to the control cfDNA isolated from plasma using the commercial NextPrep kit.

Example 3

Other polycation coated CPG beads were prepared in a similar manner as described in Example 1, except that the coated CPG beads were not dried and sonicated. In this example, the incubation time of the beads in the polycation 14 was also increased to several hours. The polycations that were used are shown in Table 2. The various polycation coated CPG beads were exposed to whole blood as described in Example 1, and cfDNA was captured and eluted as described in Example 1. As a comparison, a commercial cfDNA isolation kit (Bioo Scientific Next Prep) was used to extract cfDNA from the plasma sample.

The quantity of isolated (i.e., extracted and eluted) cfDNA using the various polycation coated CPG beads and using the commercial cfDNA isolation kit was determined using TapeStation 4200 analysis (Agilent) (with the High Sensitivity D5000 kit or the High Sensitivity D1000 kit). While these quantitative results are not shown, Table 2 indicates whether the various polycation coated CPG beads captured and eluted similar or more than the associated control sample.

TABLE 2

| ID | Polycation | cfDNA capture and elution of coated CPG beads ≥ Nextprep control |
|---|---|---|
| A | Luviquat ® FC 550 | Yes |
| B | Luviquat ® FC 370 | Yes |
| C | Luviquat ® HOLD | Zero* |
| D | Luviquat ® PQ11 AT** | Yes |
| E | Polyquaternium-10** | Yes |
| F | Poly (diallyldimethylammonium chloride-co-acrylamide) (55% acrylamide) | No |
| G | Polyquaternium-2** | Yes |
| H | Poly(1-vinylpyrrolidone-co-2-dimethylaminoethyl methacrylate) | Zero |
| I | Poly(ethylene imine) (PEI) | No |
| J | Poly(L-lysine) (PLL) | No |
| K | Poly(L-histidine) | No |

*Zero means below the detection limit; in these instances, cfDNA extraction/elution was not observed (i.e., cfDNA was either not captured or captured and not eluted)
**gDNA detected The results presented in Table 2 indicate whether the cfDNA capture and elution for each of the tested polymer or copolymer was greater than or equal to the cfDNA capture and elution using the commercial cfDNA isolation kit. The results in Table 2 indicate that LUVIQUAT® FC 550 (sample A) and LUVIQUAT® FC 370 (sample B) are polycations that can both extract and elute cfDNA better than the commercial cfDNA isolation kit. The results in Table 2 also indicate that LUVIQUAT® PQ11 AT can both extract and elute cfDNA, but some gDNA was detected from the electropherogram (i.e., the Tapestation results, not shown). The gDNA level that was detected may be acceptable in some applications (e.g., non-invasive prenatal testing (NIPT) or oncology applications). Polyquaternium-2 and Polyquaternium-10 (Samples G and E, respectively) were able to extract and elute the cfDNA similarly to or better than the commercial cfDNA isolation kit. With Sample E, some residual cfDNA was observed on the beads after elution. With these samples (G and E), some gDNA was detected, but the level detected may be acceptable in some applications. Moreover, it is believed that other methods (e.g., polishing and/or grinding as described herein) may further reduce gDNA contamination.

Polycations, C, F and H-K did not extract and elute cfDNA similarly to or better than the commercial cfDNA isolation kit.

Example 4

In this example, controlled pore glass (100 nm pore diameter) beads (CPG beads) were used as the substrate, and LUVIQUAT® FC 550 (40 wt % in water, from BASF Corp.) was used to coat the substrate.

A 1 wt % solution of the LUVIQUAT® FC 550 was created by dilution of the 40% solution with deionized water.

CPG beads were then added to the solution and manually shaken and allowed to incubate for about 45 minutes. Excess liquid was removed from the settled coated CPG beads, and the coated CPG beads were heated and dried in a convection oven at 60° C. overnight.

Water was added to the dried, coated CPG beads and they were sonicated for about 15 minutes. The coated CPG beads were then washed twice with water and then sonicated in 1× phosphate buffered saline (1×PBS) for about 15 minutes followed by 5 washes with 1×PBS.

cfDNA from 1 mL aliquots of human whole blood samples (from two different lots, referred to herein as lot 815 and lot 816) was extracted using the LUVIQUAT® FC 550 coated CPG beads in the same manner as described in Example 1. Plasma was also isolated from the same whole blood samples. As a comparison, a commercial cfDNA isolation kit (Bioo Scientific Next Prep) was used to extract cfDNA from the plasma sample.

The isolated cfDNA was characterized by electrophoresis and then put through library preparation as described in Example 2. The resultant libraries were quantified using electrophoresis (Agilent TapeStation 4200) and were successfully sequenced using respective flow cells including a non-patterned glass substrate with 4 lanes defined thereon, each lane having a poly(N-(5-azidoacetamidylpentyl) acrylamide-co-acrylamide) (PAZAM) layer formed thereon, and primers grafted on the PAZAM layer. The libraries were loaded into the respective flow lanes, and fragments were captured by the complementary primers. Each fragment was amplified into distinct clonal clusters, and 2×50 cycle paired end sequencing was performed.

Figure 24A:
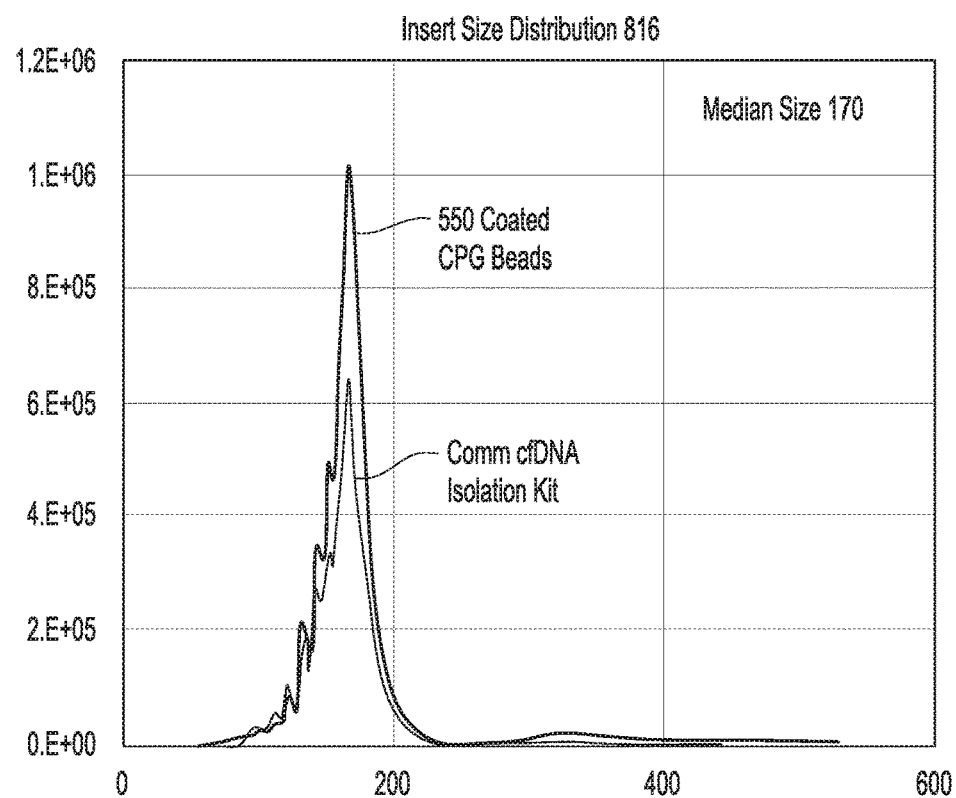
FIG. 24A is a graph depicting, in one example, the insert size distribution for cell free DNA (cfDNA) samples sequenced after being extracted using an example of the nucleic acid extraction material disclosed herein and for cfDNA samples sequenced after being extracted via a control method.
Figure 24B:
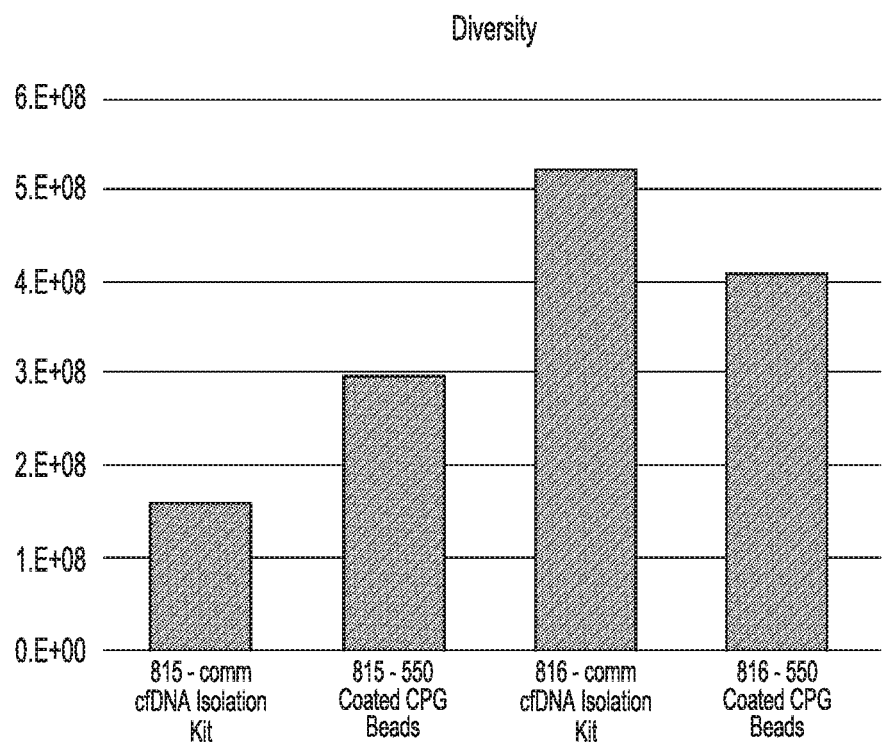
FIG. 24B is a graph depicting, in one example, the diversity for cfDNA samples sequenced after being extracted using an example of the nucleic acid extraction material disclosed herein and for cfDNA samples sequenced after being extracted via a control method.
Figure 24C:
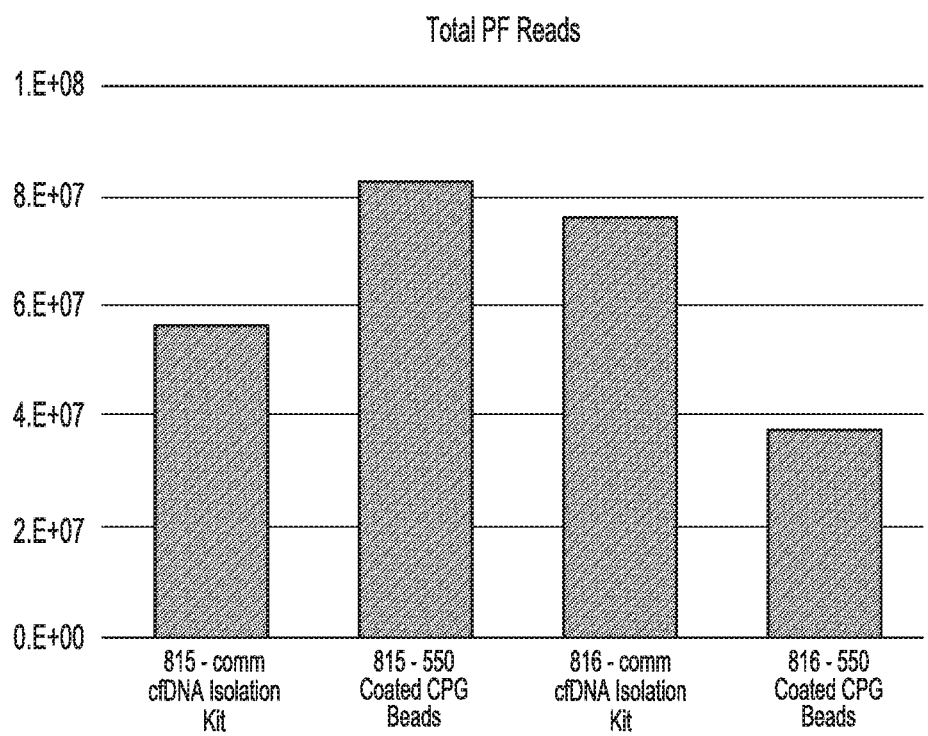
FIG. 24C is a graph depicting, in one example, the total percentage of clusters that passed filters (i.e., total PF reads) for cfDNA samples sequenced after being extracted using an example of the nucleic acid extraction material disclosed herein and for cfDNA samples sequenced after being extracted via a control method.

The following sequencing quality metrics were examined: the insert size distribution of the paired-end library (FIG. 24A) was determined for blood lot 816, diversity (i.e., having equal proportions of A, C, G, and T nucleotides at each base position in a sequencing library) (FIG. 24B) was determined for blood lots 815 and 816, and total PF reads (i.e., percentage of clusters that passed filters) (FIG. 24C) were determined for blood lots 815 and 816. As illustrated in FIGS. 24A through 24C, the sequencing metrics were similar between the 550 coated CPG bead extracted cfDNA and the control cfDNA isolated from plasma using the commercial NextPrep kit.

Example 5

One batch of LUVIQUAT® FC 550 coated CPG beads from Example 1 were used in this example.

LUVIQUAT® FC 370 coated CPG beads were also prepared using a similar process. For the LUVIQUAT® FC 370 coated CPG beads, controlled pore glass (100 nm pore diameter) beads (CPG beads) were used as the substrate, and LUVIQUAT® FC 370 (40 wt % in water, from BASF Corp.) was used to coat the substrate. More particularly, a 1 wt % solution of the LUVIQUAT® FC 370 was created by dilution of the 40% solution with deionized water. CPG beads were then added to the LUVIQUAT® FC 370 solution and manually shaken and allowed to incubate for about 45 minutes. Excess liquid was removed from the settled coated CPG beads, and the coated CPG beads were heated and dried in a convection oven at 60° C. overnight.

Water was added to the dried, LUVIQUAT® FC 370 coated CPG beads and they were sonicated for about 15 minutes. The LUVIQUAT® FC 370 coated CPG beads were then washed 5 times with water and then sonicated in phosphate buffered saline (PBS) for about 15 minutes followed by 5 washes with PBS.

cfDNA from respective 1 mL aliquots of human whole blood samples (from a single lot) was extracted using the batch of LUVIQUAT® FC 550 coated CPG beads and the LUVIQUAT® FC 370 coated CPG beads. The incubation period was about 20 minutes, with manual inversion taking place every few minutes.

The blood was then removed using a pipette, and 1×PBS was added to rinse the LUVIQUAT® FC 550 coated CPG beads and the LUVIQUAT® FC 370 coated CPG beads. The rinsate was pipetted off, and the rinsing was repeated several times, until the rinsate became colorless and transparent. Then, all excess liquid was removed from the LUVIQUAT® FC 550 coated CPG beads and the LUVIQUAT® FC 370 coated CPG beads via pipette.

For elution, about 75 µl of 20×PBS was added to elute the cfDNA from the LUVIQUAT® FC 550 coated CPG beads and the LUVIQUAT® FC 370 coated beads. This was vortexed and allowed to incubate for about 30 minutes. Then 75 µL of the eluted cfDNA was removed from the LUVIQUAT® FC 550 coated CPG beads and the LUVIQUAT® FC 370 coated CPG beads and 5 µL of proteinase K (New England Biolabs) was added. This was briefly vortexed and then incubated at about 56° C. for about 1 hour. Finally, 60 µL of the final mixture was removed and the extracted cfDNA was purified using a 2×SPRI cleanup.

The extraction and elution process was repeated with the batch of LUVIQUAT® FC 550 coated CPG beads.

Figure 25:
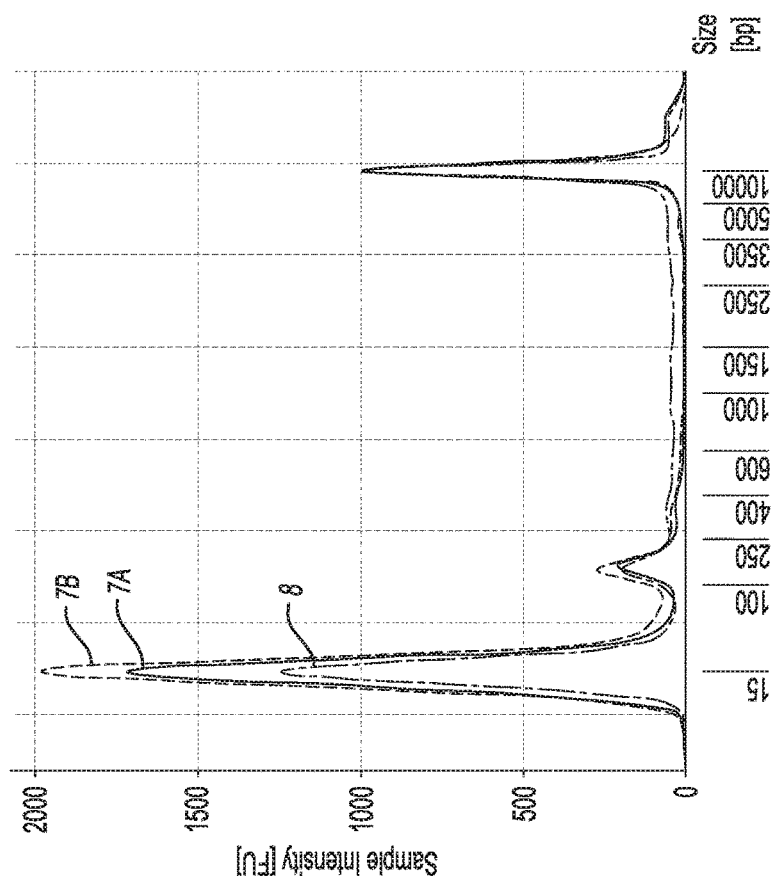
FIG. 25 is a graph depicting, in one example, sample intensity (FU, Y-axis) versus the size of the fragmented DNA (bp or base pairs, X-axis), for two examples of the nucleic acid extraction materials disclosed herein.

The quantity of isolated (i.e., extracted and eluted) cfDNA using the LUVIQUAT® FC 550 coated CPG beads and using the LUVIQUAT® FC 370 coated CPG beads was determined using TapeStation 4200 analysis (Agilent) (with the High Sensitivity D5000 kit or the High Sensitivity D1000 kit). The TapeStation results, in terms of sample intensity (FU, fluorescence units) versus size of the fragmented DNA (bp or base pairs), are shown in FIG. 25. FIG. 25 depicts the results for the first extraction/elution with the LUVIQUAT® FC 550 coated CPG beads (7A), the repeated extraction/elution with the LUVIQUAT® FC 550 coated CPG beads (7B), and the extraction/elution with the LUVIQUAT® FC 370 coated CPG beads (8). In FIG. 25, cfDNA is represented by the peaks at about 150 bp and about 400 bp, and the peaks at 15 bp and 10,000 bp are marker peaks. Marker peaks are used to calibrate the instrument so that the positions of the sample peaks can be estimated in terms of bp. The markers are also used for quantifying the amount of DNA present. The results in FIG. 25 illustrate that the LUVIQUAT® FC 550 coated CPG beads and the LUVIQUAT® FC 370 coated CPG beads extract and elute cfDNA similarly, and that the extraction/elution can be repeated with the coated beads.

Example 6

Once batch of LUVIQUAT® FC 550 coated CPG beads from Example 1 were used in this example. Comparative beads coated with polyethyleneimine (PEI) were also prepared using a similar process. For the comparative PEI coated beads, controlled pore glass (100 nm pore diameter) beads (CPG beads) were used as the substrate, and PEI (1800 g/mol) was used to coat the substrate.

cfDNA from respective 1 mL aliquots of human whole blood samples (from blood lot 183) was extracted using the batch of LUVIQUAT® FC 550 coated CPG beads and the comparative PEI coated beads. Both extraction and elution were performed as described in Example 5.

Figure 26:
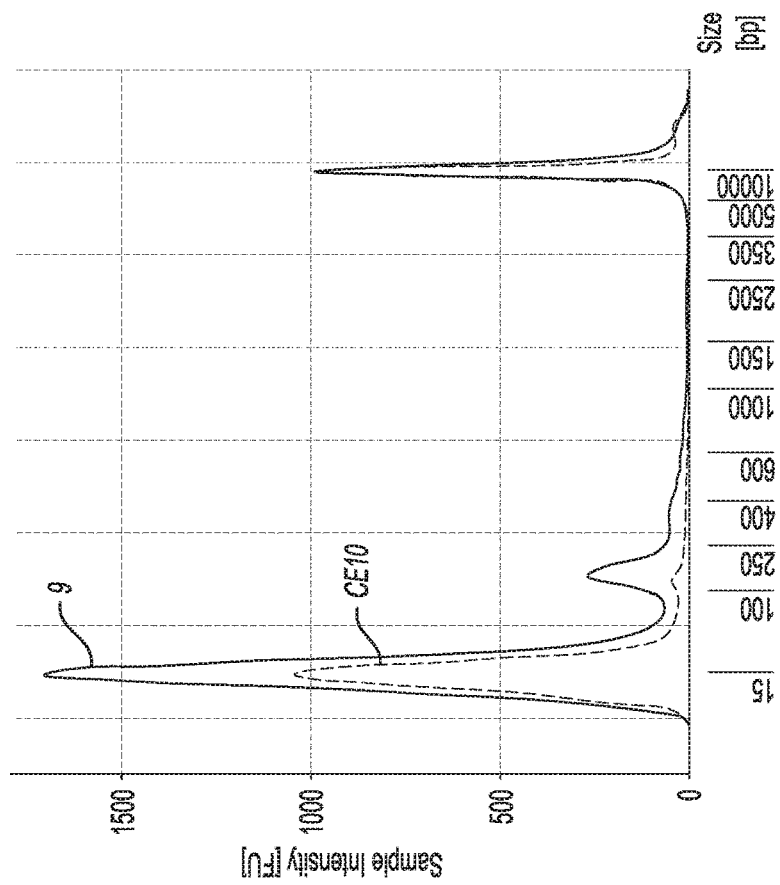
FIG. 26 is a graph depicting, in one example, sample intensity (FU, Y-axis) versus the size of the fragmented DNA (bp or base pairs, X-axis), for a comparative extraction material and an example of the extraction material disclosed herein.

The quantity of isolated (i.e., extracted and eluted) cfDNA using the LUVIQUAT® FC 550 coated CPG beads and using the comparative PEI coated beads was determined using TapeStation 4200 analysis (Agilent) (with the High Sensitivity D5000 kit or the High Sensitivity D1000 kit). The TapeStation results, in terms of sample intensity (FU, fluorescence units) versus size of the fragmented DNA (bp or base pairs), are shown in FIG. 26. In FIG. 26, cfDNA is represented by the peaks at about 150 bp and about 400 bp, and the peaks at 15 bp and 10,000 bp are marker peaks. The peaks just to the right of the 10,000 bp marker peaks are indicative of genomic DNA (gDNA).

The results in FIG. 26 illustrate that the cfDNA isolated directly from whole blood using the LUVIQUAT® FC 550 coated CPG beads (9) has a much higher yield compared to the comparative PEI coated beads (CE10). These results also indicate that gDNA contamination is slightly higher for the comparative PEI coated beads (CE10) than for the LUVIQUAT® FC 550 coated CPG beads (9).

Additional Notes

It should be appreciated that all combinations of the foregoing concepts and additional concepts discussed herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such ranges were explicitly recited. For example, a range from 30 minutes to about 72 hours should be interpreted to include not only the explicitly recited limits of from 30 minutes to about 72 hours, but also to include individual values, such as about 45 minutes, about 59 minutes, about 5 hours, about 50 hours, etc., and sub-ranges, such as from about 35 minutes to about 45 hours, from about 40 minutes to about 55 hours, etc. Furthermore, when "about" and/or "substantially" are/is utilized to describe a value, this is meant to encompass minor variations (up to +/−10%, such as, for example less than or equal to ±5%, or less than or equal to ±2%, or less than or equal to ±1%, or less than or equal to ±0.5%, or less than or equal to ±0.2%, or less than or equal to ±0.1%, or less than or equal to ±0.05%) from the stated value.

While several examples have been described in detail, it is to be understood that the disclosed examples may be modified. Therefore, the foregoing description is to be considered non-limiting.

What is claimed is:

1. A deoxyribonucleic acid extraction material, comprising:

a substrate selected from the group consisting of controlled pore glass, a metal oxide, a metal with an oxide layer, and carbon; and a polycation i) physically bonded, via physisorption or non-covalent bonding with biotin-streptavidin, or ii) covalently bonded to at least a portion of a surface of the substrate, the polycation consisting of a polymer synthesized from a quaternized monomer selected from the group consisting of a quaternized 1-vinylimidazole monomer having structure (I):

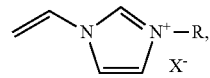

wherein R in structure (I) is an alkyl group having from 1 carbon atom to 10 carbon atoms and X⁻ in structure (I) is a counterion selected from the group consisting of chloride, methyl sulfate, ethyl sulfate, iodide, hydrogen sulfate, acetate, and bromide, and a quaternized dimethylaminoethyl methacrylate monomer having structure (II):

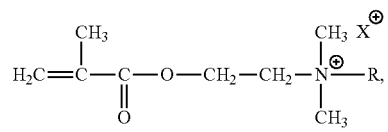

wherein R in structure (II) is an alkyl group having from 1 carbon atom to 10 carbon atoms and X in structure (II) is a counterion selected from the group consisting of chloride, methyl sulfate, ethyl sulfate, iodide, hydrogen sulfate, acetate, and bromide, or a copolymer synthesized from a neutral monomer selected from the group consisting of N-vinylpyrrolidone, acrylamide, and hydroxypropylmethacrylamide, and the quaternized 1-vinylimidazole monomer having structure (I) or the quaternized dimethylaminoethyl methacrylate monomer having structure (II).

2. The deoxyribonucleic acid extraction material as defined in claim 1, wherein the neutral monomer is N-vinylpyrrolidone, and wherein the polycation is a cationic copolymer including about 50% of the quaternized 1-vinylimidazole monomer and about 50% of the N-vinylpyrrolidone.

3. The deoxyribonucleic acid extraction material as defined in claim 1, wherein the neutral monomer is N-vinylpyrrolidone, and wherein the polycation is a cationic copolymer including about 30% of the quaternized 1-vinylimidazole monomer and about 70% of the N-vinylpyrrolidone.

4. The deoxyribonucleic acid extraction material as defined in claim 1, wherein the neutral monomer is N-vinylpyrrolidone, and wherein the polycation is a cationic copolymer including about 95% of the quaternized 1-vinylimidazole monomer and about 5% of the N-vinylpyrrolidone.

5. The deoxyribonucleic acid extraction material as defined in claim 1, wherein the neutral monomer is N-vinylpyrrolidone, and wherein the polycation is a cationic copolymer including about 33% of the quaternized dimethylaminoethyl methacrylate monomer and about 67% of the N-vinylpyrrolidone.

6. The deoxyribonucleic acid extraction material as defined in claim 1, wherein the quaternized 1-vinylimidazole monomer is selected from the group consisting of 3-methyl-1-vinylimidazolium chloride, 3-methyl-1-vinylimidazolium methyl sulfate, and 3-ethyl-1-vinylimidazolium ethyl sulfate.

7. The deoxyribonucleic acid extraction material as defined in claim 1, wherein the substrate includes a plurality of pores, wherein the substrate is selected from the group consisting of the controlled pore glass and the metal oxide, wherein the metal oxide is selected from the group consisting of porous silica, anodized aluminum oxide, and porous titanium oxide, wherein the surface to which the polycation is attached is an exterior substrate surface, an interior pore surface, or combinations thereof, and wherein each of the plurality of pores has a diameter ranging from about 5 nm to about 1 μm.

8. A method, comprising:
forming an aqueous solution of a polycation consisting of a polymer synthesized from a quaternized monomer selected from the group consisting of a quaternized 1-vinylimidazole monomer having structure (I):

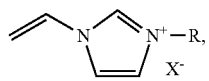

wherein R in structure (I) is an alkyl group having from 1 carbon atom to 10 carbon atoms and X in structure (I) is a counterion selected from the group consisting of chloride, methyl sulfate, ethyl sulfate, iodide, hydrogen sulfate, acetate, and bromide, and a quaternized dimethylaminoethyl methacrylate monomer having structure (II):

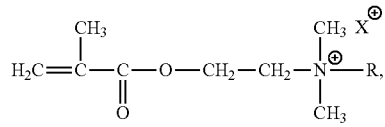

wherein R in structure (II) is an alkyl group having from 1 carbon atom to 10 carbon atoms and X in structure (II) is a counterion selected from the group consisting of chloride, methyl sulfate, ethyl sulfate, iodide, hydrogen sulfate, acetate, and bromide, or a copolymer synthesized from a neutral monomer selected from the group consisting of N-vinylpyrrolidone, acrylamide, and hydroxypropylmethacrylamide and the quaternized 1-vinylimidazole monomer having structure (I) or the quaternized dimethylaminoethyl methacrylate monomer having structure (II);
combining a substrate and the aqueous solution, the substrate being selected from the group consisting of controlled pore glass, a metal oxide, a metal with an oxide layer, and carbon;
incubating the substrate and the aqueous solution for a time ranging from about 30 minutes to about 72 hours to covalently bind or physically bind, via physisorption or non-covalent bonding with biotin-streptavidin, at least some of the polycation to the substrate and form a deoxyribonucleic acid extraction material; and
separating the deoxyribonucleic acid extraction material from the aqueous solution, wherein separating involves pouring off the aqueous solution, filtering, or using a magnet.

9. The method as defined in claim 8, wherein the neutral monomer is N-vinylpyrrolidone, and wherein the method further comprises selecting the polycation from the group consisting of i) a cationic copolymer including about 50% of the quaternized 1-vinylimidazole monomer and about 50% of the N-vinylpyrrolidone, ii) a cationic copolymer including about 30% of the quaternized 1-vinylimidazole monomer and about 70% of the N-vinylpyrrolidone, iii) a cationic copolymer including about 95% of the quaternized 1-vinylimidazole monomer and about 5% of the N-vinylpyrrolidone, and iv) a cationic copolymer including about 33% of the quaternized dimethylaminoethyl methacrylate monomer and about 67% of the N-vinylpyrrolidone.

10. The method as defined in claim 8, wherein the aqueous solution includes from about 0.001 wt % of the polycation in water to about 10 wt % of the polycation in water.

11. The method as defined in claim 8, wherein the substrate is a porous substrate selected from the group consisting of the controlled pore glass and the metal oxide, wherein the metal oxide is selected from the group consisting of porous silica, anodized aluminum oxide, and porous titanium oxide, and wherein the method further comprising polishing an exterior surface of the deoxyribonucleic acid extraction material to remove at least some of the polycation from the exterior surface of the porous substrate, wherein polishing involves a stirring process or a grinding process.

12. A method, comprising:
selectively extracting at least some cell free deoxyribonucleic acids from a sample of whole blood or plasma by exposing a deoxyribonucleic acid extraction material to the sample, the deoxyribonucleic acid extraction material including:
a substrate selected from the group consisting of controlled pore glass, a metal oxide, a metal with an oxide layer, and carbon; and
a polycation i) physically bonded, via physisorption or non-covalent bonding with biotin-streptavidin, or ii) covalently bonded to at least a portion of a surface of the substrate;
separating the deoxyribonucleic acid extraction material from the sample of whole blood or plasma, wherein separating involves pipetting the sample, pouring off the sample, or filtration; and
eluting the extracted cell free nucleic acids from the deoxyribonucleic acid extraction material by exposing the deoxyribonucleic acid extraction material to an elution buffer;
wherein the polycation consists of a cationic copolymer synthesized from a quaternized 1-vinylimidazole monomer having structure (I):

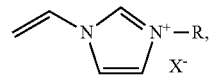

wherein R in structure (I) is an alkyl group having from 1 carbon atom to 10 carbon atoms and X in structure (I) is a counterion selected from the group consisting of chloride, methyl sulfate, ethyl sulfate, iodide, hydrogen sulfate, acetate, and bromide, and a neutral N-vinylpyrrolidone monomer selected from the group consisting of N-vinylpyrrolidone, acrylamide, and hydroxypropylmethacrylamide.

13. The method as defined in claim 12, wherein the elution buffer is a salt solution selected from the group consisting of phosphate buffered saline or a solution of a chaotropic salt selected from the group consisting of sodium trichloroacetate (Cl3CCOONa), guanidinium hydrochloride, guanidinium thiocyanate, sodium bromide (NaBr), sodium acetate, and sodium chloride (NaCl).

* * * * *

UNITED STATES PATENT AND TRADEMARK OFFICE
CERTIFICATE OF CORRECTION

PATENT NO. : 11,390,864 B2
APPLICATION NO. : 16/626221
DATED : July 19, 2022
INVENTOR(S) : Brian D. Mather et al.

It is certified that error appears in the above-identified patent and that said Letters Patent is hereby corrected as shown below:

On the Title Page

In item (56), in Column 2, under "Other Publications", Line 2, delete ""Calculatig" and insert -- "Calculating --.

In the Specification

In Column 1, Line 7, after "This application" insert -- is a national stage entry under 35 U.S.C. § 371 of PCT/US2018/040113, filed June 28, 2018, which itself --.

In the Claims

In Column 46, Lines 21-26, in Claim 1, delete

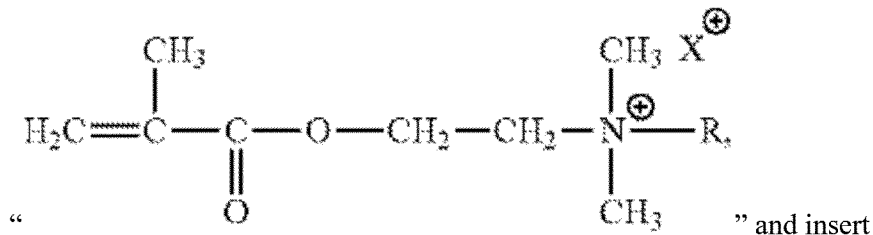

" and insert

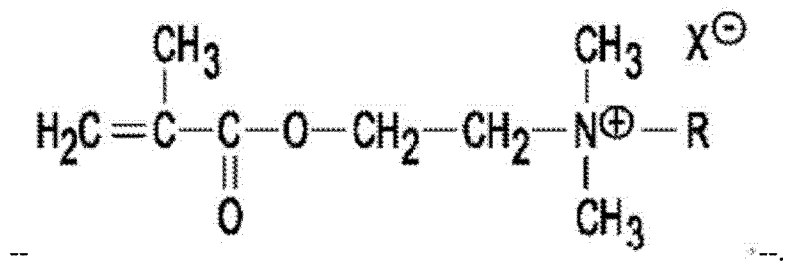

--.

Signed and Sealed this
Twenty-first Day of March, 2023

Katherine Kelly Vidal
*Director of the United States Patent and Trademark Office*

CERTIFICATE OF CORRECTION (continued)
U.S. Pat. No. 11,390,864 B2

In Column 47, Lines 31-36, in Claim 8, delete "

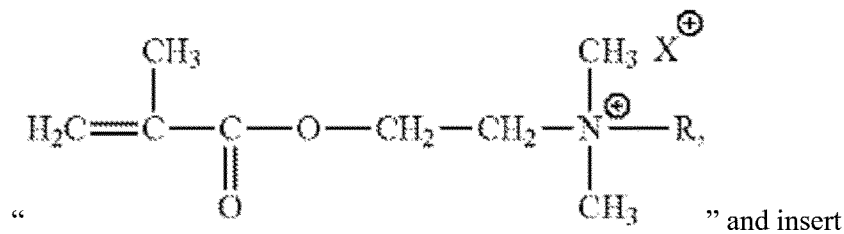

" and insert

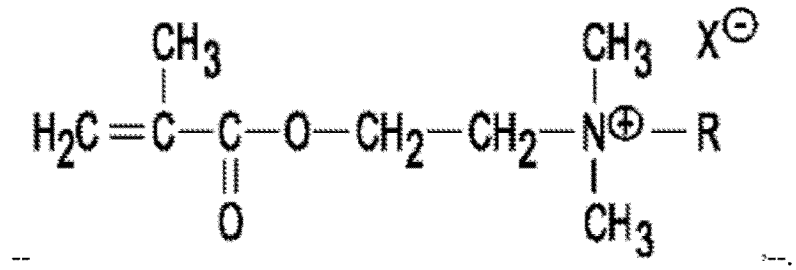

--.